(12) United States Patent
Lin et al.

(10) Patent No.: US 8,986,945 B2
(45) Date of Patent: **\*Mar. 24, 2015**

(54) METHODS AND COMPOSITIONS FOR DETECTING RARE CELLS FROM A BIOLOGICAL SAMPLE

(75) Inventors: Ping Lin, San Diego, CA (US); Andrea Ghetti, San Diego, CA (US); Wenge Shi, San Marcos, CA (US); Mengjia Tang, San Diego, CA (US); Gioulnar I. Harvie, San Diego, CA (US); Huimin Tao, San Diego, CA (US); Guoliang Tao, San Diego, CA (US); Lei Wu, San Diego, CA (US); David Cerny, San Diego, CA (US); Jia Xu, San Diego, CA (US); Douglas T. Yamanishi, Redondo Beach, CA (US)

(73) Assignee: Aviva Biosciences Corporation, San Diego, CA (US)

( \* ) Notice: Subject to any disclaimer, the term of this patent is extended or adjusted under 35 U.S.C. 154(b) by 1127 days.

This patent is subject to a terminal disclaimer.

(21) Appl. No.: 11/841,972

(22) Filed: Aug. 20, 2007

(65) Prior Publication Data

US 2008/0206757 A1 Aug. 28, 2008

Related U.S. Application Data

(63) Continuation of application No. 11/777,962, filed on Jul. 13, 2007, now abandoned, which is a continuation-in-part of application No. 11/497,919, filed on Aug. 2, 2006.

(60) Provisional application No. 60/831,156, filed on Jul. 14, 2006.

(51) Int. Cl.
*C12Q 1/24* (2006.01)
*C12N 5/09* (2010.01)
*G01N 33/50* (2006.01)
*G01N 33/543* (2006.01)
*G01N 33/569* (2006.01)
*G01N 33/574* (2006.01)

(52) U.S. Cl.
CPC .......... *C12N 5/0693* (2013.01); *G01N 33/5094* (2013.01); *G01N 33/54346* (2013.01); *G01N 33/56972* (2013.01); *G01N 33/574* (2013.01); *G01N 2333/70525* (2013.01); *G01N 2333/70589* (2013.01); *G01N 2800/52* (2013.01)
USPC .................. 435/30; 435/4; 435/261; 435/6.13; 435/6.14; 435/366; 435/371; 435/7.23; 435/15; 435/34; 436/177

(58) Field of Classification Search
None
See application file for complete search history.

(56) References Cited

U.S. PATENT DOCUMENTS

| | | |
|---|---|---|
| 3,635,798 A | 1/1972 | Kirkham et al. |
| 3,975,156 A | 8/1976 | Kraft et al. |
| 4,326,934 A | 4/1982 | Pohl |
| 4,413,771 A | 11/1983 | Rohde et al. |
| 4,699,880 A | 10/1987 | Goldstein |
| 4,727,021 A | 2/1988 | Cote et al. |
| 4,786,387 A | 11/1988 | Whitlock |
| 4,828,991 A | 5/1989 | Hanna, Jr. et al. |
| 4,910,148 A | 3/1990 | Sorensen et al. |
| 5,264,554 A | 11/1993 | Newman |
| 5,288,614 A | 2/1994 | Bodenmuller et al. |
| 5,437,958 A | 8/1995 | Gallatin et al. |
| 5,437,987 A | 8/1995 | Teng et al. |
| 5,482,829 A | 1/1996 | Kass et al. |
| 5,532,139 A | 7/1996 | Miller |
| 5,541,072 A | 7/1996 | Wang et al. |
| 5,543,296 A | 8/1996 | Sobol et al. |
| 5,576,185 A | 11/1996 | Coulter et al. |
| 5,597,531 A | 1/1997 | Liberti et al. |
| 5,610,027 A | 3/1997 | Miller |
| 5,616,468 A | 4/1997 | Salmi et al. |
| 5,626,734 A | 5/1997 | Docoslis et al. |
| 5,629,162 A | 5/1997 | deFougerolles et al. |
| 5,641,628 A | 6/1997 | Bianchi |

(Continued)

FOREIGN PATENT DOCUMENTS

| CN | 1188528 C | 2/2005 |
|---|---|---|
| CN | 1880329 | 12/2006 |

(Continued)

OTHER PUBLICATIONS

Abrams et al., Cancer Detect Prev. (1994) 18(1):65-78.

(Continued)

*Primary Examiner* — Jim Ketter
(74) *Attorney, Agent, or Firm* — Morrison & Foerster LLP

(57) ABSTRACT

Provided are methods and compositions for isolating and detecting rare cells from a biological sample containing other types of cells, particularly including debulking that uses a microfabricated filter for filtering samples. The enriched rare cells can be used in a downstream process such as identification, characterization or growth in culture, or in other ways. Also included is a method of determining tumor aggressiveness or the number or proportion of cancer cells in the enriched sample by detecting telomerase activity, nucleic acid or expression after enrichment of rare cells. Also provided is an efficient, rapid method to specifically remove red and white blood cells from a biological sample containing at least one of the cell types, leading to enrichment of rare target cells including circulating tumor (CTC), stromal, mesenchymal, endothelial, fetal, stem, or non-hematopoietic cells et cetera from a blood sample.

8 Claims, 6 Drawing Sheets

(56) References Cited

U.S. PATENT DOCUMENTS

| | | |
|---|---|---|
| 5,646,004 A | 7/1997 | Van Vlasselaer |
| 5,653,859 A | 8/1997 | Parton et al. |
| 5,698,271 A | 12/1997 | Liberti et al. |
| 5,726,026 A | 3/1998 | Wilding et al. |
| 5,728,537 A | 3/1998 | Silen et al. |
| 5,766,888 A | 6/1998 | Sobol et al. |
| 5,786,224 A | 7/1998 | Li et al. |
| 5,814,200 A | 9/1998 | Pethig et al. |
| 5,837,115 A | 11/1998 | Austin et al. |
| 5,837,822 A | 11/1998 | Gallatin et al. |
| 5,840,490 A | 11/1998 | Bacchetti et al. |
| 5,866,071 A | 2/1999 | Leu |
| 5,869,262 A | 2/1999 | Gallatin et al. |
| 5,876,593 A | 3/1999 | Liberti et al. |
| 5,877,299 A | 3/1999 | Thomas et al. |
| 5,880,268 A | 3/1999 | Gallatin et al. |
| 5,883,760 A | 3/1999 | Yamada et al. |
| 5,888,370 A | 3/1999 | Becker et al. |
| 5,891,841 A | 4/1999 | deFougerolles et al. |
| 5,905,031 A | 5/1999 | Kuylen et al. |
| 5,922,278 A | 7/1999 | Chapman et al. |
| 5,928,880 A | 7/1999 | Wilding et al. |
| 5,948,278 A | 9/1999 | Sammons et al. |
| 5,993,630 A | 11/1999 | Becker et al. |
| 5,993,665 A | 11/1999 | Terstappen et al. |
| 6,040,176 A | 3/2000 | Gallatin et al. |
| 6,061,074 A | 5/2000 | Bartha et al. |
| 6,071,394 A | 6/2000 | Cheng et al. |
| 6,087,130 A | 7/2000 | Gallatin et al. |
| 6,117,985 A | 9/2000 | Thomas et al. |
| 6,184,043 B1 | 2/2001 | Fodstad et al. |
| 6,187,592 B1 | 2/2001 | Gourley |
| 6,190,870 B1 | 2/2001 | Schmitz et al. |
| 6,197,523 B1 | 3/2001 | Rimm et al. |
| 6,197,593 B1 | 3/2001 | Deka et al. |
| 6,228,652 B1 | 5/2001 | Rodriguez et al. |
| 6,235,534 B1 | 5/2001 | Brookes et al. |
| 6,265,229 B1 | 7/2001 | Fodstad et al. |
| 6,291,249 B1 | 9/2001 | Mahant et al. |
| 6,306,575 B1 | 10/2001 | Thomas et al. |
| 6,355,491 B1 | 3/2002 | Zhou et al. |
| 6,365,362 B1 | 4/2002 | Terstappen et al. |
| 6,482,926 B1 | 11/2002 | Thomas et al. |
| 6,491,918 B1 | 12/2002 | Thomas et al. |
| 6,551,843 B1 | 4/2003 | Rao et al. |
| 6,586,177 B1 | 7/2003 | Shuber |
| 6,596,143 B1 | 7/2003 | Wang et al. |
| 6,620,627 B1 | 9/2003 | Liberti et al. |
| 6,623,982 B1 | 9/2003 | Liberti et al. |
| 6,645,731 B2 | 11/2003 | Terstappen et al. |
| 6,673,541 B1 | 1/2004 | Klein et al. |
| 6,673,618 B1 | 1/2004 | Li et al. |
| 6,727,451 B1 | 4/2004 | Fuhr et al. |
| 6,818,743 B1 | 11/2004 | Gallatin et al. |
| 6,849,403 B1 | 2/2005 | Shuber |
| 6,881,314 B1 | 4/2005 | Wang et al. |
| 6,893,881 B1 | 5/2005 | Fodstad et al. |
| 6,900,029 B1 | 5/2005 | Coulter et al. |
| 6,919,174 B1 | 7/2005 | Shuber |
| 6,949,355 B2 | 9/2005 | Yamanishi et al. |
| 6,969,517 B2 | 11/2005 | Gillies et al. |
| 7,094,378 B1 | 8/2006 | Goodrich, Jr. et al. |
| 7,153,648 B2 | 12/2006 | Jing et al. |
| 7,166,443 B2 | 1/2007 | Walker et al. |
| 7,420,660 B2 | 9/2008 | Muller |
| 7,463,343 B2 | 12/2008 | Muller |
| 7,498,156 B2 | 3/2009 | Goodrich et al. |
| 7,771,658 B2 | 8/2010 | Larsen |
| 7,790,464 B2 | 9/2010 | Tarasev |
| 7,797,990 B2 | 9/2010 | Larsen et al. |
| 7,846,393 B2 | 12/2010 | Tai et al. |
| 7,846,743 B2 | 12/2010 | Tai et al. |
| 7,918,981 B2 | 4/2011 | Jing et al. |
| 8,114,289 B2 | 2/2012 | Zheng et al. |
| 8,227,250 B2 | 7/2012 | Larsen et al. |
| 8,268,244 B2 | 9/2012 | Tarasev et al. |
| 8,288,170 B2 | 10/2012 | Tai et al. |
| 8,426,122 B2 | 4/2013 | Parikh et al. |
| 8,492,686 B2 | 7/2013 | Bilchinsky et al. |
| 8,551,425 B2 | 10/2013 | Goldkorn et al. |
| 8,614,066 B2 | 12/2013 | Wu |
| 8,617,840 B2 | 12/2013 | Godfrin |
| 8,715,920 B2 | 5/2014 | Sehgal |
| 8,774,488 B2 | 7/2014 | Parikh et al. |
| 2001/0018192 A1 | 8/2001 | Terstappen et al. |
| 2001/0029293 A1 | 10/2001 | Gallatin et al. |
| 2002/0009759 A1 | 1/2002 | Terstappen et al. |
| 2002/0022276 A1 | 2/2002 | Zhou et al. |
| 2002/0058030 A1 | 5/2002 | Monroy et al. |
| 2002/0076825 A1 | 6/2002 | Cheng et al. |
| 2002/0122791 A1 | 9/2002 | Nicolette |
| 2002/0172987 A1 | 11/2002 | Terstappen et al. |
| 2003/0129676 A1 | 7/2003 | Terstappen et al. |
| 2003/0134305 A1 | 7/2003 | Dertinger et al. |
| 2003/0134416 A1 | 7/2003 | Yamanishi et al. |
| 2003/0147886 A1 | 8/2003 | Thomas et al. |
| 2003/0170631 A1 | 9/2003 | Houghton et al. |
| 2003/0199423 A1 | 10/2003 | Gallatin et al. |
| 2003/0203507 A1 | 10/2003 | Liberti et al. |
| 2004/0014104 A1 | 1/2004 | Shuber |
| 2004/0023222 A1 | 2/2004 | Russell et al. |
| 2004/0023288 A1 | 2/2004 | Ridder et al. |
| 2004/0029103 A1 | 2/2004 | Robinson et al. |
| 2004/0043467 A1 | 3/2004 | Shuber et al. |
| 2004/0072269 A1 | 4/2004 | Rao et al. |
| 2004/0142463 A1 | 7/2004 | Walker et al. |
| 2004/0248211 A1 | 12/2004 | Gallatin et al. |
| 2005/0158289 A1 | 7/2005 | Simmons et al. |
| 2005/0176020 A1 | 8/2005 | Gallatin et al. |
| 2005/0244404 A1 | 11/2005 | Sumitran-Holgersson et al. |
| 2005/0260766 A1 | 11/2005 | Paul et al. |
| 2006/0008807 A1 | 1/2006 | O'Hara et al. |
| 2006/0014174 A1 | 1/2006 | Georgakopoulos |
| 2006/0252054 A1 | 11/2006 | Lin et al. |
| 2006/0254972 A1 | 11/2006 | Tai et al. |
| 2007/0025883 A1 | 2/2007 | Tai et al. |
| 2008/0057505 A1 | 3/2008 | Lin et al. |
| 2008/0206757 A1 | 8/2008 | Lin et al. |
| 2009/0188864 A1 | 7/2009 | Zheng et al. |
| 2010/0159506 A1 | 6/2010 | Parikh et al. |
| 2010/0181288 A1 | 7/2010 | Tang et al. |
| 2010/0248257 A1 | 9/2010 | Jacobsen et al. |
| 2010/0273168 A1 | 10/2010 | Krockenberger et al. |
| 2010/0279322 A1 | 11/2010 | Tang et al. |
| 2011/0053052 A1 | 3/2011 | Braun et al. |
| 2011/0111412 A1 | 5/2011 | Tai et al. |
| 2011/0275064 A1 | 11/2011 | Wu et al. |
| 2011/0294206 A1 | 12/2011 | Tai et al. |
| 2012/0021453 A1 | 1/2012 | Patra et al. |
| 2012/0097610 A1 | 4/2012 | Zheng et al. |
| 2012/0178097 A1 | 7/2012 | Tai et al. |
| 2012/0183946 A1 | 7/2012 | Tang et al. |
| 2012/0282598 A1 | 11/2012 | Wu et al. |
| 2012/0282599 A1 | 11/2012 | Wu et al. |
| 2013/0059308 A1 | 3/2013 | Makarova et al. |
| 2013/0130930 A1 | 5/2013 | Parikh et al. |
| 2013/0144399 A1 | 6/2013 | Tai et al. |
| 2013/0164740 A1 | 6/2013 | Wu et al. |
| 2013/0344480 A1 | 12/2013 | Takagi |
| 2014/0080149 A1 | 3/2014 | Goehde |
| 2014/0154797 A1 | 6/2014 | Godfrin |

FOREIGN PATENT DOCUMENTS

| | | |
|---|---|---|
| CN | 1880473 | 12/2006 |
| CN | 101576557 | 11/2009 |
| CN | 101650370 | 2/2010 |
| CN | 102401761 | 4/2012 |
| WO | WO-92/22323 | 12/1992 |
| WO | WO-93/14776 | 8/1993 |
| WO | WO-94/16821 | 8/1994 |
| WO | WO-94/17011 | 8/1994 |
| WO | WO-94/17100 | 8/1994 |
| WO | WO-96/14578 | 5/1996 |

(56) References Cited

FOREIGN PATENT DOCUMENTS

| | | |
|---|---|---|
| WO | WO-96/27420 | 9/1996 |
| WO | WO-97/08557 | 3/1997 |
| WO | WO-97/35589 | 10/1997 |
| WO | WO-99/41613 | 8/1999 |
| WO | WO-99/52640 | 10/1999 |
| WO | WO-99/62622 | 12/1999 |
| WO | WO-01/42502 | 6/2001 |
| WO | WO-02/12896 | 2/2002 |
| WO | WO-02/16647 | 2/2002 |
| WO | WO-02/27909 | 4/2002 |
| WO | WO-02/28523 | 4/2002 |
| WO | WO-02/29400 | 4/2002 |
| WO | WO-02/30562 | 4/2002 |
| WO | WO-02/31505 | 4/2002 |
| WO | WO-02/31506 | 4/2002 |
| WO | WO-02/077269 | 10/2002 |
| WO | WO-03/018757 | 3/2003 |
| WO | WO-03/031938 | 4/2003 |
| WO | WO-03/035894 | 5/2003 |
| WO | WO-03/065042 | 8/2003 |
| WO | WO-2004/011941 | 2/2004 |
| WO | WO-2004/076643 | 9/2004 |
| WO | WO-2005/028663 | 3/2005 |
| WO | WO-2005/047529 | 5/2005 |
| WO | WO-2006/041453 | 4/2006 |
| WO | WO-2006/116327 | 11/2006 |
| WO | WO-2009/097247 | 8/2009 |
| WO | WO-2010/085337 | 7/2010 |
| WO | WO-2010/135603 | 11/2010 |
| WO | WO-2011/139445 | 11/2011 |
| WO | WO-2011/150357 | 12/2011 |
| WO | WO-2013/078409 | 5/2013 |
| WO | WO-2013/088131 | 6/2013 |
| WO | WO-2013/181285 | 12/2013 |

OTHER PUBLICATIONS

Becker et al., PNAS (1995) 92:860-864.
Blanco et al., Oncogene (2002) 21(20):3241-3246.
Carlson et al., Am J. Clin Pathol. (2003) 120(Suppl):S101-S127.
Dhar et al., Lab Invest. (2003) 83(9):1343-1352.
Diala et al., J. Natl. Cancer Inst. (1983) 71(4):755-764.
El Hilali et al., Clin Cancer Res. (2005) 11(3):1253-1258.
Feldstein and Zelen, Breast Cancer Res Treat. (1984) 4(1):3-10.
Frost et al., Cancer Metastasis. Rev. (1983) 2(4):375-378.
Fuhr et al., Sensors and Materials (1995) 7:131-146.
Griwatz et al., Journal of Immunological Methods (1995) 183:251-265.
Huang et al., J. Phys. D: Appl Phys. (1993) 26:1528-1535.
Itoh et al., Clin Cancer Res. (2004) 10(8):2812-2817.
Li et al., Neoplasia. (2005) 7(12):1073-1080.
Muller et al., Clin Cancer Res. (2005) 11(10):3678-3685.
Rao et al., J. Clin Invest. (2002) 110(3):351-360.
Senie et al., Cancer (1994) 73(6):1666-1672.
Singleton and Sainbury, Dictionary of Microbiology and Molecular Biology, 3rd ed., pp. 557-560, (2006).
Wakabayashi et al., Cancer (1995) 75(12):2827-2835.
Wang et al., Biochim Biophys Acta (1995) 1243:185-194.
Wang et al., Biophys J. (1997) 72:1887-1899.
Wang et al., IEEE Transaction on Industry Applications (1997) 33(3):660-669.
Weber et al., Nature Genetics (2005) 37(8):853-862.
Yang et al., J. Biol Chem. (2006) 281(14):9719-9727.
International Search Report and Written Opinion for PCT/US07/16034, mailed Aug. 19, 2008, 5 pages.
Supplementary European Search Report for EP Application No. 07796848.5, mailed on Dec. 11, 2009, 8 pages.
Albelda et al., Journal of Cell Biology (1990) 110:1227-1237.
Allgayer et al., Journal of Histochemistry & Cytochemistry (1997) 45(2):203-212.
Berois et al., Anticancer Res. (1997) 17:2639-2646.
Bilkenroth et al., Int. J. Cancer (2001) 92:577-582.
Chiaramonte et al., J. Immunol. (1999) 162(2):920-930.
Choy et al., Br. J. Surg. (1993) 80(11):1490.
Cohn et al., Bone Marrow Transplant. (1997) 20(7):543-551.
Cooper et al., Laboratory Investigation (1985) 52(3):243-256.
Cote et al., J. Clinical Oncology (1991) 9(10):1749-1756.
Defougerolles and Springer, J. Exp. Med. (1992) 175:185-190.
Defougerolles et al., J. Exp. Med. (1993) 177:1187-1192.
Defougerolles et al., J. Exp. Med. (1994) 179:619-629.
Fidler, Cancer Research (1990) 50:6130-6138.
Ghossein et al., 1996 ASCO Annual Meeting, abstract 647.
Glaves, Br. J. Cancer (1983) 48:665-673.
Gross et al., PNAS USA (1995) 92:537-541.
Haber et al., 1996 ASCO Annual Meeting, abstract 1442.
Hagedorn et al., Journal of Electrostatics (1994) 33:159-185.
Hamdy et al., Br. J. Urol. (1992) 69:392-396.
Hardingham et al., Cancer Research (1993) 53(15):3455-3458.
Hasegawa and Yosioka, J. Acoust. Soc. Am.(1969) 46:1139-1143.
Helfrich et al., British Journal of Cancer (1997) 76:29-35.
Iinuma et al., Int. J. Cancer (2000) 89:337-344.
Johnson et al., British J. Cancer (1995) 72:268-276.
Juan et al., Allergy (1999) 54:1293-1298.
Juan et al., Eur. J. Immunol. (1993) 23:1508-1512.
Klickstein et al., Journal of Biological Chemistry (1996) 271(39):23920-23927.
Komeda et al., Cancer (1995) 75(9):2214-2219.
Kvalheim, Acta Oncologica (1996) 35(Supp. 8):13-18.
Larsson et al., Molecular Diagnosis (2001) 6:181-188.
Laver et al., Cancer Research Therapy and Control (1999) 9:25-30.
Leather et al., Br. J. Surg. (1993) 80(6):777-780.
Lindemann et al., Lancet (1992) 340(8821):685-9 (abstract only).
Louha et al., Hepatology (1997) 26(4):998-1005.
Makarovskiy et al., J. Clin. Lab. Anal. (1997) 11:346-350.
Mattano et al., Cancer Res. (1992) 52:4701-4705.
McHugh et al., Eur. J. Immunol. (2001) 31:2094-2103.
Mellado et al., Clin. Cancer Res. (1999) 5(7):1843-1848.
Meye et al., Int. J. Oncol. (2002) 21(3):521-530.
Molino et al., Cancer (1991) 67:1033-1036.
Mortada et al., C.R. Acad. Sci. Paris (1990) t. 311, Serie III, p. 63-68.
Moss and Sanders, Journal of Clinical Oncology (1990) 8(4):736-740.
Moss et al., Program/Proceedings American Society of Clinical Oncology, Thirty-Third Annual Meeting May 17-20, 1997, vol. 16, p. 90a, abstract 317.
Moss et al., The New England Journal of Medicine (1991) 324(4):219-226.
Muirhead et al., Ann. NY Acad. Sci. (1986) 468:113-127.
Nakamori et al., Dis. Colon Rectum (1997) 40(10):S29-S36.
Nuclepore track etched-membranes at http://www.whatman.com/products/?pageID=7.57.291.22, visited Dec. 13, 2005.
Pantel, Progress in Histochemistry and Cytochemistry (1996) 30(3):1-60.
Perez et al., J. Immunol. (1989) 142:3662-3667.
Racila et al., PNAS USA (1998) 95:4589-4594.
Rooney, "Nonlinear phenomena," in Methods of Experimental Physics: Ultrasonics, Edmonds (ed.) Academic Press (1981) Chapter 6.4 pp. 319-327.
Ross et al., Blood (1993) 82(9):2605-2610.
Salsbury, Cancer Treatment Reviews (1975) 2:55-72.
Sanders and Moss, Cancer (1991) 67:1423-1427.
Schlimok et al., Journal of Clinical Oncology (1990) 8:831-837 (abstract only).
Schwartzberg et al., Program/Proceedings American Society of Clinical Oncology, Thirty-Third Annual Meeting May 17-20, 1997, vol. 16, p. 118a, abstract 416.
Seeger et al., J. Clin. Oncol. (2000) 18(24):4067-4076.
Sewchand and Canham, Can. J. Physiol. Pharmacol. (1979) 57(11):1213-1222.
Simon et al., PNAS USA (1990) 78:2755-2759.
Smith et al., J. Clin. Oncol. (2000) 18(7):1432-1439.
Smith et al., Lancet (1991) 338(16):1227-1229.
Staunton et al., Cell (1990) 61:243-254.
Umiel et al., 1999 ASCO Annual Meeting, abstract 1215.
Umiel et al., Proc. Am. Soc. Clin. Oncol. (1999) 18:316a.

(56) References Cited

OTHER PUBLICATIONS

Vazeux et al., Nature (1992) 360:485-488.
Vilella et al., Tissue Antigens (1990) 36:203-210.
White et al., Proc. R. Soc. Med. (1976) 69:467-469.
Wisniewski et al., Leukemia Research (1991) 15(9):867-874.
Wong et al., J. Surgery (1995) 82:1333-1337.
Yasuda et al., Jpn. J. Appl. Phys. (1996) 35:3295-3299.
Yosioka and Kawasima, Acustica (1955) 5:167-173.
International Search Report for PCT/US04/030359, mailed on Jan. 5, 2005, 1 page.
Response to Notice to File Missing Parts of Nonprovisional Application and Preliminary Amendment from U.S. Appl. No. 11/264,413, filed Jul. 10, 2006.
Restriction Requirement from U.S. Appl. No. 11/264,413, mailed on Dec. 13, 2007.
Response to Restriction Requirement from U.S. Appl. No. 11/264,413, filed Jan. 10, 2008.
Non-Final Office Action from U.S. Appl. No. 11/264,413, mailed on Mar. 6, 2009.
Amendment in Response to Non-Final Office Action from U.S. Appl. No. 11/264,413, filed Jul. 30, 2009.
Final Office Action from U.S. Appl. No. 11/264,413, mailed on Dec. 10, 2009.
Amendment After Final Action Under 37 C.F.R. 1.116 from U.S. Appl. No. 11/264,413, filed Feb. 12, 2010.
Non-Final Office Action from U.S. Appl. No. 11/264,413, mailed on Jun. 11, 2010.
Amendment Under 37 C.F.R. § 1.111 from U.S. Appl. No. 11/264,413, filed Dec. 13, 2010.
Restriction Requirement from U.S. Appl. No. 11/777,962, mailed on Sep. 10, 2008.
Amendment in Response to Non-Final Office Action Restriction Requirement from U.S. Appl. No. 11/777,962, filed Oct. 6, 2008.
Non-Final Office Action from U.S. Appl. No. 11/777,962, mailed on Dec. 11, 2008.
Amendment in Response to Non-Final Office Action from U.S. Appl. No. 11/777,962, filed Apr. 13, 2009.
Non-Final Office Action from U.S. Appl. No. 11/777,962, mailed on Jul. 17, 2009.
Amendment in Response to Non-Final Office Action from U.S. Appl. No. 11/777,962, filed Jan. 19, 2010.
Interview Summary from U.S. Appl. No. 11/777,962, filed Feb. 1, 2010.
Non-Final Office Action from U.S. Appl. No. 11/777,962, mailed on Apr. 29, 2010.
Adkins et al., J. Peds. Surg. (2004) 39:931-936.
Ellis et al., J. Urol. (1998) 159(4):1134-1138.
Faulkner et al., J. Hematother. (1998) 7(4):361-366.
Franklin et al., Breast Cancer Res. Treat. (1996) 41(1):1-13.
Gluck et al., Biol. Blood Marrow Transplant. (1997) 3(6):316-323.
Matthay et al., J. Clin. Oncol. (1993) 11(11):2226-2233.
Mori et al., J. Clin. Oncol. (1998) 16:128-132.
Naito, Hokkaido Igaku Zasshi (1991) 66(2):135-141.
Naito et al., Eur. J. Cancer (1991) 27(6):762-765.
Pecora et al., Biol. Blood Marrow Transplant. (2002) 8(10):536-543.
Pecora et al., Blood (1999) 94(Supp. 1):665a.
Villa et al., Gastroenterology (1996) 10:1346-1353.
Ahn et al., IEEE Trans. Magnetics (1994) 30:73-79.
Ahn et al., J. Microelectromechanical Systems (1996) 5:151-158.
Collins, Journal of Immunological Methods (2000) 243:125-145.
De Gasperis et al., Meas. Sci. Technol. (1998) 9:518-529.
Decoslis et al., Biotechnology and Bioengineering (1997) 54(3):239-250.
Gazdar et al., J. Natl. Cancer Inst. (1999) 91:299-301.
Huang et al., Biochim. Biophys. Acta. (1996) 1282:76-84.
Huang et al., Biochim. Biophys. Acta. (1999) 1417:51-56.
Huang et al., J. Hematotherapy and Stem Cell Research (1999) 8:481-490.
Huang et al., Phys. Med. Biol. (1992) 37:1499-1517.
Liakopoulos et al., Transducers 97, pp. 484-488, presented in 1997 International Conference on Solid State Sensors and Actuators, Chicago, Jun. 16, 1997.
Miller, Pediatric Cardiology (1999) 20(4):287-289.
Ogura et al., IEEE Trans. On Biomedical Engineering (1991) 38(8):721-726.
Pui et al., Biotachno. Prog. (1995) 11:146-152.
Safarik and Safarikova, J. of Chromatography (1999) 722(B):33-53.
Wang et al., Biophysical Journal (1998) 74:2689-2701.
Wu, J. Acoust. Soc. Am. (1991) 89:2140-2143.
Wu and Du, J. Acoust. Soc. Am. (1990) 87:997-1003.
Yang et al., Biophys. J. (1999) 76:3307-3314.
Yasuda et al., J. Acoust. Soc. Am. (1996) 99(2):1248-1251.
Yasuda et al., J. Acoust. Soc. Am. (1996) 99(4):1965-1970.
Yasuda et al., J. Acoust. Soc. Am. (1997) 102(1):642-645.
Yasuda and Kamakura, Appl. Phys. Lett. (1997) 71(13):1771-1773.
U.S. Appl. No. 10/268,312, filed Oct. 10, 2002.
Non-Final Office Action for U.S. Appl. No. 10/268,312, date mailed on Jun. 1, 2004.
Response to Office Action for U.S. Appl. No. 10/268,312, filed Sep. 1, 2004.
Response to Non-Compliant Amendment for U.S. Appl. No. 10/268,312, filed Feb. 1, 2005.
Notice of Allowance for U.S. Appl. No. 10/268,312, date mailed on Mar. 10, 2005.
Notice of Drawing Inconsistency with Specification for U.S. Appl. No. 10/268,312, date mailed on Jul. 28, 2005.
Response to Office Communication for U.S. Appl. No. 10/268,312, filed Aug. 9, 2005.
U.S. Appl. No. 10/701,684, filed Nov. 4, 2003.
Non-Final Office Action for U.S. Appl. No. 10/701,684, date mailed on Nov. 15, 2005.
Response to Office Action for U.S. Appl. No. 10/701,684, filed Jan. 13, 2006.
Notice of Allowance and Examiner's Amendment for U.S. Appl. No. 10/701,684, dated Mar. 22, 2006.
Notice of Allowance for U.S. Appl. No. 10/701,684, date mailed on Aug. 10, 2006.
European Office Action for Application No. 02801051.0, date mailed on Sep. 15, 2006.
Response to European Office Action for Application No. 02801051.0, filed on Mar. 23, 2007.
European Office Action for Application No. 02801051.0, date mailed Apr. 26, 2007.
Response to European Office Action for Application No. 02801051.0, filed on Oct. 19, 2007.
European Office Action for Application No. 02801051.0, date mailed on Nov. 7, 2007.
Supplemental European Search Report for EP 04784274.5, mailed Aug. 7, 2008, 7 pages.
Agouron Meeting Agenda, Jul. 13, 1998, 1 page.
Ancell Immunology Research Products, anti-human CD50 (ICAM-3), retrieved from http://www.ancell.com/html/anti-cd50_icam-3_.html, retrieved on Apr. 17, 2006.
BIS Laboratories, "Breast Carcinoma Assay" marketing piece (1996).
BIS' Biopharmaceutical Strategy—Surrogate Marker for Clinical Efficacy, Jul. 16, 1998, 2 pages.
Diab et al., "Bone Marrow and/or Peripheral Blood Micrometastases as Prognostic Factors in Breast Cancer Patients.", Protocol written in early 1998 or late 1987.
Documentation of Meeting with Sue Cohn, Oct. 19, 1996, 1 page.
ICAM3, retrieved from http://www.ihop-net.org/UniPub/iHOP/gs/89280.html, retrieved on Apr. 13, 2006.
ICAM3 antibody [101-1 D2] (ab23597) datasheet, retrieved from http://www.abcam.com/index.html?datasheet=23597, date retrieved Apr. 17, 2006.
Kletzel et al., J. Clin. Oncol. (2002) 20(9):2284-2292.
Moss, Letter from Thomas J. Moss, M.D. to Board of Directors; ISHAGE, Aug. 21, 1994, 2 pages.
Moss, Letter from Thomas J. Moss, M.D. to Morris Kletzel, M.D., Dec. 1, 1992, 1 page.

(56) References Cited

OTHER PUBLICATIONS

Moss, Letter from Thomas J. Moss, M.D. to Morris Kletzel, M.D., Jun. 11, 1993, 1 page.
Moss, Letter from Tom Moss to Charles Weaver, M.D., Nov. 4, 1996, 1 page.
Moss, Letter from Thomas J. Moss, M.D. to Victor M. Santana, M.D., Feb. 15, 1992, 2 pages.
Moss, Invitation to participate as a speaker at symposium from Thomas J. Moss, M.D. to J. Graham Sharp, Oct. 24, 1995, 2 pages.
Moss, Letter from Thomas J. Moss, M.D. to Susan Kreissman, M.D., Nov. 29, 1993, 1 page.
Moss, Meeting Report: $1^{st}$ International Meeting on Minimal Residual Cancer, written Aug. 1996, following Jun. 1996 meeting, 2 pages.
Pantel and Moss, Meeting Report: $1^{st}$ International Meeting on Minimal Residual Cancer, conference held Jun. 23-25, 1996.
Siegel, Letter from Marc D. Siegel to Herbert Lazarus, Ph.D., Sep. 20, 1995, 2 pages.
Notice of Allowance for U.S. Appl. No. 11/264,413, mailed Jun. 3, 2013, 6 pages.
Ex Parte Quayle Action for U.S. Appl. No. 11/497,919, mailed Jun. 4, 2013, 4 pages.
Request for Continued Examination for U.S. Appl. No. 11/497,919, filed Jun. 10, 2013, 7 pages.
Notice of Allowance fro U.S. Appl. No. 11/497,919, mailed Jun. 28, 2013, 6 pages.
Supplementary Partial European Search Report for EP 02 72 8540, mailed on Apr. 4, 2005, 7 pages.
Notice of Reasons for Rejection for Japanese Patent Application No. 2005-310561, mailed on Jul. 6, 2009, 3 pages.
Office Action for Japanese Patent Application No. 2002-575311, mailed Oct. 4, 2007.
Office Action for U.S. Appl. No. 10/103,581, mailed Aug. 18, 2004.
Response to Office Action for U.S. Appl. No. 10/103,581, mailed Dec. 20, 2004.
Final Office Action for U.S. Appl. No. 10/103,581, mailed Mar. 22, 2005.
Response after Final Office Action for U.S. Appl. No. 10/103,581, mailed Jun. 27, 2005.
Advisory Action for U.S. Appl. No. 10/103,581, mailed Jul. 14, 2005.
Office Action for U.S. Appl. No. 10/103,581, mailed Sep. 29, 2005.
Response to Office Action for U.S. Appl. No. 10/103,581, mailed Dec. 29, 2005.
Notice of Allowance and Examiner Interview Summary for U.S. Appl. No. 10/103,581, mailed Mar. 20, 2006.
RCE and Amendment for U.S. Appl. No. 10/103,581, mailed Jun. 20, 2006.
Notice of Allowance and Examiner+s Amendment for U.S. Appl. No. 10/103,581, mailed Jul. 25, 2006.
Supplemental Notice of Allowance and Examiner's Amendment for U.S. Appl. No. 10/103,581, mailed Oct. 17, 2006.
Substance of Interview for U.S. Appl. No. 10/103,581, mailed Nov. 17, 2006.
Examiner Interview Summary for U.S. Appl. No. 11/598,848, mailed Jan. 27, 2010.
Office Action for U.S. Appl. No. 11/598,848, mailed Feb. 5, 2010.
Substance of Interview for U.S. Appl. No. 11/598,848, mailed Feb. 23, 2010.
Response to Office Action for U.S. Appl. No. 11/598,848, mailed Jul. 6, 2010.
Final Office Action for U.S. Appl. No. 11/598,848, mailed Oct. 14, 2010.
Response after Final Office Action for U.S. Appl. No. 11/598,848, mailed Dec. 13, 2010.
Notice of Allowance for U.S. Appl. No. 11/598,848, mailed Dec. 27, 2010.
International Preliminary Examination Report for International Patent Applcation No. PCT/US02/08880, mailed Jun. 25, 2003.
Becker et al., "Separation of Human Breast Cancer Cells from Blood by Differential Dielectric Affinity," Proc. Natl. Acad. Sci. USA (1995) 29:860-864.
Bianchi et al., "Isolation of Fetal DNA from Nucleated Erythrocytes in Maternala Blood," Proc. Natl. Acad. Sci. USA (1990) 86:3279-3283.
Chan et al., "Measurements of the Dielectric Properties of Peripheral Blood Mononuclear Cells and Trophoblast Cells using AC Electrokinetic Techniques," Biochimica et Biophysica Acta (2000) 1500(3):131-32.
Cheng et al., "Isolation of Cultured Cervical Carcinoma Cells Mixed with Peripheral Blood Cells on a Bioelectronic Chip," Anal. Chem. (1998) 70(11):2321-2326.
Cheng et al., "Preparation and Hybridization Analysis of DNA/RNA from *E. coli* on Microfabricated Bioelectronic Chips," Nature Biotechnology (1998) 16(6):541-546.
Cheung et al., "Prenatal Diagnosis of Sickle Cell Anaemia and Thalassaemia by Analysis of Fetal Cells in Maternal Blood," Nature Genetics (1996) 14:264-268.
Fuhr et al., "Positioning and Manipulation of Cells and Microparticles Using Miniaturized Electric Field Traps and Travelling Waves," Sensors and Materials (1995) 7:131-146.
Holzgreve et al., "Fetal Cells in the Maternal Circulation," Journal of Reproductive Medicine (1992) 37(5):410-418.
Huang et al., "Membrane Changes Associated with the Temperature-Sensitive $P85^{gag-mos}$ dependant Transformation of Rat Kidney Cells as Determined by Dielectrophoresis and Electrorotation," Biochim. Biophys. Acta (1996) 1282:76-84.
Huang et al., "Introducing Dielectrophoresis as a New Force Field for Field-Flow Fractionation," Biophysical Journal (1997) 73:1118-1129.
Huang et al., "Electrokinetic Behaviour of Colloidal Particles in Travelling Electric Fields: Studies Using Yeast Cells," J. Phys. D. Appl. Phys. (1993) 26:1528-1535.
Hughes et al., "Dielectrophoretic Forces on Particles in Travelling Electric Fields," J. Phys. Appl. Phys. (1997) 29:474-482.
Kuo and Guo, "Nucleated Red Blood Cells in Maternal Blood During Pregnancy," Obstetrics and Gynecology (1999) 94(3):464-468.
Markx et al., "Separation of Viable and Non-viable Yeast Using Dielectrophoresis," Journal of Biotechnology (1994) 32:29-37.
Mavrou et al., "Fetal Cells in Maternal Blood: Isolation by Magnetic Cell Sorting and Confirmation by Immunophenotyping and FISH," In Vivo (1998) 12(2):195-200.
Merriam-Webster Online Dictionary, (2004) www.m-w.com, accessed Jul. 28, 2004.
Miale, "Laboratory Medicine: Hematology," (1972) C.V. Mosby Company, $4_{th}$ Ed., pp.1208-120.9.
Muller,"A 3-D Microelectrode System for Handling and Caging Single Cells and Particles," Biosensors & Bioelectronics (1999) 14:247-256.
Pethig, "Dielectrophoresis: Using Inhomogeneous AC Electrical Fields to Separate and Manipulate Cells," Critical Reviews in Biotechnology (1996) 16(4):331-348.
Shafer et al., "Preparation of Interpretation of Peripheral Blood Smears," Hematology: Basic Principles and Practice, (1995) Churchill Livingstone, Hoffman et al. (eds.), $2^{nd}$ Ed., pp. 2202-2209.
Simpson and Elias, "Isolating Fetal Cells in Maternal Circulation for Prenatal Diagnosis," Prenatal Diagnosis (1994) 14:1229-1242.
Talary et al., "Electromanipulation and Separation of Cells Using Travelling Electric Fields," J. Phys. D: Appl. Phys. (1996) 29:2198-2203.
Wang et al., "Non-uniform Spatial Distributions of Both the Magnitude and Phase of AC Electric Fields Determine Dielectrophoretic Forces," Biochim. Biophys. Acta (1995) 1243:185-194.
Wang et al., "Dielectrophoretic Manipulation of Cells with Spiral Electrodes," Biophys. J. (1997) 72:1887-1899.
Wang et al., "A Unified Theory of Dielectrophoresis and Travelling Wave Dielectrophoresis," J. Phys. D. Appl. Phys. (1994) 27:1571-1574.
Williamson, "Towards Non-invasive Prenatal Diagnosis," Nature Genetics (1996) 14:239-240.
Communication pursuant to Article 94(3) EPC, mailed Jul. 8, 2013, 6 pages.

(56) References Cited

OTHER PUBLICATIONS

Adams et al., "Rapid and Efficient Isolation of Circulating Tumor Cells from Whole Blood Using High Porosity Precision Microfilters," Creatv MicroTech, Inc., presented at 7th Early Detection Research Network (EDRN) Scientific Workshop, Herndon, VA, Sep. 13-16, 2011, 1 page.
Chen et al., "Microfluidic Chip for Blood Cell Separation and Collection Based on Crossflow Filtration," Sensors and Actuators B 130 (2008) 216-221.
Lu et al., "Parylene Membrane Slot Filter for the Capture, Analysis and Culture of Viable Circulating Tumor Cells," California Institute of Technology, downloaded on Jul. 12, 2010 from IEEE Xplore, pp. 935-938.
Office Action for Taiwanese Patent Application No. 091105474, dated May 14, 2004.
Response to Office Action for Taiwanese Patent Application No. 091105474, dated Oct. 21, 2004.
Office Action for Taiwanese Patent Application No. 091105474, dated Sep. 27, 2009.
Response to Office Action for Taiwanese Patent Application No. 091105474, dated Dec. 1, 2009.
Office Action for Australian Patent Application No. 2007205731, dated Oct. 30, 2007.
Response to Office Action for Australian Patent Application No. 2007205731, dated Nov. 14, 2007.
Office Action for Australian Patent Application No. 2007205731, dated Nov. 26, 2007.
Response to Office Action for Australian Patent Application No. 2007205731, dated Sep. 11, 2008.
Acceptance for Australian Patent Application No. 2007205731, dated Sep. 18, 2008.
Office Action for Canadian Patent Application No. 2,440,385, dated Dec. 1, 2009.
Response to Office Action for Canadian Patent Application No. 2,440,385, dated Jun. 1, 2010.
Office Action for Canadian Patent Application No. 2,440,385, dated Dec. 15, 2010.
Response to Office Action for Canadian Patent Application No. 2,440,385, dated Jun. 15, 2011.
Communication for European Patent Application No. 02728540.2, dated May 22, 2006.
Response to Communication for European Patent Application No. 02728540.2, dated Sep. 25, 2006.
Communication for European Patent Application No. 02728540.2, dated Apr. 12, 2007.
Response to Communication for European Patent Application No. 02728540.2, dated Aug. 20, 2007.
Communication for European Patent Application No. 02728540.2, dated Dec. 18, 2008.
Response to Communication for European Patent Application No. 02728540.2, dated Apr. 28, 2009.
Communication for European Patent Application No. 02728540.2, dated Oct. 28, 2009.
Reply to Communication for European Patent Application No. 02728540.2, dated Mar. 5, 2010.
Decision to Grant for European Patent Application No. 02728540.2, dated Apr. 1, 2010.
Office Action for Japanese Patent Application No. 2002-575311, dated Apr. 26, 2005.
Response to Office Action for Japanese Patent Application No. 2002-575311, dated Oct. 25, 2005.
Final Office Action for Japanese Patent Application No. 2002-575311, dated Oct. 2, 2007.
Office Action for Japanese Patent Application No. 2005-310561, dated Sep. 29, 2008.
Response to Office Action for Japanese Patent Application No. 2005-310561, dated Dec. 26, 2008.
Office Action for Japanese Patent Application No. 2005-310561, dated Jul. 2, 2009.
Response to Office Action for Japanese Patent Application No. 2005-310561, dated Oct. 5, 2009.
Notice of Allowance for Japanese Patent Application No. 2005-310561, dated Oct. 27, 2009.
Office Action for Australian Patent Application No. 2002258585, dated Apr. 21, 2006.
Response to Office Action for Australian Patent Application No. 2002258585, dated Apr. 16, 2007.
Notice of Acceptance for Australian Patent Application No. 2002258585, dated Apr. 24, 2007.
Partial Search Report for European Patent Application No. 09007354.5, dated Sep. 3, 2009.
Extended Search Report for European Patent Application No. 09007354.5, dated Dec. 22, 2009.
Communication for European Patent Application No. 09007354.5, dated Apr. 6, 2010.
Response to Communication for European Patent Application No. 09007354.5, dated Aug. 16, 2010.
Communication for European Patent Application No. 09007354.5, dated Aug. 2, 2011.
Response to Communication for European Patent Application No. 09007354.5, dated Dec. 12, 2011.
Communication for European Patent Application No. 09007354.5, dated Dec. 14, 2012.
Response to Communication for European Patent Application No. 09007354.5, dated May 21, 2013.
Letter Accompanying Subsequently Filed Items for European Patent Application No. 09007354.5, dated Jun. 7, 2013.
Result of Consultation for European Patent Application No. 09007354.5, dated Jun. 18, 2013.
Communication of Intent to Grant for European Patent Application No. 09007354.5, dated Jun. 28, 2013.
Office Action for CA 2,462,914, mailed Dec. 9, 2013, 3 pages.
Office Action for U.S. Appl. No. 14/027,044, mailed Jan. 9, 2014, 4 pages.
Office Action for U.S. Appl. No. 14/029,598, mailed Jan. 10, 2014, 6 pages.
Response to Communication pursuant to Article 94(3) EPC for EP 04784274.5, filed Jan. 17, 2014, 126 pages.
Aversa et al., "A Monoclonal Antibody (A6) Recognizing a Unique Epitope Restricted to CD45RO and RB Isoforms of the Leukocyte Common Antigen Family Identifies Functional T Cell Subsets," Cellular Immunology (1994) 158:314-328.
Cytelligen Trademark, registration No. 4436018, registered Nov. 19, 2013.
Dahlke et al., "In vivo depletion of hematopoietic stem cells in the rat by an anti-CD45 (RT7) antibody," Blood (2002) 99(10): 12 pages.
iFISH Trademark, registration No. 4494597, registered Mar. 11, 2014.
Lara et al., "Enrichment of rare cancer cells through depletion of normal cells using density and flow-through, immunomagnetic cell separation," Experimental Hematology (2004) 32:891-904.
Lin et al., "Calnuc plays a role in dynamic distribution of Gαi but not Gβ subunits and modulates ACTH secretion in AtT-20 neuroendocrine secretory cells," Molecular Neurodegeneration (2009) 4:15, 16 pages.
New Products, Science Magazine (Jul. 26, 2013) 341(6144):415, 2 pages.
Ran et al., "Determination of EGFR mutations in single cells microdissected from enriched lung tumor cells in peripheral blood," Analytical and Bioanalytical Chemistry (2013) 405(23):7377-7382 (Abstract).
Scott et al., "Effect of Osmotic Lysis and Resealing on Red Cell Structure and Function," The Journal of Laboratory and Clinical Medicine (1990) 115(4):470-480.
Tanaka et al., "Circulating tumor cells (CTCs) in lung cancer: current status and future perspectives," Lung Cancer: Targets and Therapy (2010) 1:77-84.
Vona et al., "Technical Advance: Isolation by Size of Epithelial Tumor Cells," American Journal of Pathology (2000) 156(1):57-63.
Wu et al., "Preliminary Investigation of the Clinical Significance of Detecting Circulating Tumor Cells Enriched from Lung Cancer Patients," Journal of Thoracic Oncology (2009) 4(1):30-36.

(56) References Cited

OTHER PUBLICATIONS

Xing and Wang, "Clinical Validation of an Enrichment and Identification Method of Circulating Tumor Cells in Breast Cancer Patients," Science and Technology Review (2012) 30(21):56-60 (English abstract included).

Notice of Allowance for U.S. Appl. No. 14/027,044, mailed Jul. 2, 2014, 6 pages.

Request for Reinstatement and Response to Examiner's for CA 2,544,564, filed Jul. 14, 2014, 66 pages.

Notice of Allowance for U.S. Appl. No. 11/497,919, mailed Jul. 17, 2014, 5 pages.

Notice of Allowance for U.S. Appl. No. 11/264,413, mailed Jul. 18, 2014, 5 pages.

Changes of CTC count before and after chemotherapy (4-6 weeks) correlates with clinical response assessed by CT scan. Response assessment by the RECIST criteria. PD: progressive disease; SD: stable disease; PR: Partial response.

METHODS AND COMPOSITIONS FOR DETECTING RARE CELLS FROM A BIOLOGICAL SAMPLE

RELATED APPLICATIONS

This application is a continuation of application Ser. No. 11/777,962, filed Jul. 13, 2007, which claims benefit of priority to provisional application Ser. No. 60/831,156, filed Jul. 14, 2006, and is a continuation in part of application Ser. No. 11/497,919, filed Aug. 2, 2006; each of those applications is incorporated herein by reference in its entirety.

BACKGROUND OF THE INVENTION

The present invention relates generally to the field of bioseparation and cell detection, and in particular to the field of biological sample processing to detect rare cells, and downstream applications for the purpose of screening for high risk population, diagnosing a disease, predicting disease or treatment outcome, monitoring a disease state or response to a therapy, optimizing a treatment regimen or developing a new therapy.

The mortality associated with malignant tumors is mostly due to the formation of metastasis in tissues and organs distant from the primary tumor. The early detection of the metastasis is a very important determinant of the probability of survival for cancer patients (Feldstein M, Zelen M, Inferring the natural time history of breast cancer: implications for tumor growth rate and early detection. *Breast Cancer Res Treat.* 1984; 4(1):3-10; Senie R T, Lesser M, Kinne D W, Rosen P P, Method of tumor detection influences disease-free survival of women with breast carcinoma, *Cancer.* 1994 Mar. 15; 73(6):1666-72; Carlson J A, Slominski A, Linette G P, Mysliborski J, Hill J, Mihm M C Jr, Ross J S, Malignant melanoma 2003: predisposition, diagnosis, prognosis, and staging. *Am J Clin Pathol.* 2003 December; 120 Suppl:S101-27).

Early detection of tumors and monitoring of tumor growth are considered a very critical element in the successful treatment of cancer patients. Current diagnostic technologies rely largely on imaging and histopathology. Various imaging and scanning methods allow the detection of tumor masses based on the differential metabolic activity or tissue density. Other imaging technologies such as colonoscopy and branchoscopy help identify tumor tissue by directly imaging through the surface of a lumen. These methodologies have a lower limit of resolution of a few millimeters, which is equivalent to a mass already containing a large number of tumor cells ($>2\times10^8$). At this stage a tumor mass might be capable of shedding cancer cells in the bloodstream, with the potential to originate metastasis. Histopathology allows the diagnosis of a tumor utilizing a tissue sample obtained by means of a biopsy. While this approach provides direct visualization of the tumor cells, it's applicability in the diagnosis or monitoring of a tumor can be limited. Often, the location of the tumor is such that obtaining a biopsy sample may be impractical. In other cases, periodic monitoring by a temporal series of biopsy cannot be preformed at high enough frequency to provide useful information regarding the efficacy of a treatment and the progression of the disease. Another important limitation of the current histopathological approaches is that they can only provide data regarding the specific sites from which the biopsy was obtained, possibly overlooking the metastasis at other locations. Traditional histopathology can also be a risky process, during which tumor tissues or cells may be carried out to contaminate distal locations, causing potential metastasis during the biopsy procedure.

Typical progression of a localized tumor into a malignant cancer with metastasis involves multiple steps. At relatively early stages the tumor mass grows and the cells utilize nutrients available in the host tissue by simple diffusion. Later, once the tumor mass exceeds ~1 mm in diameter, the tumor becomes vascularized, a step necessary for the tumor cells to have adequate supply of nutrients and retain their ability to grow. The vascularization step is driven in part by angiogenic factors released by the tumor cells. As the tumor growth progresses, the cells lose more and more of the properties of the tissue of origin including the ability to tightly interact with the neighboring cells (see for example Blanco M J, Moreno-Bueno G, Sarrio D, Locascio A, Cano A, Palacios J, Nieto M A, Correlation of Snail expression with histological grade and lymph node status in breast carcinomas. *Oncogene.* 2002 May 9; 21(20):3241-6). Eventually a small number of tumor cells will leak into the blood vessels that are in direct contact with the tumor. Once in circulation, the circulating tumor cells can be carried to distant sites in the body. The majority of these cells will not adapt to the environment of the bloodstream and will die while still in the circulation. However, occasionally a subset of cells may survive in the circulation for a longer time, by chance, or because of their more resilient property. When a circulating tumor cell enters the capillaries in a distal region, it may remain trapped at that location. A series of events may then take place for these cells to attach and translocate across the endothelial wall of the capillary. If the tumor cell survives the harsh environment in the blood stream until it crosses the capillary wall, it can invade the surrounding tissue and establish a metastasis at the new location.

As a general rule, the more aggressive a cancer grows and the more metastases it forms, the more difficult it will be to cure. Localized tumors can be treated by surgical removal or by chemotherapy or a combination of the two. However, once the cancer cells have established multiple colonies at different locations in the body, surgical interventions at many sites or on multiple organs in the body become impractical and of limited therapeutic value. A cancer characterized by a single or multiple metastasis may be treated with chemotherapy. However, even in this case the success of the therapy may be limited because the different cancer colonies (the primary tumor and the metastasis) often respond differently to any give chemotherapy treatment (El Hilali N, Rubio N, Blanco J. Different effect of paclitaxel on primary tumor mass, tumor cell contents, and metastases for four experimental human prostate tumors expressing luciferase. *Clin Cancer Res.* 2005 Feb. 1; 11(3):1253-8). The differential response to treatment of the different cancer colonies is attributed to two main factors: genetic heterogeneity of the cancer cells at the different sites and local environmental factors differentially affecting cancer cell survival at the various locations.

All of these considerations emphasize the importance of detecting metastasis at early stages. However, major challenges to early diagnosis are posed by the difficulty of detecting small metastases. A metastasis can be established starting from a single cell shed off by a primary tumor. Current imaging methodologies (X-ray, PET-scan, CT-scan) cannot provide early diagnosis of metastasis because their sensitivity in not sufficient to detect a single metastatic cell, but can only detect a metastasis once it grows to several millimeters in diameter and contains more than 100 million cells. The ability to detect cancer cells in circulation early on during the establishment of a metastasis would be of great clinical relevance. Although a tumor mass can shed a significant number of cells on a daily basis, the number of circulating cancer cells in any given sample of blood of clinically relevant volume (5 to 40 mL) is very low. These cells are often present in the blood at a frequency of one cancer cell per $10^7$-$10^8$ white blood cells. This makes it very difficult to isolate and detect circulating cancer cells early in the metastatic process.

Tumors can occur in different tissues, such as epithelial and mesenchymal tissues. The majority of human solid tumors originate from epithelial cells that have undergone a transformation of their genetic material and their phenotype and escape the checkpoints that keep cell growth and cell division under control. It is generally recognized that a single mutation is not sufficient to generate a cancer cell but, instead, a sequence of mutations is necessary to initiate a tumor. The tumor cells are genetically unstable and continue to mutate and generate variants throughout the entire progression of the disease. The high genetic instability is the source of the heterogeneity observed among the tumor cells. In turn, the varied cell population in the tumor becomes the stage for evolutionary competition and selection in which the cells with the faster division time, highest metabolic rate and lowest differentiation grade, tend to grow and divide faster and eventually take over the entire population. Since new mutations and new tumor cell variants are constantly generated, a high degree of diversity is maintained in the tumor cell population.

The genetic instability and heterogeneity in the cells of the primary tumor has no clinical consequences since surgical intervention can remove the entire tumor mass and all of its cell variants. However, once the disease reaches the stage of metastatic cancer, the genetic diversity of the cancer cells in the primary tumor and the metastasis poses a major challenge for both the diagnosis as well as the treatment of the metastasis.

pithelial cells are tightly bound to one another and form sheets (called epithelia), which line all the cavities and surfaces of the body. One of the distinctive features of epithelial cells is the formation of tight intercellular junctions mediated by specialized protein complexes expressed on the surface of the epithelial cells. These cell-cell interactions leave very little space for extracellular space in epithelia and render the epithelia a selective barrier to the passage and diffusion of water, solutes and cells from one compartment of the body to another.

During the transformation of an epithelial cell into a metastatic cancer cell, numerous dramatic changes in the biological properties of the cell take place. The rate of growth and cell division is increased and the cell becomes progressively less dependent upon the growth control signal present in the normal tissue. Most importantly, in order to become metastatic, the cell needs to lose the key distinctive feature of epithelial cells: its ability to tightly bind to neighboring cells. In a well-known example of this situation, in breast cancer, the epithelial cell adhesion molecule E-Cadherin is lost in the cancer cells that progress to the metastatic stage. The protein E-Cadherin is actually known to be a "tumor suppressor", that is, a factor whose higher expression tends to suppress the progression of cancer. The changes associated with the transformation of epithelial cells into tumor cells are so dramatic that the cancer cells cannot be identified as epithelial cells anymore. This transformation is often referred-to as epithelial-mesenchymal transition, to indicate the conversion of an epithelial cell, characterized by strong interactions with neighbors cells, into a mesenchymal cell, a cell with loose or no interaction with other cells and free to migrate in a tissue.

In recent years it has also became apparent that the metastases are likely originating from a small subpopulation of tumor cells called cancer stem cells. These cells may be present in the tumor mass at a frequency <2% and are less differentiated than the majority of the cells in the tumor. Cancer stem cells have gained the property of duplicating themselves in addition to producing a differentiated offspring cell, which allow them to become "immortal", or having unlimited self reproduction potential. These cells have a high proliferation rate and can easily establish new metastasis at sites distant from the primary tumor. The importance of cancer stem cells in the diagnosis and treatment of metastatic cancer has been made clear by the observation that often the remission, or response to therapy as measured clinically using imaging of the primary tumor mass, is not predictive of the patient survival or time to recurrence. This apparent paradox can be explained by recognizing that the treatment capable (for example) of reducing the tumor mass, may be ineffective on the cancer stem cells, which are the main reason for uncontrolled and unlimited proliferation, and could still form distal metastasis.

At present, accumulating reports indicate that circulating tumor cells (CTCs) may be found in patients even before the primary tumor is detected. In addition to a potential role in early diagnosis and prognostication, CTCs may play a major role in characterizing genetic and immunophenotypic changes with tumor progression, thereby helping to guide individualized therapy. Though various techniques have been applied to isolate and characterize CTCs, many of them share the similar principle, i.e. antibody based positive selection. Apparently, application of this strategy for CTCs detection is limited by the availability, sensitivity, and specificity of antibodies against biomarkers on different tumor cells. Alternative strategies involve negative depletion of red blood cells (RBCs) and white blood cells (RBCs). The filtration approach to depletion the smaller RBCs and WBCs based on size risks losing target cells since certain target cells such as some CTCs can be as small as WBCs. Other approaches involving the lysis of RBCs might risk damaging target cells.

There is a need for a diagnostic methodology which has high sensitivity, and is capable of detecting cancer cells or cancer stem cells, or a certain population of more aggressive forms of cancer cells, such as cancer stem cells, in the body of a patient when said patient still has a relatively small tumor mass. In addition there is a need for a technology that can isolate and identify cancer cells or a certain population of more aggressive forms of cancer cells, such as cancer stem cells, in the body, regardless of the stage of the cancer, and the level of transformation accumulated by the cancer cells. Such a technology would allow for the identification of metastatic cancer disease at an early stage, or provide means for monitoring disease progression, response to therapy, or status of disease relapse. The present invention provides these and other benefits.

BRIEF SUMMARY OF THE INVENTION

The present invention recognizes that screening, diagnosis, prognosis, and treatment of many conditions can depend on the enrichment of rare cells from a complex fluid sample. Often, enrichment can be accomplished by one or more separation steps. In particular, the present invention recognizes that the enrichment or separation of rare cells including malignant cells from patient samples, such as the isolation of cancerous cells from patient body fluid samples, can aid in the detection and typing of such malignant cells and therefore aid in diagnostic decisions, as well as in the development of therapeutic modalities for patients.

The present methods utilize a negative or depletion approach for isolating rare cells from a sample. In these methods, a sample is progressively enriched for the rare cells of interest by a series of steps that remove other components from the sample with high specificity. Target cells, such as circulating tumor cells in blood samples, mesenchymal cells, epithelial cells, stem cells, mutated cells, and the like are then more easily identified in the enriched sample, and may be isolated, quantified, further characterized, or even grown in culture or used in other ways. Because this approach relies on depletion of non-target cells, it overcomes disadvantages of many 'positive selection' approaches for isolating rare cells. Those approaches can miss the rare cells if such cells have mutated, for example, and no longer express an expected surface antigen that is used to capture or label the target cells. Since mutations are commonly seen in cells that such methods would desirably detect, such as cancer cells, the depletion methods of the present invention have substantial advantages over 'positive selection' methods for isolating rare cells from complex biological samples.

A first aspect of the present invention is a method of enriching target cells from a biological sample such as a peripheral blood sample, though other biological samples can also be similarly enriched. Target cells may be epithelial cells, mesenchymal cells, cancer cells, infected cells, mutated cells, damaged cells, stem cells, or other cells that occur infrequently in biological samples. Often, the target cell is a cell type whose presence, number, proportion, or properties are useful for a diagnostic or prognostic assessment of the subject from whom the biological sample was collected.

In one aspect, the invention provides a method for isolating a target cell from a biological sample containing other types of cells, said method comprising:
  a) enriching the sample by selectively removing at least one non-target cell type without removing the target cell;
  b) debulking the sample by reducing the sample volume without removing the target cell; and
  c) subjecting the enriched sample comprising the target cell to a downstream process that identifies, characterizes, or utilizes the target cell or information about its presence, proportion, properties. In some embodiments, this method does not utilize centrifugation.

In one aspect of the invention, the presence, number, proportion, or characteristics of the target cell(s), if present, can be used to provide diagnostic or prognostic information about the subject from whom the sample was collected. This may be done, for example, by correlation of the presence, number, proportion or properties of such target cells in the subject to those parameters in samples from healthy and diseased individuals. The methods may be used to determine the presence or status of cancer, for example, or to determine the subject's remission status, the effectiveness of a course of therapy, the metastatic potential of the cancer, and the like. It may be used to evaluate experimental therapies or drug candidates, too. In some embodiments, the method includes additional steps such as identification of the tissue origin of the target cell, which may assist in determining the location of a tumor or a metastasis site, or further steps such as growing a culture of cells from the target cell(s) in a suitable medium. A culture of such target cells can also be used to evaluate experimental therapies or drug candidates.

In certain embodiments, after washing a blood sample, the blood sample is centrifuged at a speed that enhances the recovery of a rare cell type of interest, against serum proteins and blood constituents that have lower gravitational density than cells. In one embodiment of this aspect, a blood sample (obtained from a cancer patient or from a subject potentially at risk for cancer) is washed and centrifuged at a speed that enhances recovery of cancer cells.

In some embodiments of this method, during washing of a blood sample, the cells in the blood sample are concentrated to enhance their recovery by means of a French press type of device. In one embodiment of this aspect, a blood sample (obtained from a cancer patient) is washed by applying a pressure differential on a filtration device, which allows for the fluid component of the blood sample to enter a separate compartment from the one in which the cells are confined. This device may be a microfiltration device that selectively separates at least some fluid from a sample that contains target cells by passing the fluid through a filter having pores that are sized to permit some components of the sample to pass through and to substantially prevent passage of the target cells. In some embodiments, this filter is adapted to repel the target cells from its surface by surface modifications of the filter itself, or by use of a force that selectively repels the target cells from the filter, such as a dielectrophoretic force generated by one or more electrodes on or near the filter.

In some embodiments, this method includes at least some of the following steps: providing a blood sample from a cancer patient; washing the sample by adding an artificial buffer followed by centrifugation; in which after the wash centrifugation, a wash supernatant and a washed pellet are obtained; resuspending the washed pellet, which represents an enriched sample; lysing certain non-target cells in the sample, such as red blood cells by adding an artificial buffer, and centrifuging to obtain a further enriched pellet containing the target cells and some non-target cells and a supernatant containing lysed non-target cell residues. Optionally, the lysing step can be repeated to achieve the best result. Depending upon the sample characteristics, these steps and others described below may be performed in any order, and may be repeated or omitted as needed to enrich the target cell population to a sufficient degree for its intended use.

In certain embodiments, the present invention uses a specific binding member such as an antibody or molecule that specifically binds a surface molecule or moiety on a type of non-target cell (such as a WBC or other hematopoietic cell) with lesser binding to the target cells as part of the enrichment process. Non-limiting examples of suitable specific binding members include an antibody or molecule that binds CD3, CD11b, CD14, CD17, CD31, CD34, CD45, CD50, CD53, CD63, CD69, CD81, CD84, CD102, CD166, CD233, CD235, and CD236, or a combination of antibodies chosen from this list. The antibody may be utilized to remove white blood cells from a blood sample, for example, as part of the enrichment process. The antibody can optionally be bound to a solid support, which support may be specially adapted to facilitate its removal from the sample. In preferred embodiments of the present invention, the antibody can be used to remove white blood cells from a blood sample in a procedure for enriching cancer cells from a blood sample.

In one aspect, the invention provides methods for enriching a sample with rare cells, using a French press type device. It also provides devices to facilitate this method, which comprise a filter that is preferably a rigid material having one or more pores through it, and optionally having one or more electrodes on or adjacent to its surface to produce a dielectrophoretic effect that can repel cells in the sample from the surface of the filter and thereby improve the operation of the filter.

Another aspect of the present invention is a method of enriching target cells from a biological sample, which includes the following steps: a) removing white blood cells (WBCs) from said blood sample with microparticles and b) removing red blood cells (RBCs) from said blood sample to enrich non-hematopoietic cells with a density-based approach e.g., a ficoll gradient centrifugation, and c) performing an analysis, manipulation or application step with the enriched sample. Steps a) and b) can be performed in either order or at the same time.

In some embodiments, the present invention includes methods of separating sample components from a fluid sample using magnetic particles which could be any solid phase particle/microspheres such as magnetic particle, sepharose, sephadex, and agarose etc based particles, and the particles are chemically modified to conjugate antibody or any other proteins for target selection and binding.

In certain embodiments, the present invention involves the method of removal of WBCs from blood sample, which involves microparticles with a dimension between 10 nm and 10 um, and linked to specific binding member such as an antibody or molecule that specifically binds to an antibody which recognizes antigens expressing on leukocyte, such as a CD45 and/or CD50 antibody and/or another leukocyte-specific antibody. In some embodiments, one specific binding member is used. In other embodiments, two or more different specific binding members are used.

In another embodiment of the present invention, the density-based approach involves centrifugation and usage of sugar or derivatives of sugar such as ficoll as the material for establishing a density gradient. Furthermore, the density media used in this method has the same separation effect as ficoll diluted to 50%~100% with a buffer.

In a certain embodiment, this invention is designed to very rapidly remove plasma proteins, most WBCs and RBCs with lesser undesired effects, resulting in easy detection of target cells from remaining enriched cells. In addition, the current invention can also be applied to separate plasma protein, enrich other rare cells, including stem cells, fetal cells, immune cells, etc, followed by downstream analysis, manipulations, and applications such as flowcytometry, PCR, immunofluorescence, immunocytochemistry, image analysis, enzymatic assays, gene expression profiling analysis, efficacy tests of therapeutics, culturing of enriched rare cells, and therapeutic use of enriched rare cells.

In some embodiment of the present invention, enriched cells are stained with both fluorescence-based reagents, and absorbance-based reagents, such as Hemotoxylin. Immunofluorescence and immunocytochemistry approaches can be used at the same time to increase the number of stains and biomarkers that can be employed to characterize the enriched sample.

In one embodiment, before applying any enrichment protocol described in the present invention, a pre-labeled or non-labeled known cell type can be mixed with the sample to be analyzed, with a specific labeling that will not be used for the identification or characterization of the target cells. This pre-mixed cell can serve as an "internal control" that qualifies the performance of the assay.

In some embodiments, the current invention can employ a multiplicity of specific binding members against a multiplicity of biomarkers on more than one type of target cells, i.e., circulating tumor cells, and circulating endothelial cells. Such procedures can enable the simultaneous detection of two or more target cells, with different pathophysiological significance or indications.

In a certain embodiment, target cells enriched by the current invention, are analyzed by fluorescence microscopy. To aid the accurate reading of fluorescence-labeled samples, a slide or cover slide is prepared with suitable methods such as laser, wet etch, dry etch, ion beam, etc, to create grid lines to assist the slide reading. The natural fluorescence of the grid lines can be further enhanced by treating with fluorescent materials, such as quantum dots, or fluorescent dyes.

In one embodiment, the present invention is directed to a method for detecting a non-hematopoietic cancer cell, in a blood sample, which method comprises: a) providing a blood sample; b) removing red blood cells (RBCs) from said blood sample, with a density-based approach, such, e.g., a Ficoll density centrifugation, and removing white blood cells (WBCs) from said blood sample to provide an enriched sample containing the non-hematopoietic cell, e.g., a non-hematopoietic tumor cell, if any is present, from said blood sample, with a microparticle-based approach; and c) assessing the presence, absence and/or amount of said enriched non-hematopoietic cell or tumor cell. The microparticle-based approach often uses a particle that is 10 nm to 10 microns in size, with a specific binding member linked to the particle. The specific binding member is typically an antibody or similar binder that is specific for at least one surface antigen on leukocytes. The microparticle may comprise a magnetic material to facilitate separation of the particle from the enriched sample. Detection of the presence or number of such non-hematopoietic cancer cells can be used to assess the presence, status, or progression of a non-hematopoietic cancer in the subject from which the blood sample was taken.

A further aspect of the present invention is a method for identifying cancer cells following their enrichment from a blood sample that comprises: enriching the cancer cells in a sample by removing the majority of the non-cancer cells from the sample, which may be a blood sample, for example; specifically labeling the cancer cells with a detectable label after at least one such enrichment step; and counting the number of labeled cancer cells in the enriched sample. Alternatively, the ratio or proportion of such enriched cancer cells to other cell types such as non-cancerous epithelial cells, or non-stem type cancer cells, may be used as a diagnostic or prognostic indicator that may be more reliable than counting of the cancer cells. The labeling of the cancer cells is sometimes achieved using a plurality of markers in order to obviate to the genetic instability and population heterogeneity typical of cancer cells.

In a preferred embodiment, tumor cells are labeled and identified by binding to a specific binding member or a multiplicity of specific binding members recognizing one or more ligands selected from the group consisting of ACPP, AFP, albumin, ALCAM, AMAS, ARF6, ARMCX3, ATP1A1, BAG1, BJ-TSA-9, blc-2 βHCG, CA125, CA15-3, CA19-9, Cathepsin B1, CD44, CD44v6, CD56, CD66a, CD66b, CD66c, CD66d, CD66e, CD66f, CD147, CDH2, CDK4I, CDKN2A, CDX2, CEA, CLDN3, CLDN4, CLDN5, c-met, CST3, Cytokeratins, CK18, CK19, CK20, Desmoplakin-3, EAG1, EGFR, EGP2, EMA, ErbB2, ESR1, FAK, FOXA2, GalNac-T, GCTFTI5, GFAP, Haptoglobin-α, HCA, hCASK, HE4, HEPA1, hERG, HIP-1, HMB45, HSPA2, IGFR, IVL, KCNK-9, KHDRBS3, Ki67, Kv1.3, LAMB2, Lewis-Y antigen, LIMA, LM06, LUNX, MAGE-3, MAGE-A3, mammoglobin, Maspin, Melan-A, MITF, MPP5, MPST, MUC-1, MUC5AC, NCAM-1, NSDHL, Oct4, OTC, p53, p97, p1B, PCNA, PGR, PMSA, PS-2, PSA, RPS6KA5, S100, S100A1, S100A2, S100B, SLC2A1, Smoothelin, SP-1, SPARC, Surfactant, Telomerase, TFAP2A, TITF1 (TTF1), TFF2, TRAIL, TRIM28, TRPM-8, TYR, Tyrosinase, TYRP1, Ubiquitin thiolesterase, VEGF, WT1, X-protein, ZNF165. Leading references for selected markers: *Clin Cancer Res.* 2005 May 15; 11(10):3678-85 (CA15-3); *Clin Cancer Res.* 2004 Apr. 15; 10(8):2812-7 (FAK); *J Clin Invest.* 2002 August; 110(3):351-60 (HIP-1); *Neoplasia* 2005 December; 7(12):1073-80 (BJ-TSA-9); *Cancer Detect Prev.* 1994; 18(1):65-78 (AMAS); *J*

Biol. Chem. 2006 Apr. 7; 281(14):9719-27. Epub 2006 Jan 27 (CD147); Lab Invest. 2003 September; 83(9):1343-52 (TFF2); Cancer. 1995 Jun. 15; 75(12):2827-35 (Lewis Y antigen).

In the embodiments where a multiplicity of specific binding members is used, each binding member might carry none, the same, or different labels. In a preferred embodiment of the present invention the cancer cells are identified with specific markers and also stained with markers of apoptosis. In some embodiments of the present invention the absolute number and/or the proportion of cancer cells which are also apoptotic can be used as a predictor of the efficacy of an anticancer therapy or the progression of the disease or the prognosis for the subject, or combinations of the above.

The cancer cells isolated using the depletion methods described in the present invention are sometimes identified by their affinity for a specific binding member, which is typically labeled for easy detection. Target cells may be recognized and labeled by their affinity for antibodies directed at one or more of the following: ACPP, AFP, albumin, ALCAM, AMAS, ARF6, ARMCX3, ATP1A1, BAG1, BJ-TSA-9, blc-2 βHCG, CA125, CA15-3, CA19-9, Cathepsin B1, CD44, CD44v6, CD56, CD66a, CD66b, CD66c, CD66d, CD66e, CD66f, CD147, CDH2, CDK4I, CDKN2A, CDX2, CEA, CLDN3, CLDN4, CLDN5, c-met, CST3, Cytokeratins, CK18, CK19, CK20, Desmoplakin-3, EAG1, EGFR, EGP2, EMA, ErbB2, ESR1, FAK, FOXA2, GalNac-T, GCTFTI5, GFAP, Haptoglobin-α, HCA, hCASK, HE4, HEPA1, hERG, HIP-1, HMB45, HSPA2, IGFR, IVL, KCNK-9, KHDRBS3, Ki67, Kv1.3, LAMB2, Lewis-Y antigen, LIMA, LM06, LUNX, MAGE-3, MAGE-A3, mammoglobin, Maspin, Melan-A, MITF, MPP5, MPST, MUC-1, MUC5AC, NCAM-1, NSDHL, Oct4, OTC, p53, p97, p1B, PCNA, PGR, PMSA, PS-2, PSA, RPS6KA5, S100, S100A1, S100A2, S100B, SLC2A1, Smoothelin, SP-1, SPARC, Surfactant, Telomerase, TFAP2A, TITF1 (TTF1), TFF2, TRAIL, TRIM28, TRPM-8, TYR, Tyrosinase, TYRP1, Ubiquitin thiolesterase, VEGF, WT1, X-protein, ZNF165. In the embodiments where two or more specific binding members are used to label the target cells, each binding member might carry none, the same, or different labels. The apoptotic cancer cells are often further identified by detection of one or more of the following: Phosphatidylserine, DNA fragmentation, Cytochrome C, Caspase. The ratio of identified apoptotic cells to the overall specific rare cell population identified by methods of the current invention may be used as a diagnostic index.

In some preferred embodiments, after debulking (reducing the volume or cell mass or both) of the sample and the removal of undesirable components from the blood sample (e.g., hematopoietic cells, non-cancerous epithelial cells, etc.), labeled cancer cells are further enriched or isolated using magnetic capture methods, fluorescence activated cell sorting or laser cytometry. In some preferred embodiments, after debulking and the removal of various components from the sample to provide an enriched sample containing the cancer or other cells of interest, the rare cells of interest are labeled with a specific marker. The labeled cancer cells are further analyzed using spectral imaging, fluorescence microscopy, visible light microscopy, or manual or automated image analysis.

In some preferred embodiments of the present invention the cancer cells are identified using a combination of immunological and morphological criteria. The cancer cells are frequently labeled by binding to a specific binding member or a multiplicity of specific binding members recognizing one or more ligands selected from the group consisting of ACPP, AFP, albumin, ALCAM, AMAS, ARF6, ARMCX3, ATP1A1, BAG1, BJ-TSA-9, blc-2 βHCG, CA125, CA15-3, CA19-9, Cathepsin B1, CD44, CD44v6, CD56, CD66a, CD66b, CD66c, CD66d, CD66e, CD66f, CD147, CDH2, CDK4I, CDKN2A, CDX2, CEA, CLDN3, CLDN4, CLDN5, c-met, CST3, Cytokeratins, CK18, CK19, CK20, Desmoplakin-3, EAG1, EGFR, EGP2, EMA, ErbB2, ESR1, FAK, FOXA2, GalNac-T, GCTFTI5, GFAP, Haptoglobin-α, HCA, hCASK, HE4, HEPA1, hERG, HIP-1, HMB45, HSPA2, IGFR, IVL, KCNK-9, KHDRBS3, Ki67, Kv1.3, LAMB2, Lewis-Y antigen, LIMA, LM06, LUNX, MAGE-3, MAGE-A3, mammoglobin, Maspin, Melan-A, MITF, MPP5, MPST, MUC-1, MUC5AC, NCAM-1, NSDHL, Oct4, OTC, p53, p97, p1B, PCNA, PGR, PMSA, PS-2, PSA, RPS6KA5, S100, S100A1, S100A2, S100B, SLC2A1, Smoothelin, SP-1, SPARC, Surfactant, Telomerase, TFAP2A, TITF1 (TTF1), TFF2, TRAIL, TRIM28, TRPM-8, TYR, Tyrosinase, TYRP1, Ubiquitin thiolesterase, VEGF, WT1, X-protein, ZNF165. In the embodiments where a multiplicity of specific binding members is used, each binding member might carry none, the same, or different labels. Identification of cancer cells is often done by fluorescence microscopy, visible light microscopy, or manual or automated image analysis wherein a cancer cell is identified as a cell labeled by binding members recognizing one, or two, or three or more of the markers listed above, and optionally also by specific morphological criteria related to the size of its nucleus, shape and boundary characteristics of the nucleus, size of the whole cell, or the ratio of the cytoplasmic portion of the cells to its nucleus.

In another aspect, the present invention is directed to a method for detecting a non-hematopoietic cell, e.g., a non-hematopoietic cancer cell, in a blood sample, which method comprises steps including some or all of the following:

a) providing a blood sample;

b) removing red blood cells (RBCs) from said blood sample by selectively lysing said RBCs, and removing the remaining hematopoietic cells such as white blood cells (WBCs) by specific binding of said hematopoietic cells to specific binding members, such as binding WBCs to an anti-CD50 antibody or another leukocyte-specific antibody, which may be linked to a solid surface such as a microparticle or a magnetic particle, to enrich the sample with the targeted cancer cells, if any are present; and c) subjecting the enriched sample comprising the target cell to a downstream process that identifies, characterizes, or utilizes the target cell population, which can include assessing the presence, absence and/or amount of said enriched non-hematopoietic cell, e.g., a non-hematopoietic tumor cell, by: i) bright field microscopy following nucleus and/or cytoplasm staining and applying morphological criteria, ii) immunostaining the enriched non-hematopoietic cell and counting the labeled cells; iii) PCR-based analysis of the enriched non-hematopoietic cells; or detecting the presence or amount of an enzyme, surface marker or nucleic acid that is typically present in, and preferably is uniquely associated with, the target cell type.

In still another aspect, the present invention is directed to a kit for detecting a non-hematopoietic cell, e.g., a non-hematopoietic tumor cell, in a blood sample, which kit comprises: a) means for removing red blood cells (RBCs) from a blood sample, with the proviso that said means is not a Ficoll gradient centrifugation means; and means for removing white blood cells (WBCs) from said blood sample to enrich a non-hematopoietic cell, e.g., a non-hematopoietic tumor cell, if any, from said blood sample; and b) means for assessing the presence, absence and/or amount of said enriched non-hematopoietic cell, e.g., a non-hematopoietic tumor cell, or means for assessing what fraction of non-hematopoietic cells are cancerous, or means for assessing what fraction of target cells are apoptotic or possess stem cell traits. Suitable means for removing RBCs are disclosed herein and include a lysis buffer or a solid surface or particle linked to a specific binding member that binds to RBCs. Suitable means for removing WBCs are also disclosed herein, and include, for example microparticles that are optionally magnetic and are linked to at least one specific binding member that is selective for binding to leukocyte surface antigens. Means for assessing the presence, absence and/or amount of an enriched non-hematopoietic cell are also disclosed herein, and include labeled antibodies directed against the tumor marker compounds described herein.

Another aspect of the present invention is the use of the presence of cancer cells in a blood sample from a subject for the purpose of diagnosing cancer, wherein the presence of cancer cells in a blood sample from said patient is indicative of the presence of a tumor in the body of said subject, and may be indicative of a likelihood of progression or metastasis of the tumor. The cancer cells are isolated using one or more of the depletion methods described herein, or methods known in the art that can include positive selection methods, and the positive identification of the cancer cells is obtained by labeling said cells with one or more cancer marker-specific binders that recognize a cancer marker selected from the following list: ACPP, AFP, albumin, ALCAM, AMAS, ARF6, ARMCX3, ATP1A1, BAG1, BJ-TSA-9, blc-2 βHCG, CA125, CA15-3, CA19-9, Cathepsin B1, CD44, CD44v6, CD56, CD66a, CD66b, CD66c, CD66d, CD66e, CD66f, CD147, CDH2, CDK4I, CDKN2A, CDX2, CEA, CLDN3, CLDN4, CLDN5, c-met, CST3, Cytokeratins, CK18, CK19, CK20, Desmoplakin-3, EAG1, EGFR, EGP2, EMA, ErbB2, ESR1, FAK, FOXA2, GalNac-T, GCTFTI5, GFAP, Haptoglobin-α, HCA, hCASK, HE4, HEPA1, hERG, HIP-1, HMB45, HSPA2, IGFR, IVL, KCNK-9, KHDRBS3, Ki67, Kv1.3, LAMB2, Lewis-Y antigen, LIMA, LM06, LUNX, MAGE-3, MAGE-A3, mammoglobin, Maspin, Melan-A, MITF, MPP5, MPST, MUC-1, MUC5AC, NCAM-1, NSDHL, Oct4, OTC, p53, p97, p1B, PCNA, PGR, PMSA, PS-2, PSA, RPS6KA5, S100, S100A1, S100A2, S100B, SLC2A1, Smoothelin, SP-1, SPARC, Surfactant, Telomerase, TFAP2A, TITF1 (TTF1), TFF2, TRAIL, TRIM28, TRPM-8, TYR, Tyrosinase, TYRP1, Ubiquitin thiolesterase, VEGF, WT1, X-protein, ZNF165. In embodiments where a multiplicity of specific binding members are used, each binding member might carry none, the same, or different labels.

Another aspect of the present invention is the monitoring of disease progression, response to therapy, or relapse in a patient with cancer. During the natural progression of cancer disease, or as a result of treatment, often cancer cells mutate their surface antigens, rendering positive selection methods inadequate for detection of cancer cells in biological samples. The depletion methods of the present invention are effective in the isolation and identification of cancer cells in samples from cancer patients. In a preferred embodiment of the invention, the number of cancer cells in a blood sample from a patient, as determined by the methods of the present invention, is determined at different time intervals during the progression of the disease or during a treatment regimen lasting weeks, months or longer, or after a treatment regimen has been discontinued. An increase in the number of cancer cells over time is indicative of lack of response to therapy, relapse, higher risk of metastasis, worse prognosis, shortened projected survival time, or progression to a higher stage of cancer or growth rate of the tumor, or combinations of the above. A decrease or non-varying number of cancer cells is indicative of favorable response to therapy, stable status of the disease, or shrinkage of the tumor or remission or combinations of the above.

In a preferred embodiment of the present invention, the cancer cells isolated from a cancer patient are characterized for their nucleic acid content. This method can comprise steps such as: a) providing a blood sample; b) removing red blood cells (RBCs) from said blood sample by selectively lysing said RBCs; c) removing white blood cells (WBCs) from said blood sample by specific binding of said WBCs to an anti-CD50 antibody or other leukocyte-specific antibody to enrich the sample with the targeted cancer cells, if any are present; d) amplifying RNA and/or DNA from the isolated cancer cells; and e) characterizing the genetic content and/or gene expression pattern in the cancer cells using one or more of the following methodologies: single nucleotide polymorphism, quantitative PCR, FISH, DNA sequencing, multiplexed PCR, determination of the DNA methylation, total DNA content quantification, whole genome amplification (WGA), CGH, laser dissection microscopy (LDM), amplification from RNA, Oligonucleotide ligation assay (OLA), Chromosome immuno-precipitation (CHIP), southern blot, hybridization, amplification, ligation, enzymatic assays.

Another aspect of the present invention is the monitoring of disease progression, response to therapy, or relapse in a patient with cancer by means of assessment of the malignancy index. The malignancy index is determined as the ratio between α, the number of circulating candidate cancer cells or, circulating epithelial cells, and the number of cells ∈, which are non-apoptotic (or apoptotic) and/or over-express angiogenic markers and/or over-express proliferation markers and/or have reduced expression of tumor suppression genes, and/or have lost markers of differentiation and/or contains chromosomal deletion spanning tumor suppressor genes and/or contain chromosomal amplification of tumor promoters and/or over-express drug resistance factors and/or contain specific mutations. In certain embodiments, the α and ∈ values are determined by using markers that identify surface antigens characteristic of a particular cellular status, and the markers or sets of markers used to determine α and ∈ are not identical.

The number ∈ of epithelial cells or candidate cancer cells in a blood sample can be determined as follows: a) providing a blood sample; b) removing red blood cells (RBCs) from said blood sample by selectively lysing said RBCs, and removing white blood cells (WBCs) from said blood sample by specific binding of said WBCs to an anti-CD50 antibody and/or another leukocyte-specific antibody(s) to enrich the sample with the targeted cancer cells, if any are present; c) identification of the candidate cancer cells or the epithelial cells in the enriched sample is achieved by labeling said cells with one or more cancer markers selected from the following list: ACPP, AFP, albumin, ALCAM, AMAS, ARF6, ARMCX3, ATP1A1, BAG1, BJ-TSA-9, blc-2 βHCG, CA125, CA15-3, CA19-9, Cathepsin B1, CD44, CD44v6, CD56, CD66a, CD66b, CD66c, CD66d, CD66e, CD66f, CD147, CDH2, CDK4I, CDKN2A, CDX2, CEA, CLDN3, CLDN4, CLDN5, c-met, CST3, Cytokeratins, CK18, CK19, CK20, Desmoplakin-3, EAG1, EGFR, EGP2, EMA, ErbB2, ESR1, FAK, FOXA2, GalNac-T, GCTFTI5, GFAP, Haptoglobin-α, HCA, hCASK, HE4, HEPA1, hERG, HIP-1, HMB45, HSPA2, IGFR, IVL, KCNK-9, KHDRBS3, Ki67, Kv1.3, LAMB2, Lewis-Y antigen, LIMA, LM06, LUNX, MAGE-3, MAGE-A3, mammoglobin, Maspin, Melan-A, MITF, MPP5, MPST, MUC-1, MUC5AC, NCAM-1, NSDHL, Oct4, OTC, p53, p97, p1B, PCNA, PGR, PMSA, PS-2, PSA, RPS6KA5, S100, S100A1, S100A2, S100B, SLC2A1, Smoothelin, SP-1, SPARC, Surfactant, Telomerase, TFAP2A, TITF1 (TTF1), TFF2, TRAIL, TRIM28, TRPM-8, TYR, Tyrosinase, TYRP1, Ubiquitin thiolesterase, VEGF, WT1, X-protein, ZNF165. In the embodiments where a multiplicity of specific binding members is used, each binding member might carry none, the same, or different labels.

The number α of cancer cells which are apoptotic, or highly malignant or de-differentiated or mutated or having high proliferation rate in a blood sample can be determined as follows: a) providing a blood sample; b) removing red blood cells (RBCs) from said blood sample by selectively lysing said RBCs, and removing white blood cells (WBCs) from said blood sample by specific binding of said WBCs to an anti-CD50 antibody and/or another leukocyte-specific antibody(s) to enrich the sample with the targeted cancer cells, if any are present; c) identifying the cancer cells by labeling said cells with one or more cancer marker selected from the following list: Phosphatidylserine, DNA fragmentation, Cytochrome C, Caspase expression, ACPP, AFP, albumin, ALCAM, AMAS, ARF6, ARMCX3, ATP1A1, BAG1, BJ-TSA-9, blc-2 βHCG, CA125, CA15-3, CA19-9, Cathepsin B1, CD44, CD44v6, CD56, CD66a, CD66b, CD66c, CD66d, CD66e, CD66f, CD147, CDH2, CDK4I, CDKN2A, CDX2, CEA, CLDN3, CLDN4, CLDN5, c-met, CST3, Cytokeratins, CK18, CK19, CK20, Desmoplakin-3, EAG1, EGFR, EGP2, EMA, ErbB2, ESR1, FAK, FOXA2, GalNac-T, GCT-FTI5, GFAP, Haptoglobin-α, HCA, hCASK, HE4, HEPA1, hERG, HIP-1, HMB45, HSPA2, IGFR, IVL, KCNK-9, KHDRBS3, Ki67, Kv1.3, LAMB2, Lewis-Y antigen, LIMA, LM06, LUNX, MAGE-3, MAGE-A3, mammoglobin, Maspin, Melan-A, MITF, MPP5, MPST, MUC-1, MUC5AC, NCAM-1, NSDHL, Oct4, OTC, p53, p97, p1B, PCNA, PGR, PMSA, PS-2, PSA, RPS6KA5, S100, S100A1, S100A2, S100B, SLC2A1, Smoothelin, SP-1, SPARC, Surfactant, Telomerase, TFAP2A, TITF1 (TTF1), TFF2, TRAIL, TRIM28, TRPM-8, TYR, Tyrosinase, TYRP1, Ubiquitin thiolesterase, VEGF, WT1, X-protein, ZNF165. In the embodiments where a multiplicity of specific binding members is used, each binding member might carry none, the same, or different labels.

In a preferred embodiment of the invention the malignancy index for a patient, as determined by the methods of the present invention, is determined at different time intervals before, during or after treatment. An increase in the malignancy index over time is indicative of lack of response to therapy, higher risk of metastasis, worse prognosis, shortened projected survival time, or progression to a higher stage of cancer, growth of the tumor or combinations of the above. A decrease or non-varying value of the malignancy index is indicative of favorable response to therapy, stable disease status or shrinkage of the tumor or remission or combinations of the above.

In a preferred embodiment of the present invention, the cancer cells isolated from a cancer patient by either positive or negative (depletion) methods are characterized for their nucleic acid content. One such method comprises: a) providing a blood sample; b) removing red blood cells (RBCs) from said blood sample by selectively lysing said RBCs, and removing white blood cells (WBCs) from said blood sample by specific binding of said WBCs to an anti-CD50 antibody or another leukocyte-specific antibody to enrich the sample with the targeted cancer cells, if any are present; c) amplifying RNA and/or DNA from the isolated cancer cells; d) characterizing the genetic content and/or gene expression pattern in the cancer cells using one or more of the following methodologies: single nucleotide polymorphism, quantitative PCR, FISH, DNA sequencing, multiplexed PCR, determination of the DNA methylation, total DNA content quantification, whole genome amplification (WGA), CGH, LDM, amplification from RNA, OLA, CHIP, southern blot, hybridization, amplification, ligation, enzymatic assays.

In some preferred embodiments of the present invention the genetic content of the cancer cells is analyzed for the purpose of identifying the presence of mutations which can confer higher proliferation rates or chromosomal deletions spanning tumor suppressor genes or chromosomal amplification of tumor promoting genes.

In a further embodiment of the present invention, the characterization of the genetic content of cancer cells isolated from a subject is used to tailor a personalized therapeutic course specific to said subject or to the particular cancer phenotype.

Another aspect of the present invention includes the culturing and in vitro propagation of cancer cells isolated from a biological sample obtained from a cancer patient. This method can comprise: a) providing a blood sample; b) removing red blood cells (RBCs) from said blood sample by selectively lysing said RBCs, and removing white blood cells (WBCs) from said blood sample by specific binding of said WBCs to an anti-CD50 antibody or similar leukocyte-specific antibody to enrich the sample with cancer cells; c) transferring of the enriched cancer cells sample into microtiter plates or similar container, and culturing in serum free media or media with serum concentration at or below 20% or preferably below about 5%.

In one aspect, the present invention provides a method to evaluate progress in a clinical study of an experimental cancer therapy or drug candidate. The subjects in such trials may be human, but frequently they would include other mammals such as mice, rats, dogs, monkeys and the like. In this aspect, the method can be used to provide a clinical end point to measure the efficacy of an experimental cancer therapy or drug candidate that is faster and more quantitative than effectiveness, metastasis or recurrence data alone. This provides a more rapid and quantitative assessment of the efficacy of the therapeutic being tested, and it provides additional information about how the therapeutic affects metastasis and recurrence probabilities for the cancer being treated. It thus provides more information about the overall effectiveness of the experimental therapy and reduces the time required for such clinical trials.

In a preferred embodiment of the invention the cultured cancer cells obtained from a cancer patient blood sample are used to test in vitro the efficacy of candidate anti-cancer drugs or drug combinations before administration of the drug(s) to said patient, or before deciding whether to continue administration of the drug(s). In other embodiments, such cultured cancer cells are used to test new drug candidates or other experimental therapies as part of a clinical trial or even a primary screen for efficacy.

In another aspect of the present invention, the cancer cells isolated from a cancer patient using the methods of the present invention, are immortalized by in vitro culturing and selection which may or may not be aided by transfection of the cells with SV40 T-antigen or Telomerase or other suitable methods. The immortalized cells may then be used to test the efficacy of anticancer agents, screen for new anticancer agents, or any other investigation requiring immortalized cell lines.

In another aspect of the present invention, the cancer cells isolated from a cancer patient using the methods of the present invention are used in invasiveness assays.

Another aspect of the present invention is the use of the cancer cells isolated from a cancer patient for the purpose of personalized immunotherapy, wherein proteins or nucleic acids or combinations thereof obtained from the cancer cells isolated from a cancer patient are incubated with WBC or a subfraction of WBC from said patient to stimulate a cancer specific immune response. The WBC or the subfraction of WBC exposed to the cancer cell tumor antigens are then re-inoculated into the patient.

In one embodiment of the present invention a blood sample from a cancer patient is utilized for isolation of the cancer cells (from the cellular fraction) and performing standard biochemical assays (from the plasma fraction). After obtaining a blood sample from a cancer patient, said sample is centrifuged to sediment all the cellular components. Following the centrifugation step, the plasma fraction or a portion of this fraction is recovered and removed from the cell pellet. The cellular fraction is resuspended in an appropriate buffer and the cancer cells are isolated using the depletion methods and cancer cell detection methods of the present invention. The plasma fraction is utilized for routine clinical assays including, but not limited to, the determination of plasma concentration of: Sodium, Potassium, Urea, Creatinine, Glucose, total protein, Albumin, Bilirubin, Alanine Transaminase, Alkaline Phosphatase, Gamma Glutamyl Transferase, Creatine Kinase, Aspartate Transaminase, Lactate Dehydrogenase, Amylase, C-reactive protein, D-dimer, Calcium, Copper, Zinc, Triglycerides, total Cholesterol, HDL Cholesterol, LDL Cholesterol, Alpha-fetoprotein, CA-125, Prostate specific antigen, TSH, FT4, FT3, ACTH, Cortisol, Prolactin, Testosterone.

In one embodiment of the present invention, following the isolation of the cancer cells from a blood sample using the depletion methods described in the present invention, the cancer cells can be characterized using several immunoassays. For example, the cancer cells can be lysed, and the lysate centrifuged, and subjected to ELISA assay. In this case, specific protein of interest expressed in the cancer cells can be detected directly. This can provide a profile of the protein content in the cancer cells and allows the monitoring of how the cancer cell phenotype changes during the course of the disease or during the therapeutic treatment.

In some preferred embodiments of the present invention the cancer cells, following isolation, are characterized by one or more functional or enzymatic assays. Telomerase activity has been identified in lung cancer cells as well as in cancer cells from many other cancers. Telomerase activity assay can be used to further characterize circulating tumor cells isolated with the depletion methods of the present invention or with positive selection methods well known to those skilled in the arts. In this case, telomerase repeat amplification protocol (TRAP) can be performed. Once the cancer cells are isolated, telomerase will be extracted using CHAPS based detergent buffer or any other suitable method. The supernatant of cell lysates will be used as template for telomerase extension reaction by PCR. Fluorescent PCR products are generated using fluorescently labeled primers, followed by capillary electrophoresis measurements. The larger the amount of fluorescent PCR product generated or the larger the length of the telomerase repeat amplification products, the higher the telomerase activity of the cancer cells in the sample, which can be an indicator of the aggressiveness of the tumor or of the number or fraction of cancer cells in the enriched sample.

In recent years antibody-based therapy has had significant success in the clinics and is now part of the standard arsenal used by clinicians to fight cancer. The methods of the present invention provide a unique approach in monitoring the effects and the efficacy of antibody-based therapies. In some embodiments the present invention can be used to detect the interaction between circulating cancer cells in the blood of a cancer patient and an immunotherapeutic such as a humanized exogenous antibody used for the therapy. Whether isolated cancer cells are bound to a therapeutic antibody can be determined by isolating a cancer cell and examining it for the presence of such antibodies; one such method includes: a) providing a blood sample; b) removing red blood cells (RBCs) from said blood sample by selectively lysing said RBCs, and removing white blood cells (WBCs) from said blood sample by specific binding of said WBCs to an anti-CD50 antibody or another leukocyte-specific antibody to enrich the sample with the targeted cancer cells, if any are present; c) identifying the cancer cells bound to the therapeutic antibody by labeling said cells with one or more ligands having specific affinity for the therapeutic antibody, and optionally with additional binding members for the candidate cancer cells; d) visualizing the labeled cells using the appropriate methods to visualize a molecular ligand, which methods, include but are not limited to fluorescence microscopy, immunohistochemistry, bright field microscopy and FACS, which methods are well known to those skilled in the arts. However, this method can also be practiced in connection with positive-selection cell isolation methods known in the art, such as those that select the target cell from a biological fluid or sample by exposing the sample to a plurality of magnetic beads coated with a specific binding member that binds to a surface marker on the target cell.

In some preferred embodiments of the present invention the monitoring of the interaction between therapeutic antibody and the cancer cells present in a blood sample can be used to evaluate the patient's response to therapy wherein when the fraction of cancer cells bound to an immunotherapeutic agent such as an antibody is above a predetermined value, or increases over time for measurements at different time points, the outcome of the treatment is predicted to be favorable, and when the fraction of cancer cells bound to the antibody is below a predetermined value, or decreases over time for measurements at different time points, the outcome of the treatment is predicted to be unfavorable. Where an absolute number is not used, a ratio between the fraction of cells bound to the said antibody over the entire candidate cancer cell population or the unbound candidate cancer cell fraction can also be used.

The enriched samples can be characterized and/or further manipulated in a downstream process performed on a miniaturized microfluidic device, such as a microfluidic chip or cartridge. Such device may comprise one or more elements that use the principle(s) of dielectrophoresis, thermal gradient, acoustic, electroosmosis, or electromagnetic manipulation. Such device may also comprise filtration, mixing, sonication, thermal cycling, immunomagnetic separation, nucleic acid hybridization, two-photon microscopy, absorbance-based detection, fluorescence-based detection, FRET-based detection, immunorecognition, impedance measurement, electrical field stimulation, or cell culture functions. One preferred embodiment of the present invention involves obtaining a sample enriched by a method described in the present invention, loading the enriched sample onto a microfluidic device that then separates rare cells of interest from the rest of the cells in the sample, directing the separated cells to individual culture chambers for incubation, subjecting each culture chambers to therapeutic agents to be tested, and generating a suitable readout that is useful to evaluate the effects of the therapeutic agents.

The enrichment procedures described in the present invention may be miniaturized on a microfluidic device, such as a microchip or a cartridge.

A. Fluid sample containing target cells is shown inside the French press. (1) Main chamber containing the fluid samples to be debulked. (2) Filter. (3) Piston used to move the filter through the sample. (4) Inlet valve, to allow introducing of the sample in the main chamber (5) Outlet valve to allow exit of the debulked sample. (6) Target cell B. Debulked sample showing new position of the filtration unit at the end of the debulking procedure FIG. 2. Staining of human white blood cells with anti-CD50 monoclonal antibody The results of CD50 staining on white blood cells are shown FIG. 3. Staining of human cancer cells with anti-CD50 monoclonal antibody Shows the lack of specific interaction between anti-CD50 antibody and cancer cells obtained from different types of cancers (indicated)

Figure 4:
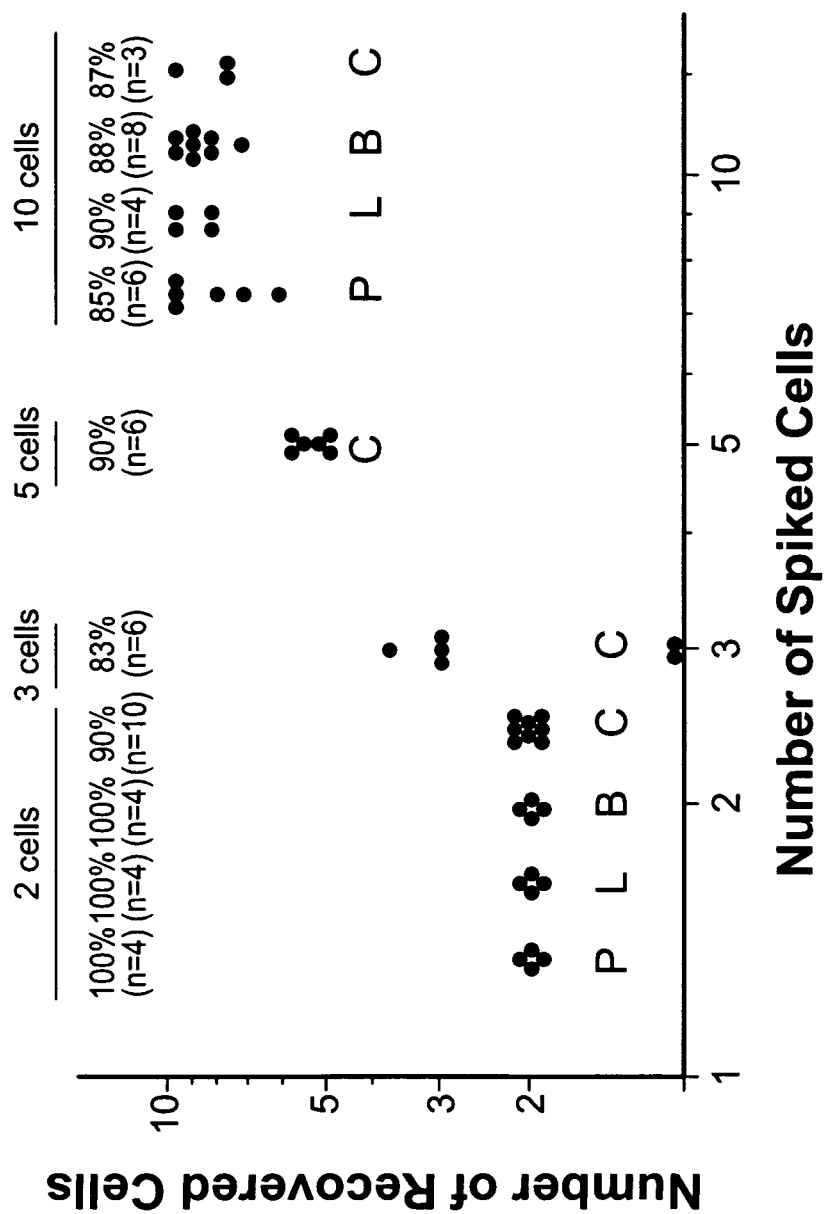

FIG. 4. Recovery of cancer cells from spiked blood samples

P, prostate cancer cells; L, lung cancer cells; B, breast cancer cells; C, Cervical cancer cells FIG. 5. Cancer cells isolated from breast cancer patient Top, normal cells from control healthy patient Bottom three panels, examples of breast cancer cells.

Figure 6:
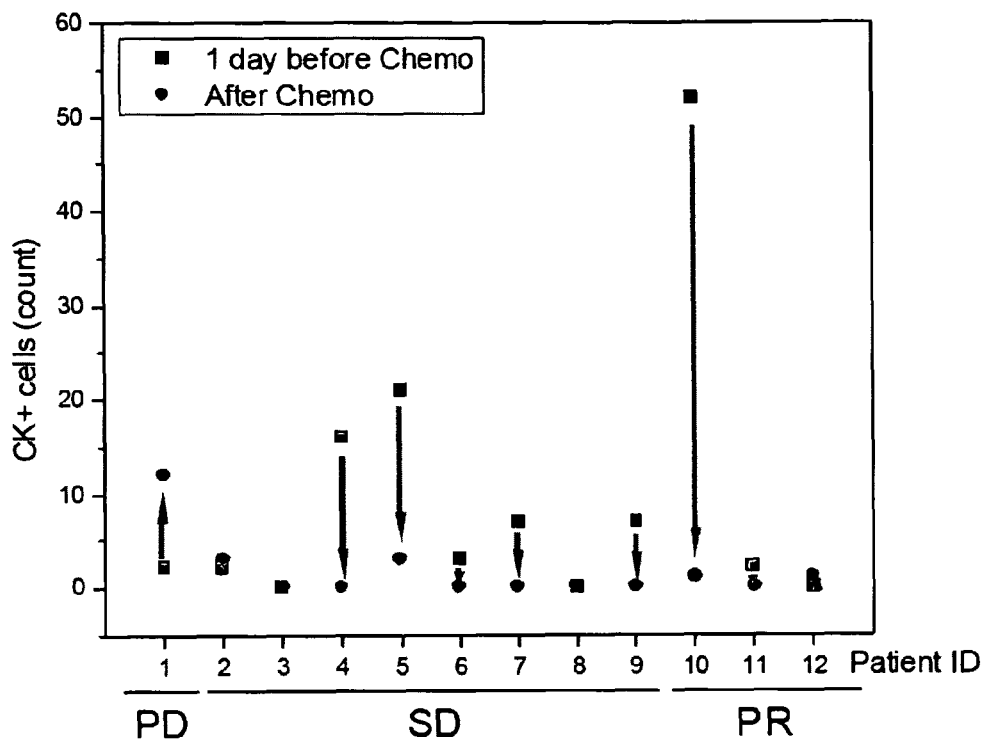

FIG. 6. Changes of CTC count before and after chemotherapy (4-6 weeks) correlated with clinical response assessed by CT scan.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the manufacture procedures for devices and components as well as the laboratory procedures described below are well known and commonly employed in the art. Conventional methods are used for these procedures, such as those provided in the art and various general references. Where a term is provided in the singular, the inventors also contemplate the plural of that term. As employed throughout the disclosure, the following terms, unless otherwise indicated, shall be understood to have the following meanings: A "component" of a sample or "sample component" is any constituent of a sample, and can be an ion, molecule, compound, molecular complex, organelle, virus, cell, aggregate, or particle of any type, including colloids, aggregates, particulates, crystals, minerals, etc. A component of a sample can be soluble or insoluble in the sample media or a provided sample buffer or sample solution. A component of a sample can be in gaseous, liquid, or solid form. A component of a sample may be a moiety or may not be a moiety.

A "moiety" or "moiety of interest" is any entity whose manipulation is desirable. A moiety can be a solid, including a suspended solid, or can be in soluble form. A moiety can be a molecule. Molecules that can be manipulated include, but are not limited to, inorganic molecules, including ions and inorganic compounds, or can be organic molecules, including amino acids, peptides, proteins, glycoproteins, lipoproteins, glycolipoproteins, lipids, fats, sterols, sugars, carbohydrates, nucleic acid molecules, small organic molecules, or complex organic molecules. A moiety can also be a molecular complex, can be an organelle, can be one or more cells, including prokaryotic and eukaryotic cells, or can be one or more etiological agents, including viruses, parasites, or prions, or portions thereof. A moiety can also be a crystal, mineral, colloid, fragment, micelle, droplet, bubble, or the like, and can comprise one or more inorganic materials such as polymeric materials, metals, minerals, glass, ceramics, and the like. Moieties can also be aggregates of molecules, complexes, cells, organelles, viruses, etiological agents, crystals, colloids, or fragments. Cells can be any cells, including prokaryotic and eukaryotic cells, whether living or dead. Eukaryotic cells can be of any type. Of particular interest are cells such as, but not limited to, white blood cells, normal cells, modified cells, mutated cells, malignant cells, stem cells, progenitor cells, fetal cells, and cells infected with an etiological agent, and bacterial cells. Moieties can also be artificial particles such polystyrene microbeads, microbeads of other polymer compositions, magnetic microbeads, and carbon microbeads.

As used herein, "manipulation" refers to moving or processing of the moieties, which results in one-, two- or three-dimensional movement of the moiety, whether within a single chamber or on a single chip, or between or among multiple chips and/or chambers. Moieties that are manipulated by the methods of the present invention can optionally be coupled to binding partners, such as microparticles. Non-limiting examples of the manipulations include transportation, capture, focusing, enrichment, concentration, aggregation, trapping, repulsion, levitation, separation, isolation or linear or other directed motion of the moieties. For effective manipulation of moieties coupled to binding partners, the binding partner and the physical force used in the method must be compatible. For example, binding partners with magnetic properties must be used with magnetic force. Similarly, binding partners with certain dielectric properties, e.g., plastic particles, polystyrene microbeads, must be used with dielectrophoretic force.

"Binding partner" or "binding member" refers to any substances that both bind to the moieties with desired affinity or specificity and are manipulatable with the desired physical force(s). Non-limiting examples of the binding partners include cells, cellular organelles, viruses, microparticles or an aggregate or complex thereof, or an aggregate or complex of molecules.

A "microparticle" or "particle" is a structure of any shape and of any composition that is manipulatable by desired physical force(s). The microparticles used in the methods could have a dimension from about 0.01 micron to about ten centimeters. Preferably, the microparticles used in the methods have a dimension from about 0.1 micron to about several thousand microns. Frequently, they are in the range 0.1 to 10 microns or 1-100 microns in size. Such particles or microparticles can be comprised of any suitable material, such as glass or ceramics, and/or one or more polymers, such as, for example, nylon, polytetrafluoroethylene (TEFLON™), polystyrene, polyacrylamide, sepaharose, agarose, cellulose, cellulose derivatives, or dextran, and/or can comprise metals. Examples of microparticles include, but are not limited to, plastic particles, ceramic particles, carbon particles, polystyrene microbeads, glass beads, magnetic beads, hollow glass spheres, metal particles, particles of complex compositions, microfabricated or micromachined particles, etc.

"Coupled" means bound. For example, a moiety can be coupled to a microparticle by specific or nonspecific binding. As disclosed herein, the binding can be covalent or noncovalent, reversible or irreversible.

As used herein, "the moiety to be manipulated is substantially coupled onto surface of the binding partner" means that a percentage of the moiety to be manipulated is coupled onto a surface of the binding partner and can be manipulated by a suitable physical force via manipulation of the binding partner. Ordinarily, at least 0.1% of the moiety to be manipulated is coupled onto a surface of the binding partner. Preferably, at least 1%, 5%, 10%, 20%, 30%, 40%, 50%, 60%, 70%, 80% or 90% of the moiety to be manipulated is coupled onto a surface of the binding partner.

As used herein, "the moiety to be manipulated is completely coupled onto surface of the binding partner" means that at least 90% of the moiety to be manipulated is coupled onto surface of the binding partner. Preferably, at least 91%, 92%, 93%, 94%, 95%, 96%, 97%, 98%, 99% or 100% of the moiety to be manipulated is coupled onto a surface of the binding partner.

A "specific binding member" is one of two different molecules having an area on the surface or in a cavity which specifically binds to and is thereby defined as complementary with a particular spatial and chemical organization of the other molecule. A specific binding member can be a member of an immunological pair such as antigen-antibody or antibody-antibody, can be biotin-avidin, biotin-streptavidin, or biotin-neutravidin, ligand-receptor, nucleic acid duplexes, IgG-protein A, DNA-DNA, DNA-RNA, RNA-RNA, and the like.

An "antibody" is an immunoglobulin molecule, and can be, as nonlimiting examples, an IgG, an IgM, or other type of immunoglobulin molecule. As used herein, "antibody" also refers to a portion of an antibody molecule that retains the binding specificity of the antibody from which it is derived (for example, single chain antibodies or Fab fragments).

A "nucleic acid molecule" is a polynucleotide. A nucleic acid molecule can be DNA, RNA, or a combination of both. A nucleic acid molecule can also include sugars other than ribose and deoxyribose incorporated into the backbone, and thus can be other than DNA or RNA. A nucleic acid can comprise nucleobases that are naturally occurring or that do not occur in nature, such as xanthine, derivatives of nucleobases, such as 2-aminoadenine, and the like. A nucleic acid molecule of the present invention can have linkages other than phosphodiester linkages. A nucleic acid molecule of the present invention can be a peptide nucleic acid molecule, in which nucleobases are linked to a peptide backbone. A nucleic acid molecule can be of any length, and can be single-stranded, double-stranded, or triple-stranded, or any combination thereof.

"Homogeneous manipulation" refers to the manipulation of particles in a mixture using physical forces, wherein all particles of the mixture have the same response to the applied force.

"Selective manipulation" refers to the manipulation of particles using physical forces, in which different particles in a mixture have different responses to the applied force, including situations where a force used for manipulation of one particle has no effect on other particles.

A "fluid sample" is any fluid from which components are to be separated or analyzed. A sample can be from any source, such as an organism, group of organisms from the same or different species, from the environment, such as from a body of water or from the soil, or from a food source or an industrial source. A sample can be an unprocessed or a processed sample. A sample can be a gas, a liquid, or a semi-solid, and can be a solution or a suspension. A sample can be an extract, for example a liquid extract of a soil or food sample, an extract of a throat or genital swab, or an extract of a fecal sample, or a wash of an internal area of the body.

A "blood sample" as used herein can refer to a processed or unprocessed blood sample, i.e., it can be a centrifuged, filtered, extracted, or otherwise treated blood sample, including a blood sample to which one or more reagents such as, but not limited to, anticoagulants or stabilizers have been added. An example of blood sample is a buffy coat that is obtained by processing human blood for enriching white blood cells. Another example of a blood sample is a blood sample that has been "washed" to remove serum components by centrifuging the sample to pellet cells, removing the serum supernatant, and resuspending the cells in a solution or buffer. Other blood samples include cord blood samples, bone marrow aspirates, internal blood or peripheral blood. A blood sample can be of any volume, and can be from any subject such as an animal or human. A preferred subject is a human.

A "rare cell" is a cell that is either 1) of a cell type that is less than 1% of the total nucleated cell population in a fluid sample, or 2) of a cell type that is present at less than one million cells per milliliter of fluid sample. A "rare cell of interest" is a cell whose enrichment is desirable.

A 'desired cell' or 'target cell' is a specific type of rare cell of interest that might be identified and/or separated and/or enriched from other types of cells by methods involving a marker or property that is preferentially present or absent on the desired or target cells. Cells that are desirably removed in order to facilitate the identification, isolation, or characterization of a target cell are referred to as "non-target cells", and a biological sample may contain multiple types of non-target cells; accordingly, the methods of the invention can be used in various combinations to remove different non-target cells. For example, more than one type of cell may be removed by use of one or more selective lysis steps; more than one type of non-target cell may be removed by selective binding to a solid support, and this may involve individual steps, each using a specific binding member to remove one cell type, or it may involve a single processing step where the sample is exposed to more than one specific binding member adhered to one or more solid surfaces, to effect removal of more than one type of non-target cell in one step.

"Without removing a target cell" as used herein means that the specific step or combination of steps removes no more than 50% of the target cell population from a sample, when the target cell type is present. This can be determined by spiking a sample with a known number of target cells to determine how many are recovered for detection; as a standard, the efficiency of recovery can be determined by spiking a sample with 5-10 target cells and determining how many of those cells are detected after the enrichment process. Preferably the step or combination of steps removes less than 50% of the target cells from the sample, and typically the present methods remove less than 35% of the target cells. In some embodiments, the combination of steps used to isolate a target cell population from a sample remove on average less than about 30% of the target cells, or less than 20% of the target cells. In some embodiments, the steps or the overall method remove less than 10% of the target cells, or less than 5% of the target cells, or less than about 1% of the target cells.

As used herein, "removing a non-target cell" or cell type means that at least a majority of the non-target cell population is removed by the step. Cells are removed when they are taken out of the sample, or when they are lysed so that they would no longer be recognized as cells and are readily separated from the target cells by well known methods such as filtration or centrifugation, which separate intact cells from smaller debris. The individual steps for removing a non-target cell type can be repeated to further remove the non-target cell and further enrich the target cells in the sample.

A "white blood cell" or "WBC" is a leukocyte, or a cell of the hematopoietic lineage that is not a reticulocyte or platelet and that can be found in the blood of an animal or human. Leukocytes can include natural killer cells ("NK cells") and lymphocytes, such as B lymphocytes ("B cells") or T lymphocytes ("T cells"). Leukocytes can also include phagocytic cells, such as monocytes, macrophages, and granulocytes, including basophils, eosinophils and neutrophils. Leukocytes can also comprise mast cells.

A "red blood cell" or "RBC" is an erythrocyte. Unless designated a "nucleated red blood cell" ("nRBC") or "fetal nucleated red blood cell" or nucleated fetal red blood cell, as used herein, "red blood cell" is used to mean a non-nucleated red blood cell.

"Neoplastic cells" or "tumor cells" or "cancer cells" refers to abnormal was are or were part of a tumor, or the progeny of such cells. These cells tend to show partial or complete lack of structural organization and functional coordination with the normal tissue, and may be benign or malignant. Cancer cells, unlike benign tumor cells, exhibit the properties of invasion and metastasis and are highly anaplastic. Cancer cells include the two broad categories of carcinoma and sarcoma.

A "tumor" or "neoplasm" is an abnormal growth of tissue resulting from uncontrolled, progressive multiplication of cells and serving no physiological function; a neoplasm A "cancer" is any of various malignant neoplasms characterized by the proliferation of anaplastic cells that tend to invade surrounding tissue and metastasize to new body sites.

A "malignant cell" is a cell having the property of locally invasive and destructive growth and distal metastasis. Examples of "malignant cells" include, but not limited to, leukemia cells, lymphoma cells, cancer cells of solid tumors, metastatic solid tumor cells (e.g., breast cancer cells, prostate cancer cells, lung cancer cells, colon cancer cells) in various body fluids including blood, bone marrow, ascitic fluids, stool, urine, bronchial washes etc.

A "cancerous cell" is a cell that exhibits deregulated growth and, in most cases, has lost at least one of its differentiated properties, such as, but not limited to, characteristic morphology, non-migratory behavior, cell-cell interaction and cell-signaling behavior, protein expression and secretion pattern, etc. In most cases, cancerous cells are either of epithelial or of mesenchymal origin that are distinguishable from normal epithelial cells.

"Cancer" refers to a neoplastic disease the natural course of which is fatal. Cancer cells, unlike benign tumor cells, exhibit the properties of invasion and metastasis and are highly anaplastic. Cancer cells include the two broad categories of carcinoma and sarcoma.

A "stem cell" is an undifferentiated cell that can give rise, through one or more cell division cycles, to at least one differentiated cell type.

A "progenitor cell" is a committed but undifferentiated cell that can give rise, through one or more cell division cycles, to at least one differentiated cell type. Typically, a stem cell gives rise to a progenitor cell through one or more cell divisions in response to a particular stimulus or set of stimuli, and a progenitor gives rise to one or more differentiated cell types in response to a particular stimulus or set of stimuli.

An "etiological agent" refers to any etiological agent, such as a bacteria, fungus, protozoan, virus, parasite or prion that can infect a subject. An etiological agent can cause symptoms or a disease state in the subject it infects. A human etiological agent is an etiological agent that can infect a human subject. Such human etiological agents may be specific for humans, such as a specific human etiological agent, or may infect a variety of species, such as a promiscuous human etiological agent.

"Subject" refers to any organism, such as an animal or a human. An animal can include any animal, such as a feral animal, a companion animal such as a dog or cat, an agricultural animal such as a pig or a cow, or a pleasure animal such as a horse.

A "chamber" is a structure that is capable of containing a fluid sample, in which at least one processing step can be performed. The chamber may have various dimensions and its volume may vary between ten microliters and 0.5 liter.

A "filtration chamber" is a chamber through which or in which a fluid sample can be filtered.

A "filter" is a structure that comprises one or more pores or slots of particular dimensions (that can be within a particular range), that allows the passage of some sample components but not others from one side of the filter to the other, based on the size, shape, and/or deformability of the particles. A filter can be made of any suitable material that prevents passage of insoluble particles, such as metal, ceramics, glass, silicon, plastics, polymers, fibers (such as paper or fabric), etc.

A "filtration unit" is a filtration chamber and the associated inlets, valves, and conduits that allow sample and solutions to be introduced into the filtration chamber and sample components to be removed from the filtration chamber. A filtration unit optionally also comprises a loading reservoir.

A "cartridge" is a structure that comprises at least one chamber that is part of a manual or automated system and one or more conduits for the transport of fluid into or out of at least one chamber. A cartridge may or may not comprise one or more chips.

An "automated system for separating rare cells from a fluid sample" or an "automated system" is a device that comprises at least one filtration chamber, automated means for directing fluid flow through the filtration chamber, and at least one power source for providing fluid flow and, optionally, means for providing a signal source for the generation of forces on active chips. An automated system of the present invention can also optionally include one or more active chips, separation chambers, separation columns, or permanent magnets.

A "port" is an opening in the housing of a chamber through which a fluid sample can enter or exit the chamber. A port can be of any dimensions, but preferably is of a shape and size that allows a sample to be dispensed into a chamber by pumping a fluid through a conduit, or by means of a pipette, syringe, or other means of dispensing or transporting a sample.

An "inlet" is a point of entrance for sample, solutions, buffers, or reagents into a fluidic chamber. An inlet can be a port of a chamber, or can be an opening in a conduit that leads, directly or indirectly, to a chamber of an automated system.

An "outlet" is the opening at which sample, sample components, or reagents exit a fluidic chamber. The sample components and reagents that leave a chamber can be waste, i.e., sample components that are not to be used further, or can be sample components or reagents to be recovered, such as, for example, reusable reagents or target cells to be further analyzed or manipulated. An outlet can be a port of a chamber, but preferably is an opening in a conduit that, directly or indirectly, leads from a chamber of an automated system.

A "conduit" is a means for fluid to be transported from a container to a chamber of the present invention. Preferably a conduit directly or indirectly engages a port in the housing of a chamber. A conduit can comprise any material that permits the passage of a fluid through it. Conduits can comprise tubing, such as, for example, rubber, Teflon, or tygon tubing. Conduits can also be molded out of a polymer or plastic, or drilled, etched, or machined into a metal, glass or ceramic substrate. Conduits can thus be integral to structures such as, for example, a cartridge of the present invention. A conduit can be of any dimensions, but preferably ranges from 10 microns to 5 millimeters in internal diameter. A conduit is preferably enclosed (other than fluid entry and exit points), or can be open at its upper surface, as a canal-type conduit.

"Enrich" means increase the relative concentration of a sample component of a sample relative to other sample components (which can be the result of reducing the concentration of other sample components), or increase the absolute concentration of a sample component. For example, as used herein, "enriching" nucleated fetal cells from a blood sample includes increasing the proportion of nucleated fetal cells to all cells in the blood sample, enriching cancer cells of a blood sample can mean increasing the concentration of cancer cells in the sample (for example, by reducing the sample volume) or reducing the concentration or number of other cellular components of the blood sample to increase the percentage of cells present that are cancer cells, and "enriching" cancer cells in a urine sample can mean increasing their concentration in the sample such as by reducing sample volume or reducing the number of 'non-cancer' cells in the sample.

"Separation" is a process in which one or more components of a sample are spatially separated from one or more other components of a sample. A separation can be performed such that one or more sample components of interest is translocated to or retained in one or more areas of a separation apparatus and at least some of the remaining components are translocated away from the area or areas where the one or more sample components of interest are translocated to and/ or retained in, or in which one or more sample components is retained in one or more areas and at least some or the remaining components are removed from the area or areas. Alternatively, one or more components of a sample can be translocated to and/or retained in one or more areas and one or more sample components can be removed from the area or areas. It is also possible to cause one or more sample components to be translocated to one or more areas and one or more sample components of interest or one or more components of a sample to be translocated to one or more other areas. Separations can be achieved through, for example, filtration, or the use of physical, chemical, electrical, or magnetic forces. Non-limiting examples of forces that can be used in separations are gravity, mass flow, dielectrophoretic forces, traveling-wave dielectrophoretic forces, and electromagnetic forces.

"Separating a sample component from a (fluid) sample" means separating a sample component from other components of the original sample, or from components of the sample that are remaining after one or more processing steps. "Removing a sample component from a (fluid) sample" means removing a sample component from other components of the original sample, or from components of the sample that are remaining after one or more processing steps.

"Capture" is a type of separation in which one or more moieties or sample components is retained in or on one or more areas of a surface, chamber, chip, bead particles, tube, or any vessel that contains a sample, where the remainder of the sample can be removed from that area.

An "assay" is a test performed on a sample or a component of a sample. An assay can test for the presence of a component, the amount or concentration of a component, the composition of a component, the activity of a component, etc. Assays that can be performed in conjunction with the compositions and methods of the present invention include, but not limited to, immunocytochemical assays, interphase FISH (fluorescence in situ hybridization), karyotyping, immunological assays, biochemical assays, binding assays, cellular assays, genetic assays, gene expression assays and protein expression profiling assays.

A "binding assay" is an assay that tests for the presence or concentration of an entity by detecting binding of the entity to a specific binding member, or that tests the ability of an entity to bind another entity, or tests the binding affinity of one entity for another entity. An entity can be an organic or inorganic molecule, a molecular complex that comprises, organic, inorganic, or a combination of organic and inorganic compounds, an organelle, a virus, or a cell. Binding assays can use detectable labels or signal generating systems that give rise to detectable signals in the presence of the bound entity. Standard binding assays include those that rely on nucleic acid hybridization to detect specific nucleic acid sequences, those that rely on antibody binding to entities, and those that rely on ligands binding to receptors.

A "biochemical assay" is an assay that tests for the presence, concentration, or activity of one or more components of a sample.

A "cellular assay" is an assay that tests for a cellular process, such as, but not limited to, a metabolic activity, a catabolic activity, an ion channel activity, an intracellular signaling activity, a receptor-linked signaling activity, a transcriptional activity, a translational activity, or a secretory activity.

A "genetic assay" is an assay that tests for the presence or sequence of a genetic element, where a genetic element can be any segment of a DNA or RNA molecule, including, but not limited to, a gene, a repetitive element, a transposable element, a regulatory element, a telomere, a centromere, or DNA or RNA of unknown function. As nonlimiting examples, genetic assays can be gene expression assays, PCR assays, karyotyping, or FISH. Genetic assays can use nucleic acid hybridization techniques, can comprise nucleic acid sequencing reactions, or can use one or more enzymes such as polymerases, as, for example a genetic assay based on PCR. A genetic assay can use one or more detectable labels, such as, but not limited to, fluorochromes, radioisotopes, or signal generating systems.

"Immunostaining" refers to staining of a specific antigen or structure such as a cell by any method in which the stain (or stain-generating system, or signal-generating system) is complexed with a specific antibody.

"Polymerase chain reaction" or "PCR" refers to method for amplifying specific sequences of nucleotides (amplicon). PCR depends on the ability of a nucleic acid polymerase, preferably a thermostable one, to extend a primer on a template containing the amplicon. RT-PCR is a PCR based on a template (cDNA) generated from reverse transcription from mRNA prepared from a sample. Quantitative Reverse Transcription PCR (qRT-PCR) or the Real-Time RT-PCR is a RT-PCR in which the RT-PCR products for each sample in every cycle are quantified.

"FISH" or "fluorescence in situ hybridization" is an assay wherein a genetic marker can be localized to a chromosome by hybridization. Typically, to perform FISH, a nucleic acid probe that is fluorescently labeled is hybridized to interphase chromosomes that are prepared on a slide. The presence and location of a hybridizing probe can be visualized by fluorescence microscopy. The probe can also include an enzyme and be used in conjunction with a fluorescent enzyme substrate.

"Karyotyping" refers to the analysis of chromosomes that includes the presence and number of chromosomes of each type (for example, each of the 24 chromosomes of the human haplotype (chromosomes 1-22, X, and Y)), and the presence of morphological abnormalities in the chromosomes, such as, for example, translocations or deletions. Karyotyping typically involves performing a chromosome spread of a cell in metaphase. The chromosomes can then be visualized using, foe example, but not limited to, stains or genetic probes to distinguish the specific chromosomes.

A "gene expression assay" (or "gene expression profiling assay") is an assay that tests for the presence or quantity of one or more gene expression products, i.e. messenger RNAs. The one or more types of mRNAs can be assayed simultaneously on cells of the interest from a sample. For different applications, the number and/or the types of mRNA molecules to be assayed in the gene expression assays may be different.

A "protein expression assay" (or "protein expression profiling assay") is an assay that tests for the presence or quantity of one or more proteins. One or more types of protein can be assayed simultaneously on the cells of the interest from a sample. For different applications, the number and/or the types of protein molecules to be assayed in the protein expression assays may be different.

"Histological examination" refers to the examination of cells using histochemical or stains or specific binding members (generally coupled to detectable labels) that can determine the type of cell, the expression of particular markers by the cell, or can reveal structural features of the cell (such as the nucleus, cytoskeleton, etc.) or the state or function of a cell. In general, cells can be prepared on slides and "stained" using dyes or specific binding members directly or indirectly bound to detectable labels, for histological examination. Examples of dyes that can be used in histological examination are nuclear stains, such as Hoescht stains, or cell viability stains, such as Trypan blue, or cellular structure stains such as Wright or Giemsa, enzyme activity benzidine for HRP to form visible precipitate. Examples of specific binding members that can be used in histological examination of fetal red blood cells are antibodies that specifically recognize fetal or embryonic hemoglobin.

A "well" is a structure in a chip, with a lower surface surrounded on at least two sides by one or more walls that extend from the lower surface of the well or channel. The walls can extend upward from the lower surface of a well or channel at any angle or in any way. The walls can be of an irregular conformation, that is, they may extend upward in a sigmoidal or otherwise curved or multi-angled fashion. The lower surface of the well or channel can be at the same level as the upper surface of a chip or higher than the upper surface of a chip, or lower than the upper surface of a chip, such that the well is a depression in the surface of a chip. The sides or walls of a well or channel can comprise materials other than those that make up the lower surface of a chip.

A "pore" is an opening in a surface, such as a filter of the present invention, that provides fluid communication between one side of the surface and the other. A pore can be of any size and of any shape, but preferably a pore is of a size and shape that restricts passage of at least one insoluble sample component from one side of a filter to the other side of a filter based on the size, shape, and deformability (or lack thereof), of the sample component.

"Continuous flow" means that fluid is pumped or injected into a chamber of the present invention continuously during the separation process. This allows for components of a sample that are not selectively retained in a chamber to be flushed out of the chamber during the separation process.

"Binding partner" refers to any substances that both bind to the moieties with desired affinity or specificity and are manipulatable with the desired physical force(s). Non-limiting examples of the binding partners include microparticles.

A "microparticle" is a structure of any shape and of any composition that is manipulatable by desired physical force(s). The microparticles used in the methods could have a dimension from about 0.01 micron to about ten centimeters. Preferably, the microparticles used in the methods have a dimension from about 0.1 micron to about several hundred microns. Such particles or microparticles can be comprised of any suitable material, such as glass or ceramics, and/or one or more polymers, such as, for example, nylon, polytetrafluoroethylene (TEFLON™), polystyrene, polyacrylamide, sepaharose, agarose, cellulose, cellulose derivatives, or dextran, and/or can comprise metals. Examples of microparticles include, but are not limited to, magnetic beads, magnetic particles, plastic particles, ceramic particles, carbon particles, polystyrene microbeads, glass beads, hollow glass spheres, metal particles, particles of complex compositions, microfabricated free-standing microstructures, etc. The examples of microfabricated free-standing microstructures may include those described in "Design of asynchronous dielectric micromotors" by Hagedorn et al., in Journal of Electrostatics, Volume: 33, Pages 159-185 (1994). Particles of complex compositions refer to the particles that comprise or consists of multiple compositional elements, for example, a metallic sphere covered with a thin layer of non-conducting polymer film.

"A preparation of microparticles" is a composition that comprises microparticles of one or more types and can optionally include at least one other compound, molecule, structure, solution, reagent, particle, or chemical entity. For example, a preparation of microparticles can be a suspension of microparticles in a buffer, and can optionally include specific binding members, enzymes, inert particles, surfactants, ligands, detergents, etc.

Other technical terms used herein have their ordinary meaning in the art that they are used, as exemplified by a variety of technical dictionaries.

The present invention recognizes that the diagnosis and monitoring of cancer disease faces challenges posed by the multiplicity of locations at which a cancer can develop in a patient and the fact that a small number of cells can give rise to a tumor or metastasis. The shedding of cancer cells into the bloodstream is a common characteristic of cancer disease and is central to the present invention's ability to diagnose and monitor cancer using biological fluid samples (such as blood samples) obtained from patients. Analysis of complex fluids, such as biological fluid samples, can be confounded by many sample components that can interfere with the analysis. Sample analysis can be even more problematic when the target of the analysis is a rare cell type, for example, when the target cells are malignant cells present in the blood of a patient. In processing such samples, it is often necessary to both "debulk" the sample, by reducing the volume to a manageable level, and to enrich the population of cancer cells that are the target of analysis. Procedures for the processing of fluid samples are often time consuming and inefficient. In some aspects, the present invention provides efficient methods for the enrichment of cancer cells from blood samples. In addition the present invention further recognizes that the molecular composition of a cancer cells can mutate or evolve during the course of the disease. Also the methods described in this invention are designed to very rapidly remove plasma proteins, most WBCs and RBCs with lesser undesired effects, resulting in easy detection of CTCs in an enriched sample. The current invention can be applied to separate plasma protein, enrich other rare cells, including stem cells, fetal cells, immune cells, etc, followed by downstream analysis, manipulations, and applications such as flow cytometry, PCR, immunofluorescence, immunocytochemistry, image analysis, enzymatic assays, gene expression profiling analysis, efficacy tests of therapeutics, culturing of enriched rare cells, and therapeutic use of enriched rare cells. Central to the present invention are methods and compositions for the isolation and identification of cancer cells throughout the course of the disease and use of information about the presence and/or abundance of such cancer cells in a method to detect, diagnose or prognose a cancer. The methods of the present invention can overcome the variability and genetic instability typical of cancer cells, thus providing a reliable diagnostics approach.

As a non-limiting introduction to the breadth of the present invention, the present invention includes several general and useful aspects, including:

1) a method for enriching a target cell, such as cancer cells, from a biological sample such as a blood sample. When applied to a blood sample, the methods may comprise the selective removal of red blood cells (RBCs) by lysis, and the selective removal of WBCs by binding them to a specific binding member and removing them, such as by precipitation or by allowing them to bind to a solid support via specific binding members. Alternatively, the method may comprise the removal of white blood cells (WBCs) using microparticles to which a specific binding member that is specific for WBCs is affixed, and removal of red blood cells (RBCs) from said blood sample to enrich rare cells with a density-based approach e.g., a ficoll gradient centrifugation. Removal of WBCs and RBCs can be done in either order or both may be removed at the same time.

2) methods and compositions for identifying and characterizing cancer cells in an enriched cancer cell-containing sample obtained from a blood sample, based on the molecular recognition and labeling of selected cancer markers.

3) a method for diagnosing and monitoring cancer disease or its treatment, comprising the measurement of the number or proportion or properties of cancer cells in a blood sample obtained from a subject.

In certain embodiments, the target cell is a cancer cell or a mesenchymal cell, and desirably the cancer or mesenchymal cell is distinguished by the identification methods described herein from any normal epithelial cells in the sample. Frequently, the sample is a blood sample. Note that the methods involve enrichment of a rare cell type that may or may not be present, and the presence, absence, number, proportion, or properties of any rare cells present are usually diagnostic; thus the method is useful regardless of whether or not rare cells are found in the sample. The methods are typically described herein as though the target cell is present, but they are equally useful to detect the absence of a target cell. While the target cell isolation and identification methods described herein are highly specific for the target cells of interest, other cells may also be identified in some samples as target-like; such methods are nevertheless useful for diagnostic and other purposes provided that information about the number or fraction of non-target cells being identified can be determined, as by comparison to samples from subjects having no target cells present. In some embodiments, further characterization methods may be used to reduce the number of target-like cells that are detected along with the target cells.

In some embodiments, the enrichment of the target cell(s) in the sample is achieved in a series of steps. One step in the sequence may be a selective lysis step, which uses osmotic pressure change to selectively lyse certain types of cells, such as red blood cells, without lysing the target cell. That enables the removal of at least one type of non-target cell, so that the remaining cell population in the sample is enriched in the target cell.

Typically, the enrichment of the target cell(s) in the sample involves selective removal of at least one non-target cell type by adhering cells of the non-target type to a solid surface. This can be accomplished by affixing a selective binding member to the solid surface, which selective binding member has a high affinity for a non-target cell type to be removed and has little or no effective affinity for the target cell type. The sample is then exposed to the solid surface having an affixed selective binding member, and at least one non-target cell type is thus removed from the sample, which is thereby enriched in the target cell(s), if any are present.

Frequently, the selective binding member is an antibody or antibody fragment that is selective for a cell surface marker that is associated with a non-target cell and is expected to be absent on the target cells. An example of such markers would be a surface antigen that occurs on one or more types of hematopoietic cells, when the target cell is a non-hematopoietic cell. The solid surface can be a surface of a container that the sample is placed in, or a surface of a swab or other item to be passed through the sample, or it can be a finely divided material such as a bead or gel that can be admixed with the sample. In each case, the sample is exposed to the solid surface for a sufficient period of time to permit binding of the non-target cell type to be removed to the specific binding member; then the sample is separated from the solid surface for further enrichment or analysis. In one preferred embodiment, the solid surface is a plurality of beads, such as magnetic beads, that provide a high surface area for affixing the specific binding member of interest, can be efficiently mixed with the sample to permit binding of the non-target cell to the specific binding material, and can be conveniently separated from the sample to remove the non-target cells.

These aspects of the invention, as well as others described herein, can be achieved by using the methods, articles of manufacture and compositions of matter described herein. It will be further recognized that various aspects of the present invention can be combined to make desirable embodiments of the invention. To gain a full appreciation of the scope of the present invention, certain non-limiting examples are described herein.

I. Method of Enriching Cancer Cells of a Fluid Sample Using Depletion of Red Blood Cells and White Blood Cells.

One aspect of the present invention includes methods and compositions for enriching rare cells or target cells by removal of plasma proteins, RBCs and WBCs from a biological sample by means of combining density based centrifugation and immuno-particle methods to remove non-target cells and to enrich rare cells such as circulating tumor cells, stem cells fetal cells, immune cells, and other rare cells with the following exemplary steps: a) removing WBCs with antibody coated immunoparticles: b) removing RBCs with a density-based approach, and c) performance a subsequent analysis, manipulation or application of the rare cell or target cell. The density-based approach can also be used to remove other materials such as non-cellular debris and proteins from the target cells.

In one specific embodiment, the present method can be used for depletion of plasma proteins, RBCs and WBCs by means of combining density based centrifugation and immuno-particles to enrich rare cells including circulating tumor cells, stem cells, fetal cells, immune cells, and other rare cells from a blood sample.

In some embodiments, the blood sample is collected in any suitable anti-coagulant containing tube, which may optionally also include EDTA, ACD, Heparin, Cyto-chex and similar known materials for stabilizing or preserving the blood sample.

In some embodiments, a density-based centrifugation method is used to remove at least one type of non-target cell. The medium for such density based centrifugation separation could have a range of suitable concentrations to generate same density and/or continuous or discontinuous gradient, polysucrose based reagent such as Ficoll, or any other reagents applied to prepare desired density to separate proteins and or cells by centrifugation.

In a certain embodiment of the present invention, the immuno-particles could be any solid phase particle or microspheres such as magnetic particle, sepharose, sephadex, and agarose etc based particles, and the particles can be chemically modified to conjugate to an antibody or any other specific binding members for selection and binding of non-target cell types to be removed as part of the process for enrichment of the sample in the target cell type of interest.

The enriched cells, and/or separated plasma proteins, and/or white blood cell population are available for various analysis and applications, including immunocytometry, flow cytometry, PCR (e.g., Reverse Transcription-PCR and the real time Reverse Transcription-PCR), image analysis, immunofluorescence, genotyping, gene profiling examination, culturing of enriched cells, mass-spectrometry and other cell and/or protein related studies, cell-based therapy, cell-based assays, enzymatic assays, etc.

One exemplary method for enriching tumor cells from a blood sample is outlined below:

A blood sample is diluted with an equal volume of phosphate buffered saline (PBS) or Hank's buffered saline solution, or any buffer with osmolarity of 270-330 milliosmoles per kilogram (mOsm/kg), or medium such as cell culture medium. 0.1-0.5 ml of antibody-coated immunoparticles is added in diluted blood, followed by gentle shaking at room temperature for 5 minutes or longer. This mixture is subsequently loaded on the top of a separation medium (e.g., Ficoll diluted in a range between 80-98% using above mentioned buffer or medium), followed by centrifugation between 200-800 g for 5 minutes or longer at room temperature. Plasma, white blood cells, and Ficoll at different layers are collected from the top. Either a white blood cell layer or all layers pooled together are centrifuged at 800-1500 g for 5 min or longer. A cell pellet that will contain the target cells if any were present in the sample is prpareds following this procedure and is resuspended and subjected to subsequent analysis.

In one embodiment, the present invention is directed to a method for detecting a non-hematopoietic cancer cell, in a blood sample, which method comprises: a) providing a blood sample; b) removing red blood cells (RBCs) from said blood sample, with a density-based approach, e.g., a Ficoll density centrifugation, and removing white blood cells (WBCs) from said blood sample to enrich a non-hematopoietic cell type, e.g., a non-hematopoietic tumor cell, if any, from said blood sample, with a microparticle-based approach; and c) assessing the presence, absence and/or amount of said enriched non-hematopoietic cell or tumor cell. It is apparent to those skilled in the art that this method is equally useful where the non-target cell happens to be absent from a sample, because the recovery of target cells is sufficiently efficient that the absence of detected target cells is a diagnostically meaningful and useful result, just as the presence or number of target cells is diagnostically useful.

One of the possible alternative methods is achieved by the following steps:

A blood sample is diluted with an equal volume of phosphate buffered saline or Hank's buffered saline solution, or any buffer with osmolarity of 270-330 mOsm/kg, or a medium such as cell culture medium, and subsequently loaded on the top of a density-based separation medium (e.g., Ficoll diluted in a range between 80-98% using above mentioned buffer or medium), followed by centrifugation between 200-800 g for 5 minutes or longer at a convenient temperature such as room temperature. Plasma, white blood cell, and Ficoll at different layers are collected from the top. 0.1-0.5 ml of antibody-coated immunoparticles are added in either white blood cell layer or pooled all layers, followed by gentle shaking for 5 minutes or longer at room temperature. Immunoparticles with bound WBCs are separated by either magnet or centrifugation at 200-800 g for 5 minutes or longer. Collected supernatants are centrifuged again at 800-1500 g for 5 min or longer. The cell pellet from this procedure is resuspended and subjected to subsequent analysis.

The present invention also provides methods and compositions for detecting a non-hematopoietic cell, e.g., a non-hematopoietic cancer cell, in a blood sample. In one embodiment, the present invention is directed to a method for detecting a non-hematopoietic cancer cell, in a blood sample, which method comprises: a) providing a blood sample; b) removing red blood cells (RBCs) from said blood sample, with the proviso that said RBCs are not removed from said blood sample via a centrifugation, e.g., a Ficoll gradient centrifugation, and removing white blood cells (WBCs) from said blood sample to enrich a non-hematopoietic cell, e.g., a non-hematopoietic tumor cell, if any, from said blood sample; and c) assessing the presence, absence and/or amount of said enriched non-hematopoietic cell or tumor cell.

The present method can be used to detect a cancer cell in any suitable sample, and is frequently used to detect circulating tumor or cancer cells in a blood sample or other clinical sample. For example, a sample to be tested can be a whole blood sample or a peripheral blood sample.

The present method can be used to detect any suitable non-hematopoietic cell, e.g., a non-hematopoietic cancer cell, in a blood sample. For example, the non-hematopoietic cell to be detected can be a cancerous cell or a cancer cell. In some embodiments, the method is used to specifically identify cancerous or mesenchymal cells, and to distinguish them from any normal epithelial cells that may be present.

The RBCs can be removed from a blood sample by any suitable methods. For example, the RBCs can be removed by sedimentation, filtration, selective lysis, or binding to a specific binding member that specifically binds RBCs a combination of the above, and/or repetition of the above. In some preferred embodiments, RBCs are removed from a blood sample by lysing them by conventional methods, such as exposing them to a medium or buffer known to selectively lyse RBCs without lysing the target cells of interest.

The WBCs can be removed by any suitable methods. For example, the WBCs can be removed by binding to a specific binding member that specifically binds WBCs, with significantly reduced or no binding to the target cells. Any suitable specific binding members can be used. In one specific embodiment, the specific binding member can be an antibody that specifically binds to a component on the surface of WBCs. Such exemplary antibodies include an antibody that specifically binds to CD3, CD11b, CD14, CD17, CD31, CD34, CD45, CD50, CD53, CD63, CD69, CD81, CD84, CD102 or CD166. In some embodiments, the antibody is one that specifically binds to CD50.

The specific binding member that is used to remove WBCs can be used in a solution or can be bound to a solid surface such as a particle. The specific binding member can be bound directly or indirectly to a solid surface. For example, the specific binding member can be bound indirectly to a solid surface through another binding pair, e.g., a biotin-avidin/strepavidin binding pair. The specific binding member can be bound to a solid surface with or without any prior chemical modification(s) and/or conjugation to any molecules such as a member of separate binding pair. Any suitable solid surface can be used. For example, a specific binding member can be bound to a magnetic particle and the RBCs and/or WBCs bound to the magnetic particle can be removed from a blood sample using a magnetic field or force.

The RBCs and WBCs can be removed from a blood sample in any suitable order. For example, the RBCs can be removed before the WBCs are removed from the blood sample. In another example, the WBCs are removed before the RBCs are removed from the blood sample. In still another example, the RBCs and WBCs can be removed from a blood sample simultaneously.

To further enrich the tumor cells to be assessed, the present methods can further comprise removing a component(s) other than the RBCs and WBCs. For example, the present methods can comprise removing platelets, stem cells, stromal cells, endothelial cells or soluble proteins from the blood sample. The removal of the RBCs and WBCs and the removal of the other undesirable component(s) can be carried out in separate steps or in the same step. Methods for such removal could include those described below as well as others known to those skilled in the art.

A suitable method for enriching tumor cells from a blood sample is outlined below:

A sample of 10 mL of blood, stored at room temperature for up to 7 days, preferably up to 3 days, is transferred to a 50 mL centrifugation tube and the volume is adjusted to 30 mL with a solution consisting of: 5 mM EDTA, 1% BSA in Hanks Balanced Salt Solution (HBSS), and PBS The sample is centrifuged at 1400 rpm for 5 min at room temperature. 23 mL of supernatant are discarded and the pellet is completely resuspended by gentle shaking. An RBC lysis buffer (one liter of 10× stock for this buffer can be made with $NH_4Cl$-82.9 g (Sigma, Cat # A-0171), $KHCO_3$-10 g (Sigma, Cat # 237205-500 g), EDTA-2 ml of 0.5M EDTA (Molecular Probes, Cat # 15575-020), pH 7.2, vacuum filtered) is added (22 mL), and the sample is incubated with rotation at room temperature for about 8 min. Following the lysis of the red blood cells the sample is centrifuged at 1400 rpm for 5 min at room temperature. The supernatant is aspirated, leaving remaining cell pellet undisturbed. The cell pellet is completely resuspended in 45 mL of solution containing 5 mM EDTA, 1% BSA in HBSS, and PBS. The sample is centrifuged again at 1400 rpm for 5 min at room temperature; the supernatant is discarded and the cells are resuspended in 0.3 mL of solution containing 5 mM EDTA, 1% BSA in HBSS, and PBS. The cell suspension is transferred into a 2 ml (U-bottom) eppendorf tube, and 0.8 mL of magnetic beads slurry is added. The beads are coated with antibody recognizing the CD50 antigen. The cells/beads suspension is incubated with gentle rotation for 5 to 60 minutes at room temperature. Following the incubation, the tube is positioned on a magnetic stand at room temperature for 1 min with lead cap open, to allow for the beads and the non-cancer cells adsorbed to the beads to migrate towards the side of the tube facing the magnet. The solution is carefully transferred to a 1.7 mL eppendorf tube (V-bottom). The enriched sample containing the tumor cells is centrifuged at 10,000 rpm for 1 minute. After discarding the supernatant, the cells are resuspendend in 40 μL of PBS buffer.

In a variant of the method described above, the removal of the non-cancer cells is achieved by the following method:

Following the lysis of the red blood cells the sample is centrifuged at 1400 rpm for 5 min at room temperature. The supernatant is aspirated, leaving a remaining cell pellet. The cell pellet is completely resuspended in 45 mL of solution containing 5 mM EDTA, 1% BSA in HBSS, PBS. The sample is centrifuged again at 1400 rpm for 5 min at room temperature; the supernatant is discarded and the cells are resuspended in 0.3 mL of solution containing 5 mM EDTA, 1% BSA in HBSS, and PBS. The cell suspension is transferred into a 2 ml (U-bottom) eppendorf tube and 0.8 mL of magnetic beads slurry is added. The beads are coated with antibodies recognizing CD50, and optionally CD34 and CD31 and CD235a antigens. The cells/beads suspension is incubated with gentle rotation for 5 to 60 minutes at room temperature. Following the incubation, the tube is positioned on a magnetic stand at room temperature for 1 min with lead cap open, to allow for the beads and the hematopoietic cells adsorbed to the beads to migrate towards the side of the tube facing the magnet. The solution is carefully transferred to a 1.7 mL eppendorf tube (V-bottom). The enriched sample is centrifuged at 10,000 rpm for 1 minute. After discarding the supernatant, the cells are re-suspendend in 40 μL of PBS buffer.

Other antibodies that specifically bind to non-target cells likely to be present in the sample can, of course, also be affixed to a surface or bead and similarly used to remove non-target cells and further enrich the sample.

To further enrich the tumor cells to be assessed, the present methods can comprise debulking the blood sample. Any suitable debulking method can be used. For example, the debulking step can comprise a filtration step, a centrifugation step or a selective sedimentation step. This step may be included before or after removal of RBCs, for example, and the process may include more than one such step as needed.

In one preferred embodiment of the present invention the enrichment of the non-hematopoietic cancer cells from a blood sample is performed by an automated instrument. Automated manipulation of biological samples and fluids is most efficiently performed by avoiding centrifugation as a means to debulk the samples, although centrifugation can also be integrated into an automated process.

Figure 1:
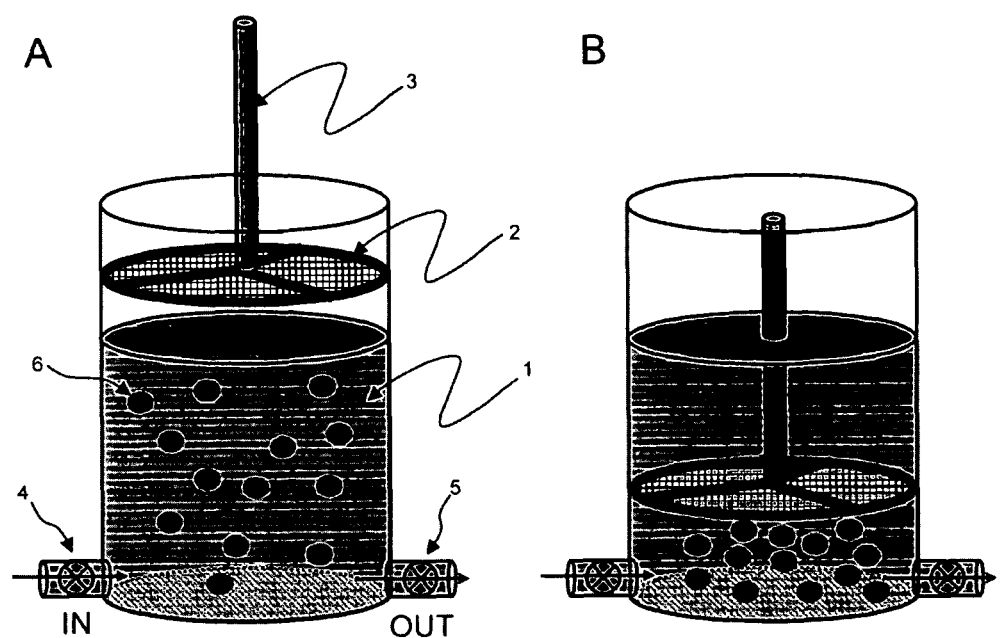
FIG. 1. French press device for cell sample debulking

In one embodiment of the present invention the debulking of the samples is performed using a "French press" device as described in FIG. 1. This method is particularly appropriate for use in an automated system for processing multiple samples, as this debulking process is especially suited to automation. The "French press" device consists of a chamber, which in a preferred embodiment of the invention is of cylindrical shape (1 in FIG. 1), at least one filter (2 in FIG. 1), a piston (3 in FIG. 1), and an inlet and outlet means (4 and 5 in FIG. 1) with valves controlling fluid flow. The filter contains at least one pore and preferably contains a plurality of pores. The pores can be of any shape and any suitable dimensions and cross-sectional shapes. For example, a pore can be quadrilateral, rectangular, ellipsoid, or circular in shape, or of other geometric or non-geometric shape. A pore can have a diameter (or widest dimension) from about 0.1 micron to about 1000 microns, preferably from about 0.2 to about 5 microns, or about 1 to less than 10 microns.

In a preferred embodiment, a pore is made during the machining of a filter, and is micro etched or bored into the filter material that comprises a hard, fluid-impermeable material such as glass, silicon, ceramics, metal or hard plastic such as acrylic, polycarbonate, or polyimide. It is also possible to use a relatively non-hard surface for the filter that is supported on a hard solid support. Another aspect of this invention is to modify the material by methods such as, but not limited to, chemically or thermally modifying the material to silicon oxide, silicon nitride, plastics, or polymers. Preferably, however, the filter comprises a hard material that is not substantially deformable by the pressure used in generating fluid flow through the filter.

Preferably, the filter used for filtration in the present invention is microfabricated or micromachined filters so that the pores within a filter can achieve relatively precise and uniform dimensions. Such precise and uniform pore dimensions are a distinct advantage of the microfabricated or micromachined filters of the present invention, in comparison with the conventional membrane filters made of materials such as nylon, polycarbonate, polyester, mixed cellulose ester, polytetrafluoroethylene, polyethersulfone, etc. In the filters of the present invention, individual pores are isolated, have similar or almost identical feature sizes, and are patterned on a filter. Such filters allow precise separation of particles based on their sizes and other properties.

The filtration area of a filter is determined by the area of the substrate comprising the pores. The filtration area for microfabricated filters of the present invention can be between about 0.01 mm$^2$ and about 0.1 m$^2$. Preferably, the filtration area is between about 0.25 mm$^2$ and about 25 cm$^2$, and more preferably is between about 0.5 mm$^2$ and about 10 cm$^2$. The variations of filtration areas allow the filters of the invention to process sample volumes from about 100 microliters to about 10 liters. The percent of the filtration area encompassed by pores can be from about 1% to about 70%, preferably is from about 10% to about 50%, and more preferably is from about 15 to about 40%. The filtration area of a microfabricated filter of the present invention can comprise any number of pores, and preferably comprises at least two pores, but more preferably the number of pores in the filtration area of a filter of the present invention ranges from about 4 to about 1,000,000, and even more preferably ranges from about 100 to about 250,000. The thickness of the filter in the filtration area can range from about 10 to about 1000 microns, but is preferably in the range of between about 40 and about 500 microns.

The microfabricated filters of the present invention have pores that may be etched through the filter substrate itself. The pores or openings of the filters can be made by using microfabrication or micromachining techniques on substrate materials, including, but not limited to, silicon, silicon dioxide, ceramics, glass, polymers such as polyimide, polyamide, etc. Various fabrication methods, as known to those skilled in the art of microlithography and microfabrication (See, for example, Rai-Choudhury P. (Editor), HANDBOOK OF MICROLITHOGRAPHY, MICROMACHINING AND MICROFABRICATION, Volume 2: Micromachining and microfabrication. SPIE Optical Engineering Press, Bellingham, Wash., USA (1997)), may be used. In many cases, standard microfabrication and micromachining methods and protocols may be involved. One example of suitable fabrication methods is photolithography involving single or multiple photomasks. The protocols in the microfabrication may include many basic steps, for example, photolithographic mask generation, deposition of photoresist, deposition of "sacrificial" material layers, photoresist patterning with masks and developers, or "sacrificial" material layer patterning. Pores can be made by etching into the substrate under certain masking process so that the regions that have been masked are not etched off and the regions that have not been mask-protected are etched off. The etching method can be dry-etching such as deep RIE (reactive ion etching), laser ablation, or can be wet etching involving the use of wet chemicals.

Preferably, appropriate microfabrication or micromachining techniques are chosen to achieve a desired aspect ratio for the filter pores. The aspect ratio refers to the ratio of the pore depth (corresponding to the thickness of the filter in the region of the pores) to the pore diameter. The fabrication of filter pores with higher aspect ratios (i.e., greater pore depth) may involve deep etching methods. Many fabrication methods, such as deep RIE, useful for the fabrication of MEMS (micro electronic mechanical systems) devices can be used or employed in making the microfabricated filters. The resulting pores can, as a result of the high aspect ratio and the etching method, have a slight tapering, such that their openings are narrower on one side of the filter than the other.

The present invention includes microfabricated filters comprising two or more tapered pores. The substrate on which the filter pores, slots or openings are fabricated or machined may be silicon, silicon dioxide, plastic, glass, ceramics or other solid materials. The solid materials may be porous or non-porous. Those who are skilled in microfabrication and micromachining fabrication may readily choose and determine the fabrication protocols and materials to be used for fabrication of particular filter geometries.

Using the microfabrication or micromachining methods, the filter slots, pores or openings can be made with precise geometries, and with substantially similar sizes. Depending on the fabrication methods or materials used, the accuracy of a single dimension of the filter slots (e.g. slot length, slot width) can be within 20%, or less than 10%, or less than 5%. Thus, the accuracy of the critical, single dimension of the filter pores (e.g. slot width for oblong or quadrilateral shaped slots) for the filters of the present invention are made with a size variation of, preferably, less than 2 microns, more preferably, less than 1 micron, or even more preferably less than 0.5 micron.

Preferably, filters of the present invention can be made using the track-etch technique, in which filters made of glass, silicon, silicon dioxides, or polymers such as polycarbonate or polyester with discrete pores having relatively-uniform pore sizes are made. For example, the filter can be made by adapting and applying the track-etch technique described at whatman<dot>com/products/nucleopore/tech frame<dot>htm for Nucleopore Track-etch membranes to filter substrates. In the technique used to make membrane filters, a thin polymer film is tracked with energetic heavy ions to produce latent tracks on the film. The film is then put in an etchant to produce pores, which etchant is frequently a caustic solution, but may be other etchants known in the art.

Preferred filters for the cell separation methods and systems of the present invention include microfabricated or micromachined filters that can be made with precise geometries for the openings on the filters. Individual openings are isolated with similar or almost identical feature sizes and are patterned on a filter. The openings can be of different shapes such as, for example, circular, quadrilateral, or elliptical. Such filters allow precise separation of particles based on their sizes and other properties.

In a preferred embodiment of a microfabricated filter, individual pores are isolated and of a cylindrical shape, i.e., they are substantially circular in one cross section parallel to the plane of the filter, and substantially rectangular in cross-section in the other direction, perpendicular to the filter, and the pore sizes in a filter are typically within a 20% variation, where the pore size is calculated by the smallest and largest dimension of the pore's cross-section (width and length, respectively).

The present invention also includes methods of treating a microfabricated filter to improve its filtering efficiency. In these methods, one or both surfaces of the filter is treated or coated or modified to increase its filtering efficiency. In a preferred method, one or both surfaces of the filter is treated or modified to reduce the possibility of sample components (such as but not limited to cells) interacting with or adhering to the filter.

A filter can be physically or chemically treated, for example, to alter its surface properties (e.g. hydrophobic, hydrophilic). For example, a filter can be heated or treated with oxygen plasma, modified to silicon nitride or can be treated with at least one acid or at least one base, to increase its hydrophilicity or surface charge. For example, a glass or silica filter can be heated to oxidize the surface of the filter. Heating times and temperatures can vary depending on the filter material and the degree of oxidation desired. In one example, a glass filter can be heated to a temperature of from about 200 to 1000 degrees Celsius for from about thirty minutes to twenty-four hours.

In another example, a filter can be treated with one or more acids or one or more bases to increase the hydrophilicity of the filter surface. In preferred embodiments, a filter that comprises glass or silica is treated with at least one acid.

An acid used in treating a filter of the present invention can be any acid. As nonlimiting examples, the acid can be HCl, $H_2SO_4$, $NaHSO_4$, $HSO_4$, $HNO_3$, HF, $H_3PO_4$, HBr, HCOOH, or $CH_3COOH$. The acid can be of a concentration about 0.1 N or greater, and preferably is about 0.5 N or higher in concentration, and more preferably is greater than about 1 N in concentration. For example, the concentration of acid preferably is from about 1 N to about 10 N. The incubation time can be from one minute to days, but preferably is from about 5 minutes to about 2 hours.

Optimal concentrations and incubation times for treating a microfabricated filter to increase its hydrophilicity can be determined empirically. The microfabricated filter can be placed in a solution of acid for any length of time, preferably for more than one minute, and more preferably for more than about five minutes. Acid treatment can be done under any non-freezing and non-boiling temperature, preferably at a temperature greater than or equal to room temperature.

Alternatively or in addition, a microfabricated filter of the present invention can be treated with a base, such as a basic solution, that can comprise, as nonlimiting examples, NaOH, KOH, $Ba(OH)_2$, LiOH, CsOH, or $Ca(OH)_2$. The basic solution can be of a concentration of about 0.01 N or greater, and preferably is greater than about 0.05 N, and more preferably greater than about 0.1 N in concentration. The ion transport measuring means can be placed in a solution of base for any length of time, preferably for more than one minute, and more preferably for more than about five minutes. Base treatment can be done under any non-frozen and non-boiling temperature, preferably at a temperature greater than or equal to room temperature.

The effectiveness of a physical or chemical treatment in increasing the hydrophilicity of a filter surface can be tested by measuring the spread of a drop of water placed on the surface of a treated and non-treated filter, where increased spreading of a drop of uniform volume indicates increased hydrophilicity of a surface. The effectiveness of a filter treatment can also be tested by incubating a treated filter with cells or biological samples to determine the degree of sample component adhesion to the treated filter.

In another embodiment, the surface of a filter, such as but not limited to a polymeric filter, can be chemically treated to alter the surface properties of the filter. For example, the surface of a glass, silica, or polymeric filter can be derivatized by any of various chemical treatments to add chemical groups that can decrease the interaction of sample components with the filter surface One or more compounds can also be adsorbed onto or conjugated to the surface of a microfabricated filter made of any suitable material, such as, for example, one or more metals, one or more ceramics, one or more polymers, glass, silica, silicon dioxide, or combinations thereof. In preferred embodiments of the present invention, the surface or surfaces of a microfabricated filter of the present invention is coated with a compound to increase the efficiency of filtration by reducing the interaction of sample components with the filter surface.

For example, the surface of a filter can be coated with a molecule, such as, but not limited to, a protein, peptide, or polymer, including naturally occurring or synthetic polymers. The material used to coat the filter is preferably biocompatible, meaning it does not have deleterious effects on cells or other components of biological samples, such as proteins, nucleic acids, etc. Albumin proteins, such as bovine serum albumin (BSA) are examples of proteins that can be used to coat a microfabricated filter of the present invention. Polymers used to coat a filter can be any polymer that does not promote cell sticking to the filter, for example, nonhydrophobic polymers such as, but not limited to, polyethylene glycol (PEG), polyvinylacetate (PVA), and polyvinylpyrrolidone (PVP), and a cellulose or cellulose-like derivative.

A filter made of, forx example, metal, ceramics, a polymer, glass, or silica can be coated with a compound by any feasible means, such as, for example, adsorption or chemical conjugation.

In many cases, it can be advantageous to surface-treat the filter prior to coating with a compound or polymer. Surface treatment can increase the stability and uniformity of the coating. For example, a filter can be treated with at least one acid or at least one base, or with at least one acid and at least one base which can be applied in either order, prior to coating the filter with a compound or polymer. In preferred aspects of the present invention, a filter made of a polymer, glass, or silica is treated with at least one acid and then incubated in a solution of the coating compound for a period of time ranging from minutes to days. For example, a glass filter can be incubated in acid, rinsed with water, and then incubated in a solution of BSA, PEG, or PVP.

In some aspects of the present invention, it can be preferred to rinse the filter, such as in water (for example, deionized water) or a buffered solution before acid or base treatment or treatment with an oxidizing agent, and, preferably again before coating the filter with a compound or polymer. Where more than one type of treatment is performed on a microfabricated filter, rinses can also be performed between treatments, for example, between treatment with an oxidizing agent and an acid, or between treatment with an acid and a base. A filter can be rinsed in water or an aqueous solution that has a pH of between about 3.5 and about 10.5, and more preferably between about 5 and about 9. Non-limiting examples of suitable aqueous solutions for rinsing ion transport measuring means can include salt solutions (where salt solutions can range in concentration from the micromolar range to 5M or more), biological buffer solutions, cell media, or dilutions or combinations thereof. Rinsing can be performed for any length of time, for example from minutes to hours.

The concentration of a compound or polymer solution used to coat a filter can vary from about 0.02% to 20% or more, and will depend in part on the compound used. The incubation in coating solution can be from minutes to days, and preferably is from about 10 minutes to two hours.

After coating, the filter can be rinsed in water or a buffer.

In one preferred embodiment of the present invention the filter has a diameter of 50 to 99.9% of the diameter of the filtration chamber. The space located between the edge of the filter and the walls of the filtration chambers is occupied by, for example, an O-ring or similar sealing member that is attached to the outer edge of the filter. The O-ring provides a tight seal between the filter and the wall of the filtration chamber to prevent cells from bypassing the filter during operation.

In the present invention the filter can be positioned at different heights inside the filtration chamber, by means of positive or negative pressure applied to a piston, which is connected to the filter.

A method for debulking a biological sample, for example a blood sample containing cancer cells, utilizing an automated instrument containing the french press filtration chamber of the present invention is outlined below:

A sample of 10 mL of blood, stored at room temperature for up to 4 days, is transferred to a 50 mL centrifugation tube and the volume is adjusted to 30 mL with a solution consisting of: 5 mM EDTA, 1% BSA in HBSS, PBS. A conduit automatically transfers the 30 mL of solution sample to the line connected to the inlet of the filtration chamber. After filling of the filtration chamber with the fluid sample, the valve controlling flow through the inlet is closed. Positive pressure is applied on the piston, which lowers the position of the filter (FIG. 1, B). Positive pressure on the piston is adjusted to reach a filtration rate of the fluid sample of 0.1 to 50 mL per minute. The filter is lowered until 80 to 95% of the fluid in the filtration chamber is above the filter. The solution below the filter contains the cancer cells and other non-cancer cells and constitutes the de-bulked sample.

The surface treatment methods of the present invention can also be applied to components to be used for manipulation of biological samples such as chips other than those that comprise pores for filtration. For example, chips that comprise metals, ceramics, one or more polymers, silicon, silicon dioxide, or glass can be physically or chemically treated using the methods of the present invention. Such chips can be used, for example, in separation, analysis, and detection devices in which biological species such as cells are separated, detected, or analyzed. The treatment of the chip can enhance or reduce the interaction of the cells with the chip surface, depending of the treatment used, the properties of the cells being manipulated, and the nature of the manipulation. For example, coating the surface of the chip with a hydrophilic polymer (for example but not limited to coating the chip with PVP or PVA) may reduce or minimize the interaction between the surface of the chip and the cells.

In some preferred embodiments of the present invention the cells obtained from the enrichment procedures can be detected, analyzed or manipulated by means of active force chips.

In some preferred embodiments, traveling-wave dielectrophoretic forces can be generated by electrodes built onto a chip and can be used to move cells to different compartments. A full description of the traveling wave dielectrophoresis is provided in U.S. application Ser. No. 09/679,024, entitled "Apparatuses Containing Multiple Active Force Generating Elements and Uses Thereof" filed Oct. 4, 2000, herein incorporated by reference in its entirety.

One problem encountered with a filtration device such as that depicted in FIG. 1 is that cells in the sample may enter or even plug the holes in the filter as the filter advances into the sample. This can result in loss of or damage to the cells, or in plugging of the filter. One aspect of the present invention addresses this problem by providing means to repel cells from the filter surface. The following discussion and references can provide a framework for the design and use of electrodes to facilitate filtration by translocating sample components, such as nonfilterable cells, away from a filter using a repulsive force.

Dielectrophoresis refers to the movement of polarized particles in a non-uniform AC electrical field. When a particle is placed in an electrical field, if the dielectric properties of the particle and its surrounding medium are different, the particle will experience dielectric polarization. Thus, electrical charges are induced at the particle/medium interface. If the applied field is non-uniform, then the interaction between the non-uniform field and the induced polarization charges will produce net force acting on the particle to cause particle motion towards the region of strong or weak field intensity. The net force acting on the particle is called dielectrophoretic force and the particle motion is dielectrophoresis. Dielectrophoretic force depends on the dielectric properties of the particles, particle surrounding medium, the frequency of the applied electrical field and the field distribution.

Traveling-wave dielectrophoresis is similar to dielectrophoresis in which the traveling-electric field interacts with the field-induced polarization and generates electrical forces acting on the particles. Particles are caused to move either with or against the direction of the traveling field. Traveling-wave dielectrophoretic forces depend on the dielectric properties of the particles and their suspending medium, the frequency and the magnitude of the traveling-field. The theory for dielectrophoresis and traveling-wave dielectrophoresis and the use of dielectrophoresis for manipulation and processing of microparticles may be found in various publications (e.g., "Non-uniform Spatial Distributions of Both the Magnitude and Phase of AC Electric Fields determine Dielectrophoretic Forces by Wang et al., in *Biochim Biophys Acta* Vol. 1243, 1995, pages 185-194", "Dielectrophoretic Manipulation of Particles" by Wang et al, in IEEE Transaction on Industry Applications, Vol. 33, No. 3, May/June, 1997, pages 660-669, "Electrokinetic behavior of colloidal particles in traveling electric fields: studies using yeast cells" by Huang et al, in J. Phys. D: Appl. Phys., Vol. 26, pages 1528-1535, "Positioning and manipulation of cells and microparticles using miniaturized electric field traps and traveling waves" By Fuhr et al., in Sensors and Materials. Vol. 7: pages 131-146, "Dielectrophoretic manipulation of cells using spiral electrodes" by Wang, X-B. et al., in *Biophys. J*. Volume 72, pages 1887-1899, 1997, "Separation of human breast cancer cells from blood by differential dielectric affinity" by Becker et al, in Proc. Natl. Acad. Sci., Vol., 92, January 1995, pages 860-864).

The manipulation of microparticles with dielectrophoresis and traveling wave dielectrophoresis include concentration/aggregation, trapping, repulsion, linear or other directed motion, levitation, separation of particles. Particles may be focused, enriched and trapped in specific regions of the electrode reaction chamber. Particles may be separated into different subpopulations over a microscopic scale. Relevant to the filtration methods of the present invention, particles may be transported over certain distances. The electrical field distribution necessary for specific particle manipulation depends on the dimension and geometry of microelectrode structures and may be designed using dielectrophoresis theory and electrical field simulation methods.

The dielectrophoretic force $F_{DEP_z}$ acting on a particle of radius r subjected to a non-uniform electrical field can be given by $$F_{DEP_z} = 2\pi \in_m r^3 \chi_{DEP} \nabla E_{rms}^2 \cdot \vec{a}_z$$

where $E_{rms}$ is the RMS value of the field strength, $\in_m$ is the dielectric permitivity of the medium. $\chi_{DEP}$ is the particle dielectric polarization factor or dielectrophoresis polarization factor, given by $$\chi_{DEP} = \text{Re}\left(\frac{\varepsilon_p^* - \varepsilon_m^*}{\varepsilon_p^* + 2\varepsilon_m^*}\right),$$

"Re" refers to the real part of the "complex number". The symbol $$\varepsilon_x^* = \varepsilon_x - j\frac{\sigma_x}{2\pi f}$$

is the complex permitivity (of the particle x=p, and the medium x=m). The parameters $\in_p$ and $\sigma_p$ are the effective permitivity and conductivity of the particle, respectively. These parameters may be frequency dependent. For example, a typical biological cell will have frequency dependent, effective conductivity and permitivity, at least, because of cytoplasm membrane polarization.

The above equation for the dielectrophoretic force can also be written as $$F_{DEP_z} = 2\pi \in_m r^3 \chi_{DEP} V^2 p(z) \vec{a}_z$$

where p(z) is the square-field distribution for a unit-voltage excitation (V=1 V) on the electrodes, V is the applied voltage.

There are generally two types of dielectrophoresis, positive dielectrophoresis and negative dielectrophoresis. In positive dielectrophoresis, particles are moved by dielectrophoresis forces towards the strong field regions. In negative dielectrophoresis, particles are moved by dielectrophoresis forces towards weak field regions. Whether particles exhibit positive or negative dielectrophoresis depends on whether particles are more or less polarizable than the surrounding medium. In the filtration methods of the present invention, electrode patterns on one or more filters of a filtration chamber can be designed to cause sample components such as cells to exhibit negative dielectrophoresis, resulting in sample components such as cells being repelled away from the electrodes on the filter surfaces.

Traveling-wave DEP force refers to the force that is generated on particles or molecules due to a traveling-wave electric field. A traveling-wave electric field is characterized by the non-uniform distribution of the phase values of AC electric field components.

Here we analyze the traveling-wave DEP force for an ideal traveling-wave field. The dielectrophoretic force $F_{DEP}$ acting on a particle of radius r subjected to a traveling-wave electrical field $E_{TWD} = E \cos(2\pi(ft - z/\lambda_0))\vec{a}_x$ (i.e., a x-direction field is traveling along the z-direction) is given by $$F_{TWD} = -2\pi \in_m r^3 \xi_{TWD} E^2 \cdot \vec{a}_z$$

where E is the magnitude of the field strength, $\in_m$ is the dielectric permittivity of the medium. $\xi_{TWD}$ is the particle polarization factor, given by $$\zeta_{TWD} = \text{Im}\left(\frac{\varepsilon_p^* - \varepsilon_m^*}{\varepsilon_p^* + 2\varepsilon_m^*}\right),$$

"Im" refers to the imaginary part of the "complex number". The symbol $$\varepsilon_x^* = \varepsilon_x - j\frac{\sigma_x}{2\pi f}$$

is the complex permittivity (of the particle x=p, and the medium x=m). The parameters $\in_p$ and $\sigma_p$ are the effective permittivity and conductivity of the particle, respectively. These parameters may be frequency dependent.

Particles such as biological cells having different dielectric property (as defined by permittivity and conductivity) will experience different dielectrophoretic forces. For traveling-wave DEP manipulation of particles (including biological cells), traveling-wave DEP forces acting on a particle of 10 micron in diameter can vary somewhere between 0.01 and 10000 pN.

A traveling wave electric field can be established by applying appropriate AC signals to the microelectrodes appropriately arranged on a chip. For generating a traveling-wave-electric field, it is necessary to apply at least three types of electrical signals each having a different phase value. An example to produce a traveling wave electric field is to use four phase-quardrature signals (0, 90, 180 and 270 degrees) to energize four linear, parallel electrodes patterned on the chip surfaces. Such four electrodes form a basic, repeating unit. Depending on the applications, there may be more than two such units that are located next to each other. This will produce a traveling-electric field in the spaces above or near the electrodes. As long as electrode elements are arranged following certain spatially sequential orders, applying phase-sequenced signals will result in establishing traveling electrical fields in the region close to the electrodes.

Both dielectrophoresis and traveling-wave dielectrophoresis forces acting on particles depend on not only the field distributions (e.g., the magnitude, frequency and phase distribution of electrical field components; the modulation of the field for magnitude and/or frequency) but also the dielectric properties of the particles and the medium in which particles are suspended or placed. For dielectrophoresis, if particles are more polarizable than the medium (e.g., having larger conductivities and/or permitivities depending on the applied frequency), particles will experience positive dielectrophoresis forces and are directed towards the strong field regions. The particles that are less polarizable than the surrounding medium will experience negative dielectrophoresis forces and are directed towards the weak field regions. For traveling wave dielectrophoresis, particles may experience dielectrophoresis forces that drive them in the same direction as the field traveling direction or against it, dependent on the polarization factor $\xi_{TWD}$. The following papers provide basic theories and practices for dielectrophoresis and traveling-wave-dielectrophoresis: Huang, et al, *J. Phys. D: Appl. Phys.* 26:1528-1535 (1993); Wang, et al, *Biochim. Biophys. Acta.* 1243:185-194 (1995); Wang, et al., *IEEE Trans. Ind. Appl.* 33:660-669 (1997).

Thus a filter for use in the methods described herein can advantageously include one or more electrodes such as the patterned electrodes described above. The electrode(s) may be on a surface of the filter for a press such as the one depicted in FIG. 1; typically, one or more electrodes would be placed on the surface of the filter facing the sample to be debulked, and the electrodes would be turned on before and optionally during the time period in which the filter is advanced into the sample. However, the electrode(s) may also be contained within a material used to construct the filter or on the face of the filtration material from the sample, provided the electrodes produce sufficient dielectrophoretic force on cells in the sample to be debulked so that at least some of the cells, preferably including the target cells, are repelled from the filter. The electrodes thus repel cells from the filter surface and permit filtration to be more effective and less likely to cause damage to or loss of the target cells.

Various combinations of the above enrichment methods can of course be used, as those skilled in the art will appreciate, depending upon the volume and nature of the sample to be enriched, and depending upon the type of cells to be enriched and to be removed. The target cells obtained at the end of the enrichment protocol described in the present invention can be further purified from other non-target cells present in the sample by an additional positive selection step, or they may be characterized before further enrichment occurs.

In many embodiments of the present invention, the target cells are isolated as intact, viable cells that can be grown in culture for further characterization and use. In one preferred embodiment of the present invention, cancer cells obtained by enrichment methods such as those described herein are grown in culture in artificial nutrients following their enrichment from a cancer patient blood sample. This permits the user to identify a preferred therapeutic protocol based on the specific cells to be targeted by observing how the particular cells react to various proposed treatments, for example, or to use the enriched cancer cells in other ways such as in screening drug candidates to determine which types of cancers they are likely to treat.

A method for growing tumor cells obtained from a blood sample is outlined below. A sample of 10 mL of blood, stored at room temperature for up to 4 days, is transferred to a 50 mL centrifugation tube and the volume is adjusted to 30 mL with a solution consisting of: 5 mM EDTA, 1% BSA in HBSS, and PBS or HBSS. The sample is centrifuged at 1400 rpm for 5 min at room temperature. 23 mL of supernatant are discarded and the pellet is completely resuspended by gentle shaking. An RBC lysis buffer is added (22 mL), and the sample is incubated with rotation at room temperature for about 8 min. Following the lysis of the red blood cells the sample is centrifuged at 1400 rpm for 5 min at room temperature. The supernatant is aspirated, leaving the remaining cell pellet undisturbed. The cell pellet is completely resuspended in 45 mL of solution containing 5 mM EDTA, 1% BSA in HBSS, and PBS. The sample is centrifuged again at 1400 rpm for 5 min at room temperature; the supernatant is discarded and the cells are resuspended in 0.3 mL of solution containing 5 mM EDTA, 1% BSA in HBSS, and PBS. The cell suspension is transferred into a 2 ml (U-bottom) eppendorf tube and 0.8 mL of AVIVA beads slurry is added. The beads are coated with antibody recognizing the CD50 antigen. The cells/beads suspension is incubated with gentle rotation for 20 minutes at room temperature. Following the incubation, the tubes are positioned on a magnetic stand at room temperature for 1 min with lead cap open, to allow for the beads and the non-cancer cells adsorbed to the beads to migrate towards the side of the tube facing the magnet. The solution is carefully transferred to a 1.7 mL eppendorf tube (V-bottom). The enriched cells are centrifuged at 10,000 rpm for 1 minute. After discarding the supernatant the cells are resuspended in 0.5 mL of growth media containing RPMI-1640, and DMEM-High Glucose. The cells suspension is then transferred to a microtiter plate or artificial growth matrix and incubated at 37° C. and 5% $CO_2$ to allow cell growth.

In some preferred embodiments of the present invention the cultured cancer cells isolated from a cancer patient are used as a substrate for testing the anti-cancer activity of drugs. This enables the user to identify a suitable chemotherapy protocol for the particular cancer. A method for testing the anticancer activity of drugs on cancer cells from a cancer patient is outlined below:

One or more cancer cells isolated from a cancer patient utilizing the method of the present invention are aliquoted into multiple separated compartments in a microtiter plate. The cells are grown for an appropriate amount of time from about 1 hour to 50 days, preferably 124 to 336 hours. Following the growth period, one specific anti-cancer candidate, which may be a single drug or a mixture of drugs, is added in each compartment containing the cancer cells, and at least one compartment contains a control solution which does not contain drugs. Cells are grown in the presence of the anti-cancer candidate(s) for an appropriate amount of time from about 1 hour to 5 days. The anti-cancer candidates are scored for their ability to induce cellular changes, which may take the form of: apoptosis, necrosis, cytotoxicity, reduced stemness, cell death, inhibition of cell growth, and/or inhibition of cell division of the cancer cells.

To those skilled in the arts it will be evident that the anti-cancer candidate can be tested at several different concentrations on these cultured cancer cells or on cells actually isolated from a cancer patient, in order to provide guidance on the dosage of the drug to be administered to the patient.

II. Method of Detection of Cancer Cells Obtained from a Blood Sample.

Once a sample has been enriched with a target non-hematopoietic cell type, the presence, absence and/or amount of the enriched target cell in the sample, e.g., a non-hematopoietic cancer cell, can be assessed by a number of methods. In one example, the presence, absence and/or amount of the enriched non-hematopoietic cell or tumor cell can be assessed by labeling the enriched non-hematopoietic cell or tumor cell and identifying the labeled non-hematopoietic cell or tumor cell. The enriched non-hematopoietic cell or tumor cell can be labeled using any suitable methods, e.g., immunostaining, DNA content measurement, in situ PCR, in situ hybridization, fluorescence in situ hybridization (FISH), staining by a labeled binding member that specifically binds to the enriched non-hematopoietic cell or tumor cell. The labeled non-hematopoietic cell tumor cell can be identified and characterized by any suitable methods, e.g., microscopic analysis, and/or flowcytometry as well as laser based quantitative microscopy technology such as laser scanning cytometry. In one specific embodiment, the labeled non-hematopoietic cell, or tumor cell, is identified and characterized by cell counting, after the target cells have been labeled, typically using one or more immunostaining methods.

Labeling of the target cells is often accomplished with an immunological labeling method, such as attaching a fluorescence label to the cells using an antibody specific for a marker present on the surface of the target cells. The label can be linked to the antibody, or a first antibody specific for the targeted cells can be allowed to bind to the cells, and subsequently the first antibody can be labeled by allowing a second labeled antibody that is specific for the first antibody to bind to the first antibody that is bound to the target cells. To clearly identify the target cells, more than one labeling process may be used. For example, the cells may be labeled with a first labeling method that identifies the target cell as a non-hematopoietic cell and with a second antibody that identifies the cell as a mutated cell, or as a cell from a particular tissue, etc. A combination of labeling processes may include negative and/or positive labeling processes, i.e., labels that specifically bind to the target cells would be considered a positive labeling process, while labels that specifically bind to non-target cells and allow them to be distinguished from the target cells would be considered a negative labeling process. Thus a set of two or more labeling methods may be used to label the target cell and/or other cells present to unambiguously distinguish the target cell as a cancer cell, for example.

A critical aspect of the present invention is the selection of a plurality of antigens that are used as selective target cells markers and allow for the identification of target cells, such as cancer cells, with increased specificity, and in particular for distinguishing a cancer cell from a non-cancerous circulating epithelial cell in a blood sample, for example. In the present invention combinations of two or more of the following markers can be used for differentiating between cancer cells enriched from a cancer patient blood sample and the background of non-neoplastic cells: ACPP, AFP, albumin, ALCAM, AMAS, ARF6, ARMCX3, ATP1A1, BAG1, BJ-TSA-9, blc-2 βHCG, CA125, CA15-3, CA19-9, Cathepsin B1, CD44, CD44v6, CD56, CD66a, CD66b, CD66c, CD66d, CD66e, CD66f, CD147, CDH2, CDK4I, CDKN2A, CDX2, CEA, CLDN3, CLDN4, CLDN5, c-met, CST3, Cytokeratins, CK18, CK19, CK20, Desmoplakin-3, EAG1, EGFR, EGP2, EMA, ErbB2, ESR1, FAK, FOXA2, GalNac-T, GCT-FTI5, GFAP, Haptoglobin-α, HCA, hCASK, HE4, HEPA1, hERG, HIP-1, HMB45, HSPA2, IGFR, IVL, KCNK-9, KHDRBS3, Ki67, Kv1.3, LAMB2, Lewis-Y antigen, LIMA, LM06, LUNX, MAGE-3, MAGE-A3, mammoglobin, Maspin, Melan-A, MITF, MPP5, MPST, MUC-1, MUC5AC, NCAM-1, NSDHL, Oct4, OTC, p53, p97, p1B, PCNA, PGR, PMSA, PS-2, PSA, RPS6KA5, S100, S100A1, S100A2, S100B, SLC2A1, Smoothelin, SP-1, SPARC, Surfactant, Telomerase, TFAP2A, TITF1 (TTF1), TFF2, TRAIL, TRIM28, TRPM-8, TYR, Tyrosinase, TYRP1, Ubiquitin thiolesterase, VEGF, WT1, X-protein, ZNF165. In the embodiments where a multiplicity of specific binding members is used, each binding member might carry none, the same, or different labels. Using suitable combinations of two or more of such markers, cancerous cells can be distinguished from normal epithelial cells that may be present with at least 50% reliability, and preferably with at least about 70% reliability. In certain embodiments, the combination of markers distinguishes a cancer cell from a normal epithelial cell at least 80% of the time, which provides suitable specificity to enhance the diagnostic value of the methods.

The cancer cell enrichment method of the present invention can provide a sample in which a mixture of cancer cells and non-cancer cells are present. Final and unequivocal identification of the cancer cells, which can include enumeration of total cancer cells, identification of tissue origin of the cells, and/or genotypic characterization of the cells, is often achieved by labeling of said cancer cells. The specific labeling of the cancer cells can be achieved using suitable immunostaining methods well known to those individuals versed in the arts. As an example of a suitable procedure, the cells can be stained as outlined below:

A sample of enriched cells is transferred to a surface and air-dried. This may be done by centrifugation of the enriched sample to provide a cell pellet, which is then transferred to a suitable surface for analysis, such as a plastic or glass microscope slide. The cells are then washed once with 20 mL of PBS for 5 min and subsequently fixed with 2% PFA (paraformaldehyde) in PBS for 40 min at room temperature. After rinsing with PBS three times, the cells are permeabilized by incubation in 0.1% Triton X-100 dissolved in PBS for 5 min. The cells are then rinsed three times with PBS for 5 minutes. Cells are incubated for 1 hr at room temperature in 0.2% BSA-PBS with monoclonal antibodies against one or more of a selected list of markers at dilutions of 1:50-1:100. After rinsing three times for 5 min., the cells are incubated with Alexa-labeled secondary antibody, in 0.2% BSA-PBS at room temperature for 1 hr in the dark. After rinsing the glass slides three times with 0.2% BSA and PBS for a total of 10 minutes, the cells are stained with Hematoxylin for 1 min. Cells are subsequently rinsed in PBS for 1 min, changing PBS twice, and mounted with mounting medium (10 μL).

In one embodiment of the present invention, following the enrichment protocol the cancer cells are positively identified as cells labeled by binding members recognizing one, or two, or three or more of the markers listed below, and optionally also by specific morphological criteria related to the diameter of its nucleus, shape of the nucleus, diameter of the whole cell, or the ratio of the cytoplasmic portion of the cells to its nucleus. The cancer cell marker may include one or more of the following: ACPP, AFP, albumin, ALCAM, AMAS, ARF6, ARMCX3, ATP1A1, BAG1, BJ-TSA-9, blc-2 βHCG, CA125, CA15-3, CA19-9, Cathepsin B1, CD44, CD44v6, CD56, CD66a, CD66b, CD66c, CD66d, CD66e, CD66f, CD147, CDH2, CDK4I, CDKN2A, CDX2, CEA, CLDN3, CLDN4, CLDN5, c-met, CST3, Cytokeratins, CK18, CK19, CK20, Desmoplakin-3, EAG1, EGFR, EGP2, EMA, ErbB2, ESR1, FAK, FOXA2, GalNac-T, GCTFTI5, GFAP, Haptoglobin-α, HCA, hCASK, HE4, HEPA1, hERG, HIP-1, HMB45, HSPA2, IGFR, IVL, KCNK-9, KHDRBS3, Ki67, Kv1.3, LAMB2, Lewis-Y antigen, LIMA, LM06, LUNX, MAGE-3, MAGE-A3, mammoglobin, Maspin, Melan-A, MITF, MPP5, MPST, MUC-1, MUC5AC, NCAM-1, NSDHL, Oct4, OTC, p53, p97, p1B, PCNA, PGR, PMSA, PS-2, PSA, RPS6KA5, S100, S100A1, S100A2, S100B, SLC2A1, Smoothelin, SP-1, SPARC, Surfactant, Telomerase, TFAP2A, TITF1 (TTF1), TFF2, TRAIL, TRIM28, TRPM-8, TYR, Tyrosinase, TYRP1, Ubiquitin thiolesterase, VEGF, WT1, X-protein, ZNF165. Instead of or in addition to the above markers, morphological criteria used to further identify the cancer cells include the following: a) cell nucleus having a diameter larger than a statistically pre-determined value, b) cytoplasm diameter to nucleus diameter ratio between 1.01 and 20, c) overall cell diameter between 3 and 50 uM.

One important difference between normal cells and cancer cells is that normal cells only divide for a limited number of times while cancer cells can continue to divide almost indefinitely. The aging of normal cells is not determined by chronological time but a sort of internal clock which tracks the number of cell divisions. Evidence has accumulated in recent years that one way cells track the number of cell division is the progressive shortening of the chromosomes ends (telomeres) which is a byproduct of each cell division. Telomerase is an enzyme capable of restoring the length of telomeres and can "reset" the biological clock, which measures cell age. In normal cells, however, the expression and activity of telomerase are extremely low, which leads to cell senescence after a finite number of cell divisions. On the contrary, in the majority of cancers, the cells express significant amounts of telomerase and the high level of telomerase activity allows these cells to maintain a constant length of their telomeres and stop the clock that measures aging.

In one aspect of the present invention, the presence or the growth and metastatic potential of cancer cells isolated from the blood of cancer patients is measured by determining the level of expression and/or the function of telomerase in said cancer cells. The enrichment of the cancer cells from the patient sample prior to performing the telomerase detection can significantly improve the sensitivity of the assay. The cancer cells can be isolated from a patient sample, like a blood sample, following a positive selection method like the one described by Griwatz and colleagues (Griwatz C., Brandt B., Assmann G., Zanker K. S., *Journal of Immunological Methods,* 183 (1995) 251-265). Other enrichment methods known to those skilled in the arts can also be used to isolate the cancer cells from the patient sample, prior to performing telomerase detection; or the sample containing the cells can be enriched by the methods described herein. Optionally, enrichment by methods such as those described herein can be combined with a positive selection step. Following the isolation of the cancer cells or the enrichment of the sample, telomerase can be detected in the cancer cells or enriched sample by using a telomerase activity assay like telomerase repeat amplification protocol (TRAP) or using immunodetection methods based on antibodies or other ligands with specific affinity for telomerase to detect the protein itself. The level of telomerase or of its activity in the sample, or the level of a telomerase-encoding nucleic acid or the level of the expression of such nucleic acid in the sample, can be used to determine the probability that the sample contained a cancer cell, or to predict the aggressiveness of the tumor or its likelihood of metastasis, or to determine the number or proportion of cancer cells in the blood sample.

In one preferred embodiment of the present invention the presence or the growth and metastatic potential of cancer cells isolated from the blood of cancer patients is measured by determining the level of expression and/or the function of telomerase in said cancer cells. The cancer cells are isolated from a patient's sample using the depletion methods described in the present invention. Following the isolation or the enrichment of the cancer cells telomerase can be detected in the cancer cells in the sample using telomerase activity assay like telomerase repeat amplification protocol (TRAP) or immunodetection methods based on antibodies or other ligands with specific affinity for telomerase. The level of telomerase activity or of telomerase expression in the cancer cells in the sample, can be an indicator of the aggressiveness of the tumor or of the number or proportion of cancer cells in the enriched sample.

The glycoprotein CD44 is a cell adhesion molecule originally discovered in lymphocytes and granulocytes but is fairly ubiquitously expressed throughout the body. Up regulation of CD44 and in particular of splice variants (CD44v) like CD44v6, CD44v7, CD44v8, CD44v6-10 is typical of many cancers.

In another embodiment of the present invention the presence or the growth and metastatic potential of the cancer cells isolated from the blood of cancer patients is measured by determining the level of expression and/or function of one or more CD44v splice variants in said cancer cells.

One or more cancer markers can be assessed. In one example, a single cancer cell marker is assessed. In another example, a plurality of the cancer cell markers is assessed. The plurality of the markers can be derived from the same or different cells, e.g., different cell markers are detected simultaneously, e.g., using a high-throughput assay.

In one embodiment of the present invention following the enrichment of the cancer cells from a blood sample, the cancer cells are identified by labeling with monoclonal antibodies recognizing one or more Cytokeratins, CD44v6 or other CD44 splice variants, and Telomerase.

In another example, the presence, absence and/or amount of the enriched non-hematopoietic cell or cancer cell can be assessed by identifying nucleic acids such as mRNA of the enriched non-hematopoietic cell or tumor cell. Any suitable methods, especially nucleic acid polymerase based methods, can be used to identify the enriched cell or non-hematopoietic tumor cell. For example, the presence, absence and/or amount of the enriched non-hematopoietic cell or cancer cell can be assessed by PCR. Any suitable PCR methods can be used. (See e.g., Singleton and Sainbury, DICTIONARY OF MICROBIOLOGY AND MOLECULAR BIOLOGY, Third ed., pages 557-560). In one specific embodiment, singleplexed or multiplexed RT-PCR can be used. In another specific embodiment, qRT-PCR or Real Time PCR can be used.

In addition to cell identification analysis, the enriched non-hematopoietic cancer cell can be subjected to additional analysis. Any suitable methods can be used. For example, PCR, RNA-based amplification, oligonucleotide ligation assay (OLA), laser dissection microscopy (LDM), whole genome amplification (WGA), comparative genomic hybridization (CGH), DNA methylation assay, microarray analysis, total DNA content or a combination thereof can be used in the additional analysis. In one specific embodiment, the additional analysis comprises assessing DNA methylation of the enriched non-hematopoietic cancer cell. (Diala et al., *J. Natl. Cancer Inst.,* 71(4):755-64 (1983); Frost et al., *Cancer Metastasis. Rev.,* 2(4):375-8 (1983); and Weber et al., *Nature Genetics,* 37(8):853-62 (2005)).

The present methods can be used for detecting any suitable non-hematopoietic cancer cell in a blood sample. For example, the present methods can be used for detecting a solid tumor cell in a blood sample. Exemplary tumors include hemangioendothelioma, apudoma, choristoma, branchioma, malignant carcinoid syndrome, carcinoid heart disease, carcinoma e.g., Walker, basal cell, basosquamous Ehrlich tumor, merkel cell, mucinous, non-small cell lung, oat cell, papillary, scirrhous, bronchiolar, bronchogenic, squamous cell and transitional cell reticuloendotheliosis, melanoma, chondroblastoma, chondroma, chondrosarcoma, fibroma, fibrosarcoma, myosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, mesenchymoma, mesonephroma, myosarcoma, cementoma, odontoma, teratoma, throphoblastic tumor, adenocarcinoma, adenoma, cholangioma, angiomatosis, cholesteatoma, paraganglioma nonchromaffin, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, antiokeratoma, angioma sclerosing, glomangioma, hemangioma, hemangiopericytoma, hemangiosarcoma, lymphangioma, lymphangiomyoma, lymphangiosarcoma, pinealoma, carcinosarcoma, chondrosarcoma, ameloblastoma, cystosarcoma phyllodes, fibrosarcoma, Brown-Pearce, ductal, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (Kaposi's, and mast-cell), neoplasms (e.g., bone, digestive system, colorectal, liver, pancreatic, pituitary, testicular, orbital, head and neck, central nervous system, acoustic, pelvic, respiratory tract, and urogenital), neurofibromatosis, and cervical dysplasia.

EXAMPLES

Example 1

Enrichment and Analysis of Cancer Cells from a Blood Sample

Materials and Methods

Affinity-purified anti-CD50 monoclonal antibody was obtained from Aviva System Biology (San Diego, Calif.). Normal human blood collected in anti-coagulant ACD tubes were provided by Advanced Biosciences Resource (Alameda, Calif.). NHS Biotin and DAPI were purchased from Pierce (Rockford, Ill.) and Invitrogen (Carlsbad, Calif.), respectively. Avidin coated magnetic beads were generated in house. FITC-anti-CD31 and PE-anti-CD50 mAbs were from Ancel.

Examination of CD50 and CD31 Expression on Carcinoma Cell Lines by FACS

Carcinoma cells from a series of cell lines including human breast cancer (MDA-435S), human colon cancer (DLD-1), human prostate cancer (PC-3), and human cervix cancer (HeLa) were trypsinized, followed by spinning down at 1300 rpm for 5 min. Cells were resuspended in 1% BSA-PBS and aliquoted into a polystyrene FACS tube (Falcon, Product # 352054) to have $1\times10^6$ cells/0.1 ml/tube. Immunofluorescence dye conjugated mAbs including anti-CD50, anti-CD31 and control antibodies were added (1 ug/tube), followed by incubation on ice for 30 min. Cells were washed twice with 1% BSA-PBS at 1300 rpm for 3 min, followed by fixation in 2% paraformaldehyde in PBS, 0.5 ml/tube. Samples were ready for FACS analysis.

Biotinylatyion of anti-CD50 mAb

Anti-CD50 mAb were dialyzed against PBS buffer at 4° C. overnight. For biotin labeling of antibody, 5-30 fold molar of excess biotin were incubated with IgG at 4° C. overnight with rotation. Conjugated Biotin-IgG were quantified using BCA protein assay kit (Pierce).

Coating Biotinylated IgG to the Avidin-Magnetic Beads

Avidin-magnetic beads were washed four times with PBE (PBS containing 0.5% BSA and 10 mM EDTA, pH 7.4) using a magnetic stand, followed by incubation with biotin labeled IgG (5-150 ug biotin-Ab/$10^9$ beads) at 4° C. for 30 min with rotation. Beads were washed four times with PBE to get rid of unconjugated biotin-IgG, and stored in PBE buffer with the starting volume to get $1\times10^9$ beads/ml.

Tumor Cell Enrichment (Negative Depletion)

For all cell spiking studies, spiked with two cells, live carcinoma cells in suspension were labeled with DAPI dissolved in culture media for at least 24 hours. Exact desired number of labeled cells were picked up by means of a micromanipulator (Sutter Instruments) under a microscope. For spiking studies with more than two cells, cells were fixed, permeabilized, and labeled with DAPI, followed by quantification using a hemocytometer. Desired number of cells were estimated by mixing a known number of cells in PBS followed by limited dilution, spiked into 10 ml human blood in 50 ml tube, followed by adjustment of volume to 45 ml with PBE. Blood samples were centrifuged at 1400 rpm for 5 min. The supernatants were removed by aspiration. Forty five ml of red blood cell lysis buffer were added into sedimentary cells and subsequently rotated at room temperature for 8 min. The samples were spun down at 1400 rpm for 5 min. Cell pellets containing WBC and rare cells were washed once with 45 ml PBE at 1400 rpm for 5 min and resuspended in 0.3 ml of PBE. Meanwhile, anti-CD50 beads were washed 3 times with a magnetic stand, 1 ml/wash, and subsequently resuspended in 0.8 ml of PBE. Above resuspended cells were mixed with washed anti-CD50 beads, followed by incubation at room temperature for 30 min with rotation. The sample tube was subsequently put in a magnetic stand for 1 min. The supernatant was completely transferred into an eppendorf tube, followed by centrifugation at 14,000 rpm for 1 min. The supernatant was aspirated, and the remaining cells were resuspended in 10 ul of mounting media, and subsequently subjected to immunofluorescence analysis.

Results

Figure 2:
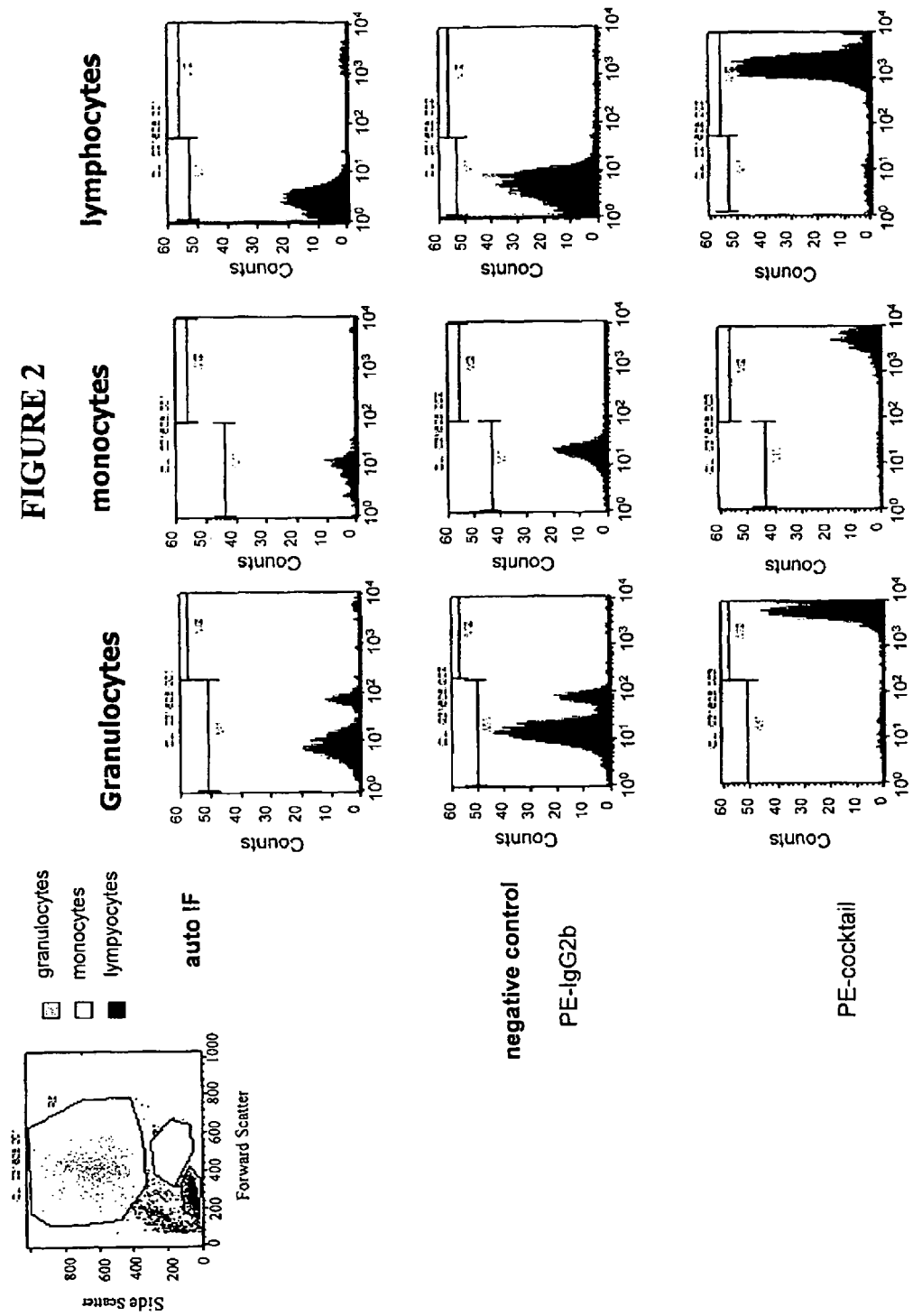
Figure 3:
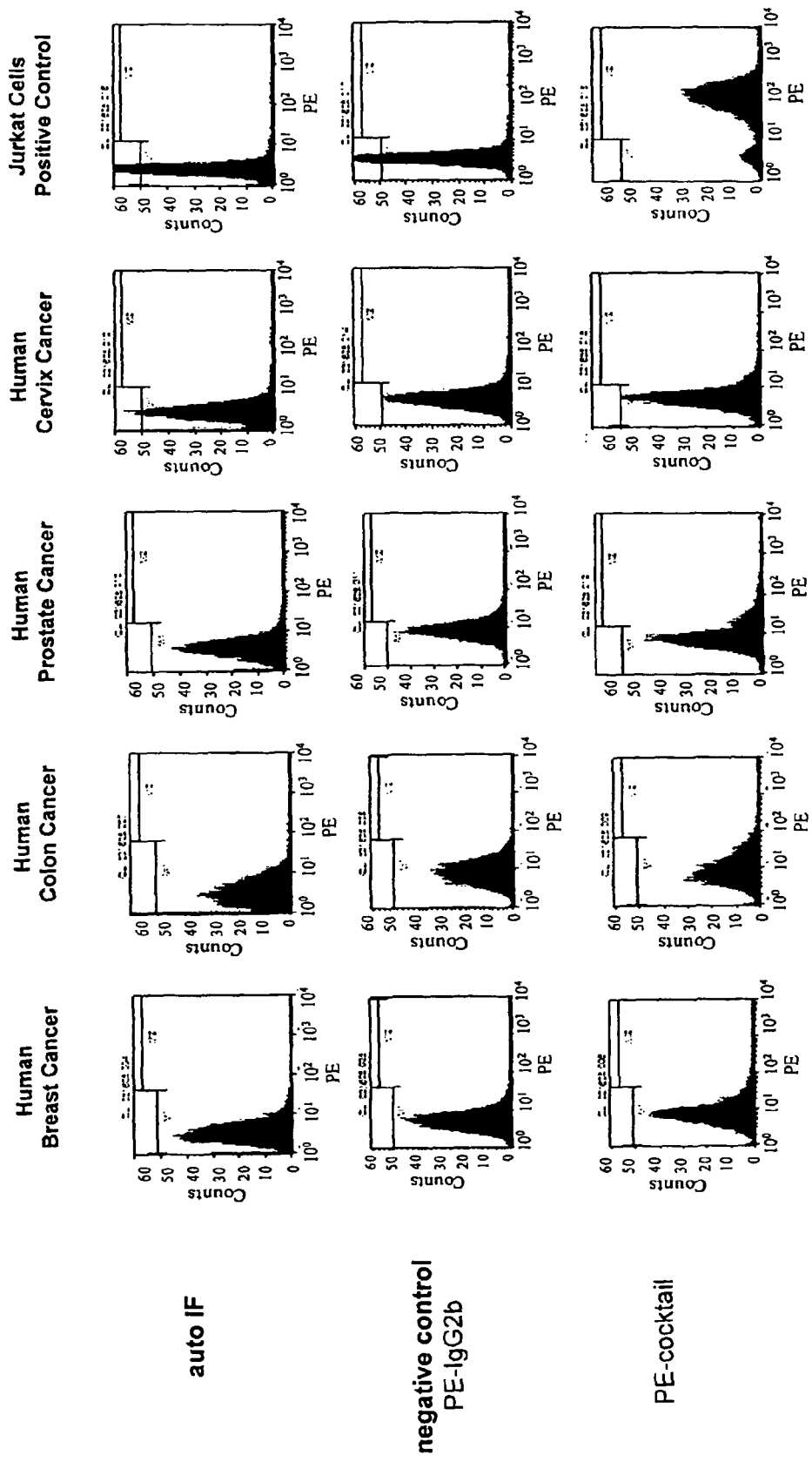

Examination of CD31 and CD50 Expression on Human White Blood Cells and Carcinoma Cells FACS analysis shows strong positive CD50 staining on human WBC including lymphocytes monocytes and granulocytes (FIG. 2). However, human carcinoma cells including breast cancer, colon cancer, prostate cancer and cervix cancer all show negative staining on CD50 (FIG. 3). The positive control Jurkat cells show positive staining on CD50, and negative control antibodies (IgG1 and IgG2b) show negative staining on all cells (FIG. 3). These results, also summarized in the following Tables 1 and 2, indicate that anti-CD50 antibody is suitable for specific removal of only WBCs from human blood.

TABLE 1

CD50 staining on human lymphocytes monocytes and granulocytes

| Mean Value | Granulocytes | Monocytes | Lymphocytes |
|---|---|---|---|
| autofluorescence | 66.12 | 44.98 | 28.77 |
| IgG2b | 30.07 | 17.6 | 6.04 |
| anti-CD50 | 5635.84 | 4911.88 | 1889.66 |

TABLE 2

Lack of CD50 staining on human carcinoma cells

| Mean Value | Breast Cancer Cell | Colon Cancer Cell | Prostate Cancer Cell | Cervix Cancer Cell | Jurkat Cells |
|---|---|---|---|---|---|
| autofluorescence | 3.9 | 3.98 | 4.07 | 3.28 | 2.59 |
| IgG2b | 7.23 | 10.34 | 10.35 | 5.1 | 3.87 |
| anti-CD50 | 13.19 | 16.26 | 14.02 | 6.37 | 182.17 |

Recovery of Spiked Carcinoma Cells from Human Blood

Different numbers of spiked carcinoma cells including HeLa cells, prostate cancer cells, lung cancer and breast cancer cells were isolated from human blood by means of the negative depletion procedures described herein. For HeLa cells (FIG. 4, black), following spiking with 2, 3, 5, 10 cells into blood, the average recovery rate is 88%, 83%, 86%, 80% and 73%, respectively. In the case of prostate cancer cells ((FIG. 4, grey), when 2 or 10 cells were added, the average recovery rate is 100% and 82%, respectively. For lung cancer cells, when 2 or 10 cells were spiked into blood, the average recovery rate was 100% and 90%. For breast cancer cells, when 2 or 10 cells were spiked into blood, the average recovery rate was 100% and 90%.

The negative depletion procedure illustrated above can be applied to enrich cancer cells, optionally followed by further identification and characterization approaches, such as antibody based positive capturing, FISH, (quantitative) RT-PCR, in situ RT-PCR, in situ hybridization, oligonucleotide ligation assay (OLA), laser dissection microscopy (LDM), whole genome application (WGA) including microarray as well as competitive genomic hybridization (CGH). Once circulating tumor cells (CTC) are enriched from human blood, further identification of tumor cells based upon either qRT-PCR or immunostaining of tumor cells can be performed. For all downstream identification, appropriate selection of a panel of cancer markers can be different intracellular and/or extracellular cell surface markers. For instance, in the case of breast cancer, the markers can be classified into 2 different categories: tissue non-specific markers such as CK8/18, 19 and 20; EGFR, VEGF, FGF, MMP, Mucin, CD44v, beta-hCG; CEA+ CK19; Maspsin etc., and tissue specific markers such as mammaglobulin I. The markers can further comprise apoptotic markers such as caspase 3. A panel of markers for different cancers can be analyzed. Each panel can include both tissue specific and non-specific markers.

Example 2

Figure 5:
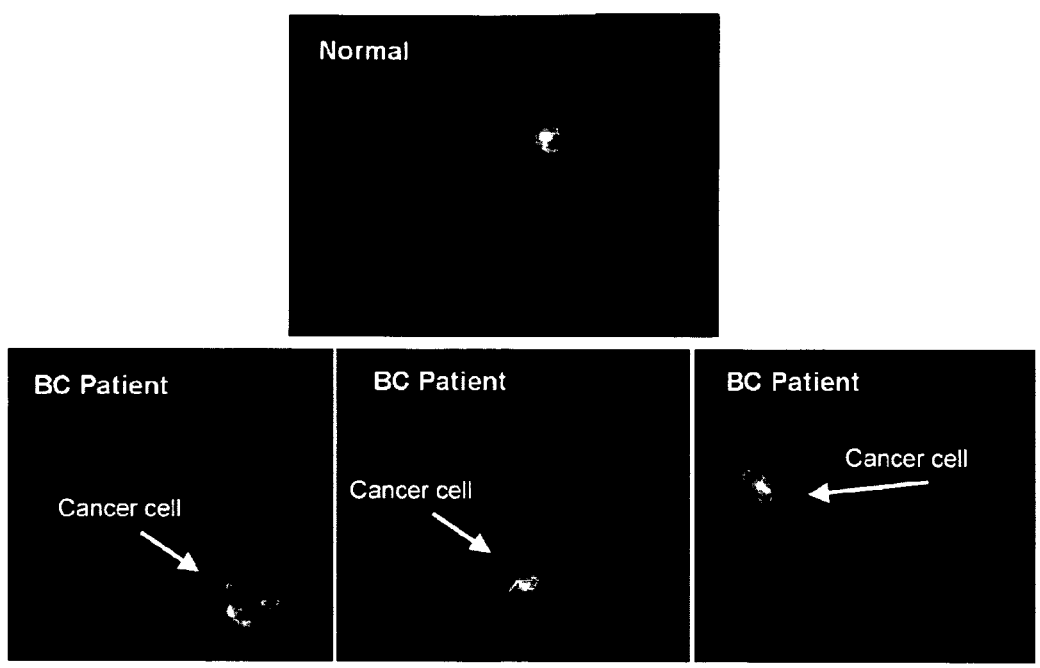

Detection of Isolated Cancer Cells by Immunofluorescence Using a Combination of Tumor Markers Monolayer of enriched cells on slides are immunostained with a mixture of anti-tumor marker mAbs such as anti-CA19.9, anti-cytokeratin and anti-telomerase, labeled with fluorescent dyes, each in a different color, followed by analysis using fluorescence microscopy. Alternatively, immunofluorescence can be indirectly labeled on the antibodies via biotinylation, followed by incubation with fluorescent molecules conjugated to Avidin. In addition, immunofluorescence molecule labeled secondary antibodies are another choice to label the unlabeled primary antibodies recognizing target cells. An example of circulating cancer cells from a patient blood sample identified by this method is illustrated in FIG. 5

Example 3

Detection of Isolated Cancer Cells by Immunofluorescence Using PCR

Following the enrichment of rare cells, RNA is isolated from those cells using magnetic beads, column based methods, or traditional RNA isolation strategies using guanidium, phenol/chloroform. Reverse transcription of RNA is performed using oligo dt, gene specific and/or random primer to generate cDNA as a template. A PCR, a qPCR or multiplex PCR is subsequently carried out to amplify specific target genes such as tumor markers.

Reverse transcription buffer was added to the enriched sample comprising the target rare cells. Direct lyses of the cells was performed by heating the enriched samples at 95° C. for 1 min.

Reverse Transcription of RNA Using Oligo dT, Gene Specific and/or Random Primer to Generate cDNA:

Resuspend above isolated lysed rare cell sample with RNA into 11 µl dNTP mixture (1 mM each) and primer (50 µM oligo(dT), 2 µM gene specific primer and/or 50 ng/µl random hexamer). Incubate at 70° C. for 5 minutes and chill on ice. Add 5 µl reaction buffer (250 mM Tris-HCl (pH 8.3 at 25° C.), 250 mM KCl, 20 mM MgCl$_2$, 50 mM DTT), 20u Ribonuclease inhibitor (Promega), and DEPC-treated water to total 20 µl, incubate at 42° C. for 5 minutes. If random primer is used, incubate at 25° C. for 5 minutes. Add 200 units of SuperScript II (Invitrogen). Incubate the reaction mixture at 42° C. for 60 minutes. If using random hexamer primer, incubate at 25° C. for 10 minutes and then at 42° C. for 60 minutes. Terminate reaction at 85° C. for 5 minutes and chill on ice.

Amplification of Specific Target cDNAs by Multiplex PCR:

Mix all primers together to have first run PCR (20-35 cycles), then perform second run PCR by individual primer using aliquot from first run PCR as template (25-45 cycles). Optimize PCR conditions for each combination of the primers (first run and second run, MgCl$_2$ concentration, annealing temperature, extension time, primer concentration, and primer design). Add PCR mixture into the RT reaction, adjust volume of reaction to 50 µl using autoclaved filtered water (pH 7.0). The component of PCR reaction are: 1×PCR mixture (the final concentration of each components are: 50 mM KCl; 10 mM Tris-HCl; 1.5 mM MgCl$_2$), 200 µM dNTP, 0.4 µl CM of each primers, 1 unit of Taq DNA polymerase, 2% DMSO.

Example 4

Isolation and Detection of Circulating Cancer Cells from Patients with Pancreatic Cancer Table 3 shows the number of circulating cancer cells enriched and identified from human subjects using the methods described in the present invention. Reported in the Table are the results from blinded experiments of blood samples from 7 pancreatic cancer patients and 5 control healthy subjects. In addition, the number of circulating cancer cells from 2 patients with benign tumors are shown. In none of the control healthy individuals was the number of circulating cancer-like cells higher than 8. In addition the 2 patients with benign tumors had 0 or 1 cancer-like cell in their blood samples. In contrast, all of the patients previously diagnosed with pancreatic cancer had >20 cancer cells per sample of blood. Two patients (no. 3 and no. 6) provided blood samples before and after chemotherapy. For patient no. 3 the positive effect of chemotherapy can be seen in the drop in the number of circulating cancer cells (from 134 to 5), while patient no. 6 does not appear to respond favorably to the therapy. This example illustrates how the methods described in the present invention can be used to distinguish between healthy individuals and patients with cancer and to provide a diagnosis for metastatic cancer. It also suggests the potential use of this method to monitor patient response to therapies.

TABLE 3

| Subject # | Diagnosis | CTC No. |
| --- | --- | --- |
| 1 | pancreatic cancer | 20 |
| 2 | pancreatic cancer | 65 |
| 3 | pancreatic cancer | 134 |
| 3 | pancreatic cancer, post chemo | 5 |
| 4 | pancreatic cancer | 21 |
| 5 | pancreatic cancer | 45 |
| 6 | pancreatic cancer | 23 |
| 6 | pancreatic cancer, post chemo | 34 |
| 7 | pancreatic cancer | 40 |
| 8 | benign tumor | 1 |
| 8 | benign tumor, different draw | 0 |
| 9 | benign tumor | 0 |
| 10 | healthy donor | 1 |
| 11 | healthy donor | 1 |
| 12 | healthy donor | 5 |
| 13 | healthy donor | 4 |
| 14 | healthy donor | 8 |

Example 5

Isolation and Detection of Circulating Cancer Cells from Patients with Lung Cancer Table 4 reports the results obtained when the methods described in the present invention were used to isolate and detect cancer cells in blood samples from individuals with lung cancer. In this study the possibility that cancer-like cells could be detected in the blood as a non specific artifact resulting from the compromised general health of the patients, individuals diagnosed with tuberculosis were used as controls. All the control individuals had no more than 1 cancer-like cell isolated from a blood sample, while all the patients previously diagnosed with various forms of lung cancer (adenocarcinoma, AD; small-cell-lung cancer, SCLC), under various treatment status had 2 or more cancer cells per blood samples.

selection' methods rely upon a characteristic surface marker or ligand on the target cell to pull the target cell from a mixture by binding the surface marker or ligand to a selective binding member that is selective for it; typically the selective binding member is affixed to a solid surface or particle, so that the target cell is readily isolated by separating the remaining mixture from the solid surface or particle. A comparison of the performance of a positive selection method and the depletion approach described in the present invention is illustrated in Table 5.

TABLE 5

| Classfication | Selection | Depletion |
|---|---|---|
| Control-1 | 1 | 1 |
| Control-2 | 1 | 4 |
| Control-3 | 0 | 1 |

TABLE 4

| Patient | Age | Diagnosis | Stage | Metastasis | Surgery | Number of chema treatments | Number of radiation treatments | Number of circulating cancer cells | Note |
|---|---|---|---|---|---|---|---|---|---|
| 1 | n.a. | TB | | | | | | 0 | |
| 2 | n.a. | TB | | | | | | 0 | |
| 3 | n.a. | TB | | | | | | 0 | |
| 4 | n.a. | TB | | | | | | 0 | |
| 5 | n.a. | TB | | | | | | 0 | |
| 6 | n.a. | TB | | | | | | 0 | |
| 7 | n.a. | TB | | | | | | 0 | |
| 8 | n.a. | TB | | | | | | 0 | |
| 9 | n.a. | TB | | | | | | 0 | |
| 10 | 65 | Unknown | | | | | | 0 | |
| 11 | 77 | Bladder | | | | | | 1 | |
| 12 | n.a. | TB | | | | | | 1 | |
| 13 | 42 | Thymus | | | | | | 1 | |
| 14 | 65 | AC | n.a. | | after | 2 | | 2 | Relapse |
| 15 | 46 | AC | IIIA | | after | 6 | | 2 | |
| 16 | 55 | AC(HD) | Ib | | after | 6 | | 2 | |
| 17 | 40 | Unknown | n.a. | | n.a. | n.a. | | 2 | |
| 18 | 66 | SCC | IIb | | before | 3 | | 3 | |
| 19 | 50 | SCC | IIIA | | n.a. | 4 | 1 | 3 | |
| 20 | 48 | Unknown | IV | Brain | before | 0 | | 3 | |
| 21 | 65 | AC | n.a. | | after | 3 | | 4 | |
| 22 | 37 | AC | IIIb | | after | 6 | | 4 | |
| 23 | 64 | AC | IIIb | | none | 5 | | 5 | 2nd line |
| 24 | 68 | SCLC | IV | Lungs/Liver | n.a. | 4 | | 7 | |
| 25 | 65 | AC | IIb | | after | 0 | | 8 | |
| 26 | n.a. | Prostate | n.a. | | n.a. | n.a. | | 9 | |
| 27 | 70 | AC(MD) | IV | Lungs | none | 2 | | 11 | |
| 28 | 68 | SCLC | n.a. | | n.a. | 0 | | 14 | |
| 29 | 60 | AC | IIb | | after | 0 | | 15 | |
| 30 | 65 | AC | Ib | | before | 0 | | 16 | |
| 31 | 50 | SCC | IIIA | | after | 3 | 1 | 16 | |
| 32 | 73 | AC | IV | Lungs | none | 4 | | 21 | 2nd line |
| 33 | 71 | AC | n.a. | | n.a. | 6 | 1 | 22 | |
| 34 | 75 | SCLC | IIIb | | none | 2 | | 34 | |
| 35 | 60 | AC | IIb | | after venal tie | n.a. | | 57 | |
| 36 | 72 | SCLC | IV | Lungs | n.a. | 0 | | 75 | |
| 37 | 60 | AC | IIb | | before | 0 | | 85 | |

Example 6

Comparison of Depletion Vs Selection Methods for Isolating and Detecting Cancer Cells in the Blood of Cancer Patients In recent years a number of methods have been developed for enriching cancer cells from blood samples using positive selection technologies, whereby centrifugation, selective binding to solid support or combinations thereof have been used to capture target cells from a sample. These 'positive TABLE 5-continued

| Classfication | Selection | Depletion |
|---|---|---|
| Control-4 | 1 | 3 |
| Control-5 | 0 | 4 |
| Control-6 | 0 | 4 |
| Control-7 | 1 | 3 |
| Control-8 | 0 | 2 |
| Control-9 | 1 | 5 |
| Spike1-20 | 11 | 18 |
| Spike2-20 | 8 | 17 |

TABLE 5-continued

| Classfication | Selection | Depletion |
|---|---|---|
| Spike3-20 | 11 | 27 |
| Spike4-20 | 25 | 17 |
| Spike5-50 | 39 | 56 |
| Spike6-50 | 84 | 54 |
| Spike7-100 | 106 | 111 |
| Spike8-100 | 91 | 108 |
| Spike9-100 | 502 | 117 |
| Patient-1 | 3 | 3 |
| Patient-2 | 14 | 20 |
| Patient-3 | 0 | 36 |
| Patient-4 | 13 | 39 |
| Patient-5 | 0 | 27 |
| Patient-6 | 0 | 14 |
| Patient-7 | 0 | 13 |
| Patient-8 | 0 | 18 |

In this study, the samples processed with the positive selection method were analyzed using magnetic beads coupled with anti-EpCAM monoclonal antibodies, to capture epithelial-like cells. In all the experiments used to generate the data in Table 3 the blood samples were split into two aliquots which were processed in parallel using the two methods. The first 9 samples were obtained from healthy control subjects. The depletion methods described in the present invention produced up to 5 cancer-like cells while a slightly lower background was detected in the samples processed using EpCAM-based selection (up to 1 cancer-like cell per sample).

To evaluate the general recovery rate of the two approaches blood samples from healthy individuals were spiked with 20, 50 or 100 tumor cells (as indicated in the "Classification"). In this experiment the depletion method provided more consistent recovery efficiencies, better aligned with the expected number of cancer cells in the sample. This demonstrates that the negative selection method can perform better for the purposes of detecting cancers, monitoring their treatment, etc. than the positive selection method. Recovery of the target cells would of course be further reduced if some or all of the target cells had undergone some type of modification of the surface marker or ligand (e.g., mutations) that the positive-selection method relied upon to affix or label the target cells. Nevertheless, in some embodiments, the present methods may include a positive selection step as part of a target cell isolation process, or as a labeling step to characterize the cells once they have been isolated or enriched.

This set of data was obtained from testing blood samples from patients previously diagnosed with breast cancer. For 1 patient (no. 1) there is good agreement between the results obtained with the two methods. For two other patients, number 2 and number 4, the depletion methods results in twice the number of cancer cells detected when compared to the positive selection method. For all of the remaining patients however, the positive selection methods reported 0 cancer cells while the depletion method allowed the detection of 13 to 36 cancer cells. These are patients known to have metastatic cancer for which the selection method would have completely missed the diagnosis and for which the depletion methods described in this patent provided a better diagnostic option.

Example 7

Isolation of Rare Cells from Human Blood

In this example, blood samples from thirteen healthy donors were spiked with different number of mitotracker/Hoechst-labeled SKBR or A549 cells. Five ml of human blood were mixed with the same volume of Hank's buffered saline containing 5 mM EDTA and 0.5% BSA, followed by adding 0.1 ml of anti-CD50 conjugated magnetic beads (diameter ~350 nm; concentration of $4 \times 10^9$/ml). Reaction solution was mixed at room temperature for 5 mins, and then loaded on the top of 3 ml separation medium based on Ficoll, diluted to 90% with Hank's buffer (For Ficoll, density=1.077 g/100 ml). The solution was centrifuged at 350 g for 5 min at room temperature. Supernatant above the RBC layer was collected, followed by spinning at 1200 g for 5 min at room temperature. The cell pellet was collected for microscopic analysis. The result is listed in Table 6.

TABLE 6

| Exp't | Cell # Spiked | Cell # Recovered | Recovery Rate |
|---|---|---|---|
| 1 | 37 | 33 | 89% |
| 2 | 43 | 38 | 88% |
| 3 | 40 | 38 | 95% |
| 5 | 60 | 52 | 87% |
| 6 | 54 | 35 | 65% |
| 7 | 47 | 36 | 77% |
| 8 | 31 | 28 | 90% |
| 9 | 42 | 33 | 79% |
| 10 | 34 | 31 | 91% |
| 11 | 44 | 31 | 70% |
| 12 | 37 | 30 | 81% |
| 13 | 36 | 32 | 89% |
| Average | | | 83% |
| SD | | | 9% |

Example 8

Detection of CTCs from Lung Cancer Patient Blood Samples and Correlation with Anti-Cancer Therapy Blood Collection: 7.5 ml venous blood sample was drawn into BD Vacutainer® ACD tubes after the initial 2 ml was discarded. For CTC and CT scan correlation study, blood samples were drawn from 12 late stage lung cancer patients one day before and two weeks after cancer patients completed chemotherapy. WBCs were prepared and incubated with CD50 antibody coated magnetic beads. After bead separation, enriched rare cell portion was centrifuged and the resulting cell pellet was suspended and spotted on coated slides, and fixed. Cancer cell detection by immunofluorescence staining Slides were stained with anti-cytokeratin 8/18 Alexa 594, anti-cytokeratin 19 Alexa 488, and counterstained by DAPI and examined under a fluorescent microscope. Cancer progression monitoring Clinical responses were monitored by CT scan two months after the completion of chemotherapy and judged according to the RECIST. (FIG. 6)

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims. Citation of the above publications or documents is not intended as an admission that any of the foregoing is pertinent prior art, nor does it constitute any admission as to the contents or date of these publications or documents.

What is claimed is:

1. A method for isolating a target cell from a biological sample containing other types of cells, said method comprising:
   a) enriching the sample by selectively removing at least one non-target cell type without removing the target cell;
   b) debulking the sample by reducing the sample volume without removing the target cell; and
   c) subjecting the enriched sample comprising the target cell to a downstream process that identifies, characterizes, or utilizes the target cell population
   wherein the target cell is an epithelial cell, a mesenchymal cell, a tumor cell, an infected cell, a mutated cell, a damaged cell, a stem cell, or a fetal cell, and
   1) wherein the target cell is identified by detection of telomerase activity or by detection of a CD44 splice variant; or
   2) wherein the method further comprises a step of determining whether the target cell has a therapeutic antibody bound to it; or
   3) wherein the method is used to evaluate a cancer therapeutic process or to determine a clinical end point for a cancer drug evaluation process.

2. A method for isolating a target cell from a biological sample containing other types of cells, said method comprising:
   a) enriching the sample by selectively removing at least one non-target cell type without removing the target cell;
   b) debulking the sample by reducing the sample volume without removing the target cell; and
   c) subjecting the enriched sample comprising the target cell to a downstream process that identifies, characterizes, or utilizes the target cell population,
   wherein the target cell is an epithelial cell, a mesenchymal cell, a tumor cell, an infected cell, a mutated cell, a damaged cell, a stem cell, or a fetal cell,
   wherein the presence, number, proportion, or property of the target cell(s) in the sample is used to evaluate the subject from which the biological sample is obtained, and
   1) wherein the isolated target cell is grown in suitable media to produce a culture of cancerous cells; or
   2) wherein the target cell is a cell to which a therapeutic antibody is bound.

3. The method of claim 2, wherein the culture of cancerous cells is used to evaluate a drug candidate or a cancer therapy treatment protocol.

4. A method for detecting a non-hematopoietic cancer cell in a blood sample, comprising the steps of:
   a) removing the majority of the hematopoietic cells from the sample using depletion methods without removing the cancer cells if any are present, to provide an enriched sample; and
   b) assessing the presence or activity level of telomerase in the enriched sample, or detecting the presence or expression level in the enriched sample of a nucleic acid that encodes telomerase;
   wherein the presence or amount of telomerase activity or telomerase nucleic acid or telomerase expression is used to determine a probability that the blood sample contained at least one cancer cell.

5. The method of claim 4, wherein the presence or activity level of telomerase in the enriched sample is assessed by telomerase repeat amplification protocol (TRAP).

6. The method of claim 4, wherein the presence of telomerase in the enriched sample is determined using immunodetection methods to detect the telomerase protein itself.

7. The method of claim 4, which comprises removing white blood cells (WBCs) by allowing them to bind to a specific binding member affixed to a solid support.

8. The method of claim 7, wherein the specific binding member is a CD50 antibody or a CD45 antibody.

* * * * *